US007507787B2

(12) United States Patent
Hancock et al.

(10) Patent No.: US 7,507,787 B2
(45) Date of Patent: Mar. 24, 2009

(54) EFFECTORS OF INNATE IMMUNITY

(75) Inventors: Robert E. W. Hancock, Vancouver (CA); B. Brett Finlay, Richmond (CA); Monisha Gough Scott, Vancouver (CA); Dawn Bowdish, Vancouver (CA); Carrie Melissa Rosenberger, Vancouver (CA); Jon-Paul Steven Powers, Vancouver (CA)

(73) Assignee: The University of British Columbia, Vancouver, British Columbia (CA)

( * ) Notice: Subject to any disclaimer, the term of this patent is extended or adjusted under 35 U.S.C. 154(b) by 681 days.

(21) Appl. No.: 10/308,905

(22) Filed: Dec. 2, 2002

(65) Prior Publication Data

US 2004/0001803 A1 Jan. 1, 2004

Related U.S. Application Data

(60) Provisional application No. 60/336,632, filed on Dec. 3, 2001.

(51) Int. Cl.
*A61K 38/00* (2006.01)
*A61K 38/28* (2006.01)
*A61K 38/04* (2006.01)
*C07K 14/00* (2006.01)
*C07K 16/00* (2006.01)

(52) U.S. Cl. .................. 530/300; 530/305; 530/327
(58) Field of Classification Search .............. 435/6, 435/91.1, 183, 68.1, 69.1; 530/300, 350, 530/305, 327, 333
See application file for complete search history.

(56) References Cited

U.S. PATENT DOCUMENTS

| 5,593,866 | A | 1/1997 | Hancock et al. |
| 5,688,767 | A | 11/1997 | Hancock et al. |
| 5,707,855 | A | 1/1998 | Hancock et al. |
| 5,789,377 | A | 8/1998 | Hancock et al. |
| 6,040,435 | A | 3/2000 | Karunaratne et al. |
| 6,143,498 | A | 11/2000 | Olsen et al. |
| 6,172,185 | B1 | 1/2001 | Hancock et al. |
| 6,191,254 | B1 | 2/2001 | Falla et al. |
| 6,358,921 | B1 | 3/2002 | Kondejewski et al. |
| 6,433,013 | B1 | 8/2002 | Verschoor et al. |
| 6,440,690 | B1 | 8/2002 | Mor et al. |
| 2002/0035061 | A1 | 3/2002 | Krieger et al. |
| 2002/0064501 | A1 | 5/2002 | Khan et al. ................ 424/9.2 |
| 2002/0072495 | A1 | 6/2002 | Chertov et al. |
| 2002/0082195 | A1 | 6/2002 | Lehrer et al. |

FOREIGN PATENT DOCUMENTS

| CA | 2456477 A1 | 2/2003 |
| CA | 2468907 A1 | 6/2003 |
| WO | WO0012528 A | 3/2000 |

OTHER PUBLICATIONS

Tamamura et al., Pharmacophore identification of a chemokine receptor (CXCR4) antagonist, T22 ([Tyr(5,12),Lys7]-polyphemusin II), which specifically blocks T cell-line-tropic HIV-1 infection. Bioorganic & Medicinal Chemistry, 6, 1033-1041, 1998.*
Bailer et al., IL-13 and TNF-alpha inhibit dual-tropic HIV-1 in primary macrophages by reduction of surface expression of CD4, chemokine receptors CCR5, CXCR4 and post-entry viral gene expression. Eur. J. Immunol, 30, 1340-1349, May 2000.*
Nanki et al., Cutting edge: stromal cell-derived factor-1 is a costimulator for CD4+ T cell activation. The Journal of Immunology, 164, 5010-5014, May 2000.*
Scott MG. et al., "An alpha-Helical Cationic Antimicrobial Peptide Selectively Modulates Macrophage Responses to Lipopolysaccharide and Directly Alters Macrophage Gene Expression", *The Journal of Immunology*, vol. 165, 3358-3365, 2000.
Scott, MG. et al., "Biological Properties of Structurally Related alpha-Helical Cationic Antimicrobial Peptides", *Infection and Immunity*, vol. 67, No. 4, 2005-2009, Apr. 1999.
Scott MG. et al., "The Human Antimicrobial Peptide LL-37 Is a Multifunctional Modulator of Innate Immune Responses", *The Journal of Immunology*, vol. 169, 3883-3891, 2002.
Hancock R.E. et al., "The role of cationic antimicrobial peptides in innate host defenses", *Trends in Microbiology*, vol. 8, No. 9, 402-410, Sep. 2000.
Hancock, R.E., "Host Defense (Cationic) Peptides, What is Their Future Clinical Potent ional?", *Drugs*, vol. 57, No. 4, 469-473, Apr. 1999.
Finlay, B.B. et al., "Perspectives, Can innate immunity be enhanced to treat microbial infections?", *Nature Reviews Microbiology*, vol. 2, 497-504, Jun. 2004.
Giacometti et al., "Potential Therapeutic Role of Cationic Peptides in Three Experimental Models of Septic Shock", *Antimicrobial Agent and Chemotherapy*, 2132-2136, Jul. 2002.
Bowdish, D.M.E., et al., "The Human Cationic Peptide LL-37 Induces Activation of the Extracellular Signal-Regulated Kinases and p38 Kinase Pathways in Primary Human Monocytes", *The Journal of Immunology*, vol. 172, 3758-3765, 2004.
Hancock R.E. et al., "The role of antimicrobial peptides in animal defense", *Proceedings of The National Academy of Sciences of The United States of America*, vol. 97, No. 16, 8856-8861, Aug. 1, 2000.

(Continued)

*Primary Examiner*—Frank W Lu
(74) *Attorney, Agent, or Firm*—DLA Piper LLP (US)

(57) ABSTRACT

A method of identifying a polynucleotide or pattern of polynucleotides regulated by one or more sepsis or inflammatory inducing agents and inhibited by a peptide is described. A method of identifying a pattern of polynucleotide expression for inhibition of an inflammatory or septic response. The method includes contacting cells with LPS, LTA, CpG DNA and/or intact microbe or microbial components in the presence or absence of a cationic peptide; detecting a pattern of polynucleotide expression for the cells in the presence and absence of the peptide, wherein the pattern in the presence of the peptide represents inhibition of an inflammatory or septic response. Also included are compounds and agents identified by the methods of the invention. In another aspect, the invention provides methods and compounds for enhancing innate immunity in a subject.

1 Claim, No Drawings

OTHER PUBLICATIONS

Luftfalla, G. et al., "Mutant U5A cells are complemented by an interferon-alpha beta receptors subunit generated by alternative processing of a new member of a cytokine receptor gene cluster", http://www.ncbi.nlm, accession No. L042243, Apr. 4, 1996.

Mishima, K. et al., "ARD1, a 64-kDa guanine nucleotide-binding protein with a carboxyl-terminal ADP-ribosylation factor domain", http://www.ncbi.nlm, accession No. L04510, Jun. 12, 1993.

Van Wetering, S., "Defensins: Key Players or Bystanders in Infection, Injury, and Repair in the Lungs?", *Journal of Allergy and Clinical Immunology*, Mosby-Yearlybook, Inc., US, vol. 104, No. 6, 1131-1138, 1999.

Doranz, B.J. et al., "A Small-Molecule Inhibitor Directed Against The Chemokine Receptor CXCR4 Prevents its Use as an HIV-1 Corecptor", *Journal of Experimental Medicine*, Tokyo, JP, vol. 186, No. 8, 1395-1400, Oct. 20, 1997.

Sareneva, T. et al., "Ifn-α and IL-12 Induce IL-18 Receptor Gene Expression in Human NK and T Cells," *The Journal Of Immunology*, vol. 165: 1993-1938, 2000.

Wu, H. et al. "Regulation of Cathelicidin Gene Expression: Induction by Lipopolysacchride, interleukin-6, Retinoic Acid, and *Salmonella enterica* Serovar Typhimurium Infection", *Infection and Immunity*, 5552-5558, 2000.

Scott, M.G. et al., "Cationic Antimicrobial Peptide and Their Multifunctional Role in the Immune System", *Critical Review in Immunology*, CRC Press, vol. 20, 407-431, 2000.

Hancock, R.E. and Lehrer, R., "Cationic peptides: a new source of antibiotics", *Trends in Biology, Elsevier Publication*, vol. 16, No. 2, Feb. 1, 1998.

Hancock, R.E., "Catitonic peptides:effectors in innate immunity and novel antimicrobials", The Lancet Infectious Diseases, vol. 1 No. 3, 156-164, Oct. 2001.

Mcquibban, G.A. et al., "Matrix Metalloproteinase Activity Inactivates the CXC Chemokine Stromal Cell-derived Factor-1", *The Journal of Biological Chemistry*, vol. 276, No. 47, Nov. 23, 2001.

Chung et al., "STAT3 Serine Phosphorylation by ERK-Dependent and—Independent Pathways Negatively Modulates Its Tyrosine Phosphorylation", *Molecular and Cellular Biology*, 17(11):6508-6516 (1997).

Granulocyte-macrophage colony stimulating factor (GM-CSF). (http://www.nichd.nih.gov/cochrane/Carr/CARR.HTM).

Granulocyte-macrophage colony stimulating factor (GM-CSF). Online Medical Dictionary, http://cancerweb.ncl.ac.uk/cgi-bin/omd?query=GM-CSF, (Dec. 12, 1988).

Schindler & Brutsaert, "Interferons as a paradigm for cytokine signal transduction", *CMLS, Cellular and Molecular Life Sciences*, 55:1509-1522 (1999).

\* cited by examiner

SEQUENCE LISTING

```
<160> NUMBER OF SEQ ID NOS: 58

<210> SEQ ID NO 1
<211> LENGTH: 37
<212> TYPE: PRT
<213> ORGANISM: Homo sapiens

<400> SEQUENCE: 1

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
        35

<210> SEQ ID NO 2
<211> LENGTH: 13
<212> TYPE: PRT
<213> ORGANISM: Bovine

<400> SEQUENCE: 2

Ile Leu Pro Trp Lys Trp Pro Trp Trp Pro Trp Arg Arg
1               5                   10

<210> SEQ ID NO 3
<211> LENGTH: 12
<212> TYPE: PRT
<213> ORGANISM: Bovine

<400> SEQUENCE: 3

Arg Leu Ala Arg Ile Val Val Ile Arg Val Ala Arg
1               5                   10

<210> SEQ ID NO 4
<211> LENGTH: 14
<212> TYPE: PRT
<213> ORGANISM: Artificial sequence
<220> FEATURE:
<223> OTHER INFORMATION: Cationic peptide
```

```
<220> FEATURE:
<221> NAME/KEY: MISC_FEATURE
<222> LOCATION: (1)..(2)
<223> OTHER INFORMATION: Xaa is independently R, L or K and one or both
      may be present
<220> FEATURE:
<221> NAME/KEY: MISC_FEATURE
<222> LOCATION: (3)..(3)
<223> OTHER INFORMATION: Xaa is one of C, S or A
<220> FEATURE:
<221> NAME/KEY: MISC_FEATURE
<222> LOCATION: (4)..(4)
<223> OTHER INFORMATION: Xaa is one of R or P
<220> FEATURE:
<221> NAME/KEY: MISC_FEATURE
<222> LOCATION: (6)..(6)
<223> OTHER INFORMATION: Xaa is one of A or V
<220> FEATURE:
<221> NAME/KEY: MISC_FEATURE
<222> LOCATION: (8)..(8)
<223> OTHER INFORMATION: Xaa is one of A or V
<220> FEATURE:
<221> NAME/KEY: MISC_FEATURE
<222> LOCATION: (11)..(11)
<223> OTHER INFORMATION: Xaa is one of V or W
<220> FEATURE:
<221> NAME/KEY: MISC_FEATURE
<222> LOCATION: (12)..(12)
<223> OTHER INFORMATION: Xaa is one of C, S or A
<220> FEATURE:
<221> NAME/KEY: MISC_FEATURE
<222> LOCATION: (13)..(14)
<223> OTHER INFORMATION: Xaa is independently R, L or K and one or both
      may be present

<400> SEQUENCE: 4

Xaa Xaa Xaa Xaa Ile Xaa Pro Xaa Ile Pro Xaa Xaa Xaa Xaa
1               5                   10

<210> SEQ ID NO 5
<211> LENGTH: 13
<212> TYPE: PRT
<213> ORGANISM: Artificial sequence
<220> FEATURE:
<223> OTHER INFORMATION: Cationic peptide

<400> SEQUENCE: 5

Leu Leu Cys Arg Ile Val Pro Val Ile Pro Trp Cys Lys
1               5                   10

<210> SEQ ID NO 6
<211> LENGTH: 14
<212> TYPE: PRT
<213> ORGANISM: Artificial sequence
<220> FEATURE:
<223> OTHER INFORMATION: Cationic peptide

<400> SEQUENCE: 6

Leu Arg Cys Pro Ile Ala Pro Val Ile Pro Val Cys Lys Lys
1               5                   10

<210> SEQ ID NO 7
<211> LENGTH: 13
<212> TYPE: PRT
<213> ORGANISM: Artificial sequence
<220> FEATURE:
<223> OTHER INFORMATION: Cationic peptide

<400> SEQUENCE: 7

Lys Ser Arg Ile Val Pro Ala Ile Pro Val Ser Leu Leu
1               5                   10
```

```
<210> SEQ ID NO 8
<211> LENGTH: 13
<212> TYPE: PRT
<213> ORGANISM: Artificial sequence
<220> FEATURE:
<223> OTHER INFORMATION: Cationic peptide

<400> SEQUENCE: 8

Lys Lys Ser Pro Ile Ala Pro Ala Ile Pro Trp Ser Arg
1               5                   10

<210> SEQ ID NO 9
<211> LENGTH: 14
<212> TYPE: PRT
<213> ORGANISM: Artificial sequence
<220> FEATURE:
<223> OTHER INFORMATION: Cationic peptide

<400> SEQUENCE: 9

Arg Arg Ala Arg Ile Val Pro Ala Ile Pro Val Ala Arg Arg
1               5                   10

<210> SEQ ID NO 10
<211> LENGTH: 13
<212> TYPE: PRT
<213> ORGANISM: Artificial sequence
<220> FEATURE:
<223> OTHER INFORMATION: Cationic peptide

<400> SEQUENCE: 10

Leu Ser Arg Ile Ala Pro Ala Ile Pro Trp Ala Lys Leu
1               5                   10

<210> SEQ ID NO 11
<211> LENGTH: 16
<212> TYPE: PRT
<213> ORGANISM: Artificial sequence
<220> FEATURE:
<223> OTHER INFORMATION: Cationic peptide
<220> FEATURE:
<221> NAME/KEY: MISC_FEATURE
<222> LOCATION: (1)..(2)
<223> OTHER INFORMATION: Xaa is independently D, E, S, T or N and one or
      both may be present
<220> FEATURE:
<221> NAME/KEY: MISC_FEATURE
<222> LOCATION: (4)..(5)
<223> OTHER INFORMATION: Xaa is P, G or D and one or both may be present
<220> FEATURE:
<221> NAME/KEY: MISC_FEATURE
<222> LOCATION: (6)..(6)
<223> OTHER INFORMATION: Xaa is one of G, A, V, L, I or Y
<220> FEATURE:
<221> NAME/KEY: MISC_FEATURE
<222> LOCATION: (8)..(8)
<223> OTHER INFORMATION: Xaa is one of R, K or H
<220> FEATURE:
<221> NAME/KEY: MISC_FEATURE
<222> LOCATION: (9)..(10)
<223> OTHER INFORMATION: Xaa is P, G or D and one or both may be present
<220> FEATURE:
<221> NAME/KEY: MISC_FEATURE
<222> LOCATION: (11)..(11)
<223> OTHER INFORMATION: Xaa is one of S, T, C, M or R
<220> FEATURE:
<221> NAME/KEY: MISC_FEATURE
<222> LOCATION: (12)..(12)
<223> OTHER INFORMATION: Xaa is one of G, A, V, L, I or Y
<220> FEATURE:
<221> NAME/KEY: MISC_FEATURE
<222> LOCATION: (14)..(14)
```

```
<223> OTHER INFORMATION: Xaa is one of G, A, V, L, I or Y
<220> FEATURE:
<221> NAME/KEY: MISC_FEATURE
<222> LOCATION: (15)..(16)
<223> OTHER INFORMATION: Xaa is D, E, S, T or N and one or both may be
      present

<400> SEQUENCE: 11

Xaa Xaa Leu Xaa Xaa Xaa Lys Xaa Xaa Xaa Xaa Xaa Pro Xaa Xaa Xaa
1               5                   10                  15

<210> SEQ ID NO 12
<211> LENGTH: 13
<212> TYPE: PRT
<213> ORGANISM: Artificial sequence
<220> FEATURE:
<223> OTHER INFORMATION: Cationic peptide

<400> SEQUENCE: 12

Asp Leu Pro Ala Lys Arg Gly Ser Ala Pro Gly Ser Thr
1               5                   10

<210> SEQ ID NO 13
<211> LENGTH: 14
<212> TYPE: PRT
<213> ORGANISM: Artificial sequence
<220> FEATURE:
<223> OTHER INFORMATION: Cationic peptide

<400> SEQUENCE: 13

Ser Glu Leu Pro Gly Leu Lys His Pro Cys Val Pro Gly Ser
1               5                   10

<210> SEQ ID NO 14
<211> LENGTH: 14
<212> TYPE: PRT
<213> ORGANISM: Artificial sequence
<220> FEATURE:
<223> OTHER INFORMATION: Cationic peptide

<400> SEQUENCE: 14

Thr Thr Leu Gly Pro Val Lys Arg Asp Ser Ile Pro Gly Glu
1               5                   10

<210> SEQ ID NO 15
<211> LENGTH: 13
<212> TYPE: PRT
<213> ORGANISM: Artificial sequence
<220> FEATURE:
<223> OTHER INFORMATION: Cationic peptide

<400> SEQUENCE: 15

Ser Leu Pro Ile Lys His Asp Arg Leu Pro Ala Thr Ser
1               5                   10

<210> SEQ ID NO 16
<211> LENGTH: 12
<212> TYPE: PRT
<213> ORGANISM: Artificial sequence
<220> FEATURE:
<223> OTHER INFORMATION: Cationic peptide

<400> SEQUENCE: 16

Glu Leu Pro Leu Lys Arg Gly Arg Val Pro Val Glu
1               5                   10
```

-continued

```
<210> SEQ ID NO 17
<211> LENGTH: 14
<212> TYPE: PRT
<213> ORGANISM: Artificial sequence
<220> FEATURE:
<223> OTHER INFORMATION: Cationic peptide

<400> SEQUENCE: 17

Asn Leu Pro Asp Leu Lys Lys Pro Arg Val Pro Ala Thr Ser
1               5                   10

<210> SEQ ID NO 18
<211> LENGTH: 19
<212> TYPE: PRT
<213> ORGANISM: Artificial sequence
<220> FEATURE:
<223> OTHER INFORMATION: Cationic peptide
<220> FEATURE:
<221> NAME/KEY: MISC_FEATURE
<222> LOCATION: (1)..(4)
<223> OTHER INFORMATION: Xaa is chosen from A, P or R and one, two,
      three or all four may be present
<220> FEATURE:
<221> NAME/KEY: MISC_FEATURE
<222> LOCATION: (5)..(6)
<223> OTHER INFORMATION: Xaa is an aromatic amino acid (F, Y and W)
<220> FEATURE:
<221> NAME/KEY: MISC_FEATURE
<222> LOCATION: (7)..(7)
<223> OTHER INFORMATION: Xaa is one of P or K
<220> FEATURE:
<221> NAME/KEY: MISC_FEATURE
<222> LOCATION: (8)..(9)
<223> OTHER INFORMATION: Xaa is chosen from A, P, Y or W and one, both
      or none may be present
<220> FEATURE:
<221> NAME/KEY: MISC_FEATURE
<222> LOCATION: (11)..(12)
<223> OTHER INFORMATION: Xaa is chosen from A, P, Y or W and one, both
      or none may be present
<220> FEATURE:
<221> NAME/KEY: MISC_FEATURE
<222> LOCATION: (14)..(15)
<223> OTHER INFORMATION: Xaa is chosen from A, P, Y or W and one, both
      or none may be present
<220> FEATURE:
<221> NAME/KEY: MISC_FEATURE
<222> LOCATION: (16)..(18)
<223> OTHER INFORMATION: Xaa is chosen from R or P and one, two or three
      may be present

<400> SEQUENCE: 18

Xaa Xaa Xaa Xaa Xaa Xaa Xaa Xaa Xaa Trp Xaa Xaa Trp Xaa Xaa Xaa
1               5                   10                  15

Xaa Xaa Lys

<210> SEQ ID NO 19
<211> LENGTH: 16
<212> TYPE: PRT
<213> ORGANISM: Artificial sequence
<220> FEATURE:
<223> OTHER INFORMATION: Cationic peptide

<400> SEQUENCE: 19

Arg Pro Arg Tyr Pro Trp Trp Pro Trp Trp Pro Tyr Arg Pro Arg Lys
1               5                   10                  15

<210> SEQ ID NO 20
<211> LENGTH: 13
<212> TYPE: PRT
<213> ORGANISM: Artificial sequence
<220> FEATURE:
```

```
<223> OTHER INFORMATION: Cationic peptide

<400> SEQUENCE: 20

Arg Arg Ala Trp Trp Lys Ala Trp Trp Ala Arg Arg Lys
1               5                   10

<210> SEQ ID NO 21
<211> LENGTH: 14
<212> TYPE: PRT
<213> ORGANISM: Artificial sequence
<220> FEATURE:
<223> OTHER INFORMATION: Cationic peptide

<400> SEQUENCE: 21

Arg Ala Pro Tyr Trp Pro Trp Ala Trp Ala Arg Pro Arg Lys
1               5                   10

<210> SEQ ID NO 22
<211> LENGTH: 16
<212> TYPE: PRT
<213> ORGANISM: Artificial sequence
<220> FEATURE:
<223> OTHER INFORMATION: Cationic peptide

<400> SEQUENCE: 22

Arg Pro Ala Trp Lys Tyr Trp Trp Pro Trp Pro Trp Pro Arg Arg Lys
1               5                   10                  15

<210> SEQ ID NO 23
<211> LENGTH: 14
<212> TYPE: PRT
<213> ORGANISM: Artificial sequence
<220> FEATURE:
<223> OTHER INFORMATION: Cationic peptide

<400> SEQUENCE: 23

Arg Ala Ala Phe Lys Trp Ala Trp Ala Trp Trp Arg Arg Lys
1               5                   10

<210> SEQ ID NO 24
<211> LENGTH: 12
<212> TYPE: PRT
<213> ORGANISM: Artificial sequence
<220> FEATURE:
<223> OTHER INFORMATION: Cationic peptide

<400> SEQUENCE: 24

Arg Arg Arg Trp Lys Trp Ala Trp Pro Arg Arg Lys
1               5                   10

<210> SEQ ID NO 25
<211> LENGTH: 20
<212> TYPE: PRT
<213> ORGANISM: Artificial sequence
<220> FEATURE:
<223> OTHER INFORMATION: Cationic peptide
<220> FEATURE:
<221> NAME/KEY: MISC_FEATURE
<222> LOCATION: (1)..(2)
<223> OTHER INFORMATION: Xaa is R or K and one or both may be present
<220> FEATURE:
<221> NAME/KEY: MISC_FEATURE
<222> LOCATION: (3)..(3)
<223> OTHER INFORMATION: Xaa is a polar or charged amino acid (S, T, M,
      N, Q, D, E, K, R and H)
<220> FEATURE:
<221> NAME/KEY: MISC_FEATURE
<222> LOCATION: (4)..(4)
<223> OTHER INFORMATION: Xaa is C, S, M, D or A
```

```
<220> FEATURE:
<221> NAME/KEY: MISC_FEATURE
<222> LOCATION: (5)..(5)
<223> OTHER INFORMATION: Xaa is F, I, V, M or R
<220> FEATURE:
<221> NAME/KEY: MISC_FEATURE
<222> LOCATION: (6)..(7)
<223> OTHER INFORMATION: Xaa is R or K and one or both may be present
<220> FEATURE:
<221> NAME/KEY: MISC_FEATURE
<222> LOCATION: (9)..(9)
<223> OTHER INFORMATION: Xaa is C, S, M, D or A
<220> FEATURE:
<221> NAME/KEY: MISC_FEATURE
<222> LOCATION: (10)..(10)
<223> OTHER INFORMATION: Xaa is F, I, V, M or R
<220> FEATURE:
<221> NAME/KEY: MISC_FEATURE
<222> LOCATION: (13)..(13)
<223> OTHER INFORMATION: Xaa is F, I, V, M or R
<220> FEATURE:
<221> NAME/KEY: MISC_FEATURE
<222> LOCATION: (14)..(14)
<223> OTHER INFORMATION: Xaa is C, S, M, D or A
<220> FEATURE:
<221> NAME/KEY: MISC_FEATURE
<222> LOCATION: (15)..(15)
<223> OTHER INFORMATION: Xaa is F, I, V, M or R
<220> FEATURE:
<221> NAME/KEY: MISC_FEATURE
<222> LOCATION: (16)..(17)
<223> OTHER INFORMATION: Xaa is R or K and one or both may be present
<220> FEATURE:
<221> NAME/KEY: MISC_FEATURE
<222> LOCATION: (18)..(18)
<223> OTHER INFORMATION: Xaa is C, S, M, D or A
<220> FEATURE:
<221> NAME/KEY: MISC_FEATURE
<222> LOCATION: (19)..(20)
<223> OTHER INFORMATION: Xaa is R or K and one or both may be present

<400> SEQUENCE: 25

Xaa Xaa Xaa Xaa Xaa Xaa Xaa Val Xaa Xaa Arg Gly Xaa Xaa Xaa Xaa
1               5                   10                  15

Xaa Xaa Xaa Xaa
            20

<210> SEQ ID NO 26
<211> LENGTH: 19
<212> TYPE: PRT
<213> ORGANISM: Artificial sequence
<220> FEATURE:
<223> OTHER INFORMATION: Cationic peptide

<400> SEQUENCE: 26

Arg Arg Met Cys Ile Lys Val Cys Val Arg Gly Val Cys Arg Arg Lys
1               5                   10                  15

Cys Arg Lys

<210> SEQ ID NO 27
<211> LENGTH: 18
<212> TYPE: PRT
<213> ORGANISM: Artificial sequence
<220> FEATURE:
<223> OTHER INFORMATION: Cationic peptide

<400> SEQUENCE: 27

Lys Arg Ser Cys Phe Lys Val Ser Met Arg Gly Val Ser Arg Arg Arg
1               5                   10                  15

Cys Lys
```

```
<210> SEQ ID NO 28
<211> LENGTH: 19
<212> TYPE: PRT
<213> ORGANISM: Artificial sequence
<220> FEATURE:
<223> OTHER INFORMATION: Cationic peptide

<400> SEQUENCE: 28

Lys Lys Asp Ala Ile Lys Lys Val Asp Ile Arg Gly Met Asp Met Arg
1               5                   10                  15

Arg Ala Arg

<210> SEQ ID NO 29
<211> LENGTH: 18
<212> TYPE: PRT
<213> ORGANISM: Artificial sequence
<220> FEATURE:
<223> OTHER INFORMATION: Cationic peptide

<400> SEQUENCE: 29

Arg Lys Met Val Lys Val Asp Val Arg Gly Ile Met Ile Arg Lys Asp
1               5                   10                  15

Arg Arg

<210> SEQ ID NO 30
<211> LENGTH: 17
<212> TYPE: PRT
<213> ORGANISM: Artificial sequence
<220> FEATURE:
<223> OTHER INFORMATION: Cationic peptide

<400> SEQUENCE: 30

Lys Gln Cys Val Lys Val Ala Met Arg Gly Met Ala Leu Arg Arg Cys
1               5                   10                  15

Lys

<210> SEQ ID NO 31
<211> LENGTH: 20
<212> TYPE: PRT
<213> ORGANISM: Artificial sequence
<220> FEATURE:
<223> OTHER INFORMATION: Cationic peptide

<400> SEQUENCE: 31

Arg Arg Glu Ala Ile Arg Arg Val Ala Met Arg Gly Arg Asp Met Lys
1               5                   10                  15

Arg Met Arg Arg
            20

<210> SEQ ID NO 32
<211> LENGTH: 17
<212> TYPE: PRT
<213> ORGANISM: Artificial sequence
<220> FEATURE:
<223> OTHER INFORMATION: Cationic peptide
<220> FEATURE:
<221> NAME/KEY: MISC_FEATURE
<222> LOCATION: (1)..(1)
<223> OTHER INFORMATION: Xaa is R or K
<220> FEATURE:
<221> NAME/KEY: MISC_FEATURE
<222> LOCATION: (2)..(2)
<223> OTHER INFORMATION: Xaa is a polar or charged amino acid (S, T, M,
      N, Q, D, E, K, R and H)
<220> FEATURE:
<221> NAME/KEY: MISC_FEATURE
```

```
<222> LOCATION: (3)..(3)
<223> OTHER INFORMATION: Xaa is one of C, S, M, D or A
<220> FEATURE:
<221> NAME/KEY: MISC_FEATURE
<222> LOCATION: (4)..(4)
<223> OTHER INFORMATION: Xaa is one of F, I, V, M or R
<220> FEATURE:
<221> NAME/KEY: MISC_FEATURE
<222> LOCATION: (5)..(6)
<223> OTHER INFORMATION: Xaa is R or K and one or both may be present
<220> FEATURE:
<221> NAME/KEY: MISC_FEATURE
<222> LOCATION: (8)..(8)
<223> OTHER INFORMATION: Xaa is one of A, I, S, M, D or R
<220> FEATURE:
<221> NAME/KEY: MISC_FEATURE
<222> LOCATION: (9)..(9)
<223> OTHER INFORMATION: Xaa is one of F, I, V, M or R
<220> FEATURE:
<221> NAME/KEY: MISC_FEATURE
<222> LOCATION: (12)..(12)
<223> OTHER INFORMATION: Xaa is one of F, I, V, M or R
<220> FEATURE:
<221> NAME/KEY: MISC_FEATURE
<222> LOCATION: (13)..(13)
<223> OTHER INFORMATION: Xaa is one of A, I, S, M, D or R
<220> FEATURE:
<221> NAME/KEY: MISC_FEATURE
<222> LOCATION: (14)..(14)
<223> OTHER INFORMATION: Xaa is one of F, I, V, M or R
<220> FEATURE:
<221> NAME/KEY: MISC_FEATURE
<222> LOCATION: (15)..(15)
<223> OTHER INFORMATION: Xaa is R or K
<220> FEATURE:
<221> NAME/KEY: MISC_FEATURE
<222> LOCATION: (16)..(16)
<223> OTHER INFORMATION: Xaa is one of C, S, M, D or A
<220> FEATURE:
<221> NAME/KEY: MISC_FEATURE
<222> LOCATION: (17)..(17)
<223> OTHER INFORMATION: Xaa is R or K

<400> SEQUENCE: 32

Xaa Xaa Xaa Xaa Xaa Xaa Val Xaa Xaa Arg Gly Xaa Xaa Xaa Xaa Xaa
1               5                   10                  15

Xaa

<210> SEQ ID NO 33
<211> LENGTH: 18
<212> TYPE: PRT
<213> ORGANISM: Artificial sequence
<220> FEATURE:
<223> OTHER INFORMATION: Cationic peptide

<400> SEQUENCE: 33

Arg Thr Cys Val Lys Arg Val Ala Met Arg Gly Ile Ile Arg Lys Arg
1               5                   10                  15

Cys Arg

<210> SEQ ID NO 34
<211> LENGTH: 19
<212> TYPE: PRT
<213> ORGANISM: Artificial sequence
<220> FEATURE:
<223> OTHER INFORMATION: Cationic peptide

<400> SEQUENCE: 34

Lys Lys Gln Met Met Lys Arg Val Asp Val Arg Gly Ile Ser Val Lys
1               5                   10                  15

Arg Lys Arg
```

```
<210> SEQ ID NO 35
<211> LENGTH: 17
<212> TYPE: PRT
<213> ORGANISM: Artificial sequence
<220> FEATURE:
<223> OTHER INFORMATION: Cationic peptide

<400> SEQUENCE: 35

Lys Glu Ser Ile Lys Val Ile Ile Arg Gly Met Met Val Arg Met Lys
1               5                   10                  15

Lys

<210> SEQ ID NO 36
<211> LENGTH: 17
<212> TYPE: PRT
<213> ORGANISM: Artificial sequence
<220> FEATURE:
<223> OTHER INFORMATION: Cationic peptide

<400> SEQUENCE: 36

Arg Arg Asp Cys Arg Arg Val Met Val Arg Gly Ile Asp Ile Lys Ala
1               5                   10                  15

Lys

<210> SEQ ID NO 37
<211> LENGTH: 19
<212> TYPE: PRT
<213> ORGANISM: Artificial sequence
<220> FEATURE:
<223> OTHER INFORMATION: Cationic peptide

<400> SEQUENCE: 37

Lys Arg Thr Ala Ile Lys Lys Val Ser Arg Arg Gly Met Ser Val Lys
1               5                   10                  15

Ala Arg Arg

<210> SEQ ID NO 38
<211> LENGTH: 18
<212> TYPE: PRT
<213> ORGANISM: Artificial sequence
<220> FEATURE:
<223> OTHER INFORMATION: Cationic peptide

<400> SEQUENCE: 38

Arg His Cys Ile Arg Arg Val Ser Met Arg Gly Ile Ile Met Arg Arg
1               5                   10                  15

Cys Lys

<210> SEQ ID NO 39
<211> LENGTH: 31
<212> TYPE: PRT
<213> ORGANISM: Artificial sequence
<220> FEATURE:
<223> OTHER INFORMATION: Cationic peptide
<220> FEATURE:
<221> NAME/KEY: MISC_FEATURE
<222> LOCATION: (2)..(2)
<223> OTHER INFORMATION: Xaa is a polar amino acid (C, S, T, M, N and Q)
<220> FEATURE:
<221> NAME/KEY: MISC_FEATURE
<222> LOCATION: (4)..(4)
<223> OTHER INFORMATION: Xaa is one of A, L, S or K
<220> FEATURE:
<221> NAME/KEY: MISC_FEATURE
<222> LOCATION: (6)..(6)
```

```
<223> OTHER INFORMATION: Xaa is one of A, L, S or K
<220> FEATURE:
<221> NAME/KEY: MISC_FEATURE
<222> LOCATION: (11)..(11)
<223> OTHER INFORMATION: Xaa is one of A, L, S or K
<220> FEATURE:
<221> NAME/KEY: MISC_FEATURE
<222> LOCATION: (16)..(16)
<223> OTHER INFORMATION: Xaa is one of A, L, S or K
<220> FEATURE:
<221> NAME/KEY: MISC_FEATURE
<222> LOCATION: (16)..(31)
<223> OTHER INFORMATION: Xaa is amino acids chosen from G, A, V, L, I,
      P, F, S, T, K and H and one to seventeen may be present

<400> SEQUENCE: 39

Lys Xaa Lys Xaa Phe Xaa Lys Met Leu Met Xaa Ala Leu Lys Lys Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 40
<211> LENGTH: 28
<212> TYPE: PRT
<213> ORGANISM: Artificial sequence
<220> FEATURE:
<223> OTHER INFORMATION: Cationic peptide

<400> SEQUENCE: 40

Lys Cys Lys Leu Phe Lys Lys Met Leu Met Leu Ala Leu Lys Lys Val
1               5                   10                  15

Leu Thr Thr Gly Leu Pro Ala Leu Lys Leu Thr Lys
            20                  25

<210> SEQ ID NO 41
<211> LENGTH: 26
<212> TYPE: PRT
<213> ORGANISM: Artificial sequence
<220> FEATURE:
<223> OTHER INFORMATION: Cationic peptide

<400> SEQUENCE: 41

Lys Ser Lys Ser Phe Leu Lys Met Leu Met Lys Ala Leu Lys Lys Val
1               5                   10                  15

Leu Thr Thr Gly Leu Pro Ala Leu Ile Ser
            20                  25

<210> SEQ ID NO 42
<211> LENGTH: 27
<212> TYPE: PRT
<213> ORGANISM: Artificial sequence
<220> FEATURE:
<223> OTHER INFORMATION: Cationic peptide

<400> SEQUENCE: 42

Lys Thr Lys Lys Phe Ala Lys Met Leu Met Ala Leu Lys Lys Val
1               5                   10                  15

Val Ser Thr Ala Lys Pro Leu Ala Ile Leu Ser
            20                  25

<210> SEQ ID NO 43
<211> LENGTH: 32
<212> TYPE: PRT
<213> ORGANISM: Artificial sequence
<220> FEATURE:
<223> OTHER INFORMATION: Cationic peptide
```

```
<400> SEQUENCE: 43

Lys Met Lys Ser Phe Ala Lys Met Leu Met Leu Ala Leu Lys Lys Val
1               5                   10                  15

Leu Lys Val Leu Thr Thr Ala Leu Thr Leu Lys Ala Gly Leu Pro Ser
            20                  25                  30

<210> SEQ ID NO 44
<211> LENGTH: 25
<212> TYPE: PRT
<213> ORGANISM: Artificial sequence
<220> FEATURE:
<223> OTHER INFORMATION: Cationic peptide

<400> SEQUENCE: 44

Lys Asn Lys Ala Phe Ala Lys Met Leu Met Lys Ala Leu Lys Lys Val
1               5                   10                  15

Thr Thr Ala Ala Lys Pro Leu Thr Gly
            20                  25

<210> SEQ ID NO 45
<211> LENGTH: 26
<212> TYPE: PRT
<213> ORGANISM: Artificial sequence
<220> FEATURE:
<223> OTHER INFORMATION: Cationic peptide

<400> SEQUENCE: 45

Lys Gln Lys Leu Phe Ala Lys Met Leu Met Ser Ala Leu Lys Lys Lys
1               5                   10                  15

Thr Leu Val Thr Thr Pro Leu Ala Gly Lys
            20                  25

<210> SEQ ID NO 46
<211> LENGTH: 26
<212> TYPE: PRT
<213> ORGANISM: Artificial sequence
<220> FEATURE:
<223> OTHER INFORMATION: Cationic peptide
<220> FEATURE:
<221> NAME/KEY: MISC_FEATURE
<222> LOCATION: (1)..(26)
<223> OTHER INFORMATION: Xaa at residues 4, 7, 8, 10, 11,14, 15 is a
      hydrophobic amino acid
<220> FEATURE:
<221> NAME/KEY: MISC_FEATURE
<222> LOCATION: (1)..(26)
<223> OTHER INFORMATION: Xaa at residues 5, 6, 9, 12, 13 is a
      hydrophilic amino acid

<400> SEQUENCE: 46

Lys Trp Lys Xaa Xaa Xaa Xaa Xaa Xaa Xaa Xaa Xaa Xaa Xaa Xaa Ile
1               5                   10                  15

Phe His Thr Ala Leu Lys Pro Ile Ser Ser
            20                  25

<210> SEQ ID NO 47
<211> LENGTH: 26
<212> TYPE: PRT
<213> ORGANISM: Artificial sequence
<220> FEATURE:
<223> OTHER INFORMATION: Cationic peptide

<400> SEQUENCE: 47

Lys Trp Lys Ser Phe Leu Arg Thr Phe Lys Ser Pro Val Arg Thr Ile
1               5                   10                  15
```

```
Phe His Thr Ala Leu Lys Pro Ile Ser Ser
            20                  25

<210> SEQ ID NO 48
<211> LENGTH: 26
<212> TYPE: PRT
<213> ORGANISM: Artificial sequence
<220> FEATURE:
<223> OTHER INFORMATION: Cationic peptide

<400> SEQUENCE: 48

Lys Trp Lys Ser Tyr Ala His Thr Ile Met Ser Pro Val Arg Leu Ile
1               5                   10                  15

Phe His Thr Ala Leu Lys Pro Ile Ser Ser
            20                  25

<210> SEQ ID NO 49
<211> LENGTH: 26
<212> TYPE: PRT
<213> ORGANISM: Artificial sequence
<220> FEATURE:
<223> OTHER INFORMATION: Cationic peptide

<400> SEQUENCE: 49

Lys Trp Lys Arg Gly Ala His Arg Phe Met Lys Phe Leu Ser Thr Ile
1               5                   10                  15

Phe His Thr Ala Leu Lys Pro Ile Ser Ser
            20                  25

<210> SEQ ID NO 50
<211> LENGTH: 26
<212> TYPE: PRT
<213> ORGANISM: Artificial sequence
<220> FEATURE:
<223> OTHER INFORMATION: Cationic peptide

<400> SEQUENCE: 50

Lys Trp Lys Lys Trp Ala His Ser Pro Arg Lys Val Leu Thr Arg Ile
1               5                   10                  15

Phe His Thr Ala Leu Lys Pro Ile Ser Ser
            20                  25

<210> SEQ ID NO 51
<211> LENGTH: 26
<212> TYPE: PRT
<213> ORGANISM: Artificial sequence
<220> FEATURE:
<223> OTHER INFORMATION: Cationic peptide

<400> SEQUENCE: 51

Lys Trp Lys Ser Leu Val Met Met Phe Lys Lys Pro Ala Arg Arg Ile
1               5                   10                  15

Phe His Thr Ala Leu Lys Pro Ile Ser Ser
            20                  25

<210> SEQ ID NO 52
<211> LENGTH: 26
<212> TYPE: PRT
<213> ORGANISM: Artificial sequence
<220> FEATURE:
<223> OTHER INFORMATION: Cationic peptide

<400> SEQUENCE: 52

Lys Trp Lys His Ala Leu Met Lys Ala His Met Leu Trp His Met Ile
1               5                   10                  15
```

Phe His Thr Ala Leu Lys Pro Ile Ser Ser
            20                  25

<210> SEQ ID NO 53
<211> LENGTH: 26
<212> TYPE: PRT
<213> ORGANISM: Artificial sequence
<220> FEATURE:
<223> OTHER INFORMATION: Cationic peptide

<400> SEQUENCE: 53

Lys Trp Lys Ser Phe Leu Arg Thr Phe Lys Ser Pro Val Arg Thr Val
1               5                   10                  15

Phe His Thr Ala Leu Lys Pro Ile Ser Ser
            20                  25

<210> SEQ ID NO 54
<211> LENGTH: 26
<212> TYPE: PRT
<213> ORGANISM: Artificial sequence
<220> FEATURE:
<223> OTHER INFORMATION: Cationic peptide

<400> SEQUENCE: 54

Lys Trp Lys Ser Tyr Ala His Thr Ile Met Ser Pro Val Arg Leu Val
1               5                   10                  15

Phe His Thr Ala Leu Lys Pro Ile Ser Ser
            20                  25

<210> SEQ ID NO 55
<211> LENGTH: 20
<212> TYPE: DNA
<213> ORGANISM: Artificial sequence
<220> FEATURE:
<223> OTHER INFORMATION: PCR amplification primer

<400> SEQUENCE: 55
gtccctgtat gcctctggtc                                          20

<210> SEQ ID NO 56
<211> LENGTH: 19
<212> TYPE: DNA
<213> ORGANISM: Artificial sequence
<220> FEATURE:
<223> OTHER INFORMATION: PCR amplification primer

<400> SEQUENCE: 56
gatgtcacgc acgatttcc                                           19

<210> SEQ ID NO 57
<211> LENGTH: 19
<212> TYPE: DNA
<213> ORGANISM: Artificial sequence
<220> FEATURE:
<223> OTHER INFORMATION: CpG oligonucleotide

<400> SEQUENCE: 57
tcatgacgtt cctgacgtt                                           19

<210> SEQ ID NO 58
<211> LENGTH: 20
<212> TYPE: DNA
<213> ORGANISM: Artificial sequence
<220> FEATURE:
<223> OTHER INFORMATION: nonCpG oligonucleotide

```
<400> SEQUENCE: 58
ttcaggactt tcctcaggtt                                           20
```

EFFECTORS OF INNATE IMMUNITY

RELATED APPLICATION DATA

This application claims priority under 35 USC 119(e) to U.S. Patent Application Ser. No. 60/336,632, filed Dec. 3, 2001, herein incorporated by reference in its entirety.

FIELD OF THE INVENTION

The present invention relates generally to peptides and specifically to peptides effective as therapeutics and for drug discovery related to pathologies resulting from microbial infections and for modulating innate immunity or anti-inflammatory activity.

BACKGROUND OF THE INVENTION

Infectious diseases are the leading cause of death worldwide. According to a 1999 World Health Organization study, over 13 million people die from infectious diseases each year. Infectious diseases are the third leading cause of death in North America, accounting for 20% of deaths annually and increasing by 50% since 1980. The success of many medical and surgical treatments also hinges on the control of infectious diseases. The discovery and use of antibiotics has been one of the great achievements of modern medicine. Without antibiotics, physicians would be unable to perform complex surgery, chemotherapy or most medical interventions such as catheterization.

Current sales of antibiotics are US$26 billion worldwide. However, the overuse and sometimes unwarranted use of antibiotics have resulted in the evolution of new antibiotic-resistant strains of bacteria. Antibiotic resistance has become part of the medical landscape. Bacteria such as vancomycin-resistant *Enterococcus*, VRE, and methicillin-resistant *Staphylococcus aureus* and MRSA, strains cannot be treated with antibiotics and often, patients suffering from infections with such bacteria die. Antibiotic discovery has proven to be one of the most difficult areas for new drug development and many large pharmaceutical companies have cut back or completely halted their antibiotic development programs. However, with the dramatic rise of antibiotic resistance, including the emergence of untreatable infections, there is a clear unmet medical need for novel types of anti-microbial therapies, and agents that impact on innate immunity would be one such class of agents.

The innate immune system is a highly effective and evolved general defense system. Elements of innate immunity are always present at low levels and are activated very rapidly when stimulated. Stimulation can include interaction of bacterial signaling molecules with pattern recognition receptors on the surface of the body's cells or other mechanisms of disease. Every day, humans are exposed to tens of thousands of potential pathogenic microorganisms through the food and water we ingest, the air we breathe and the surfaces, pets and people that we touch. The innate immune system acts to prevent these pathogens from causing disease. The innate immune system differs from so-called adaptive immunity (which includes antibodies and antigen-specific B- and T-lymphocytes) because it is always present, effective immediately, and relatively non-specific for any given pathogen. The adaptive immune system requires amplification of specific recognition elements and thus takes days to weeks to respond. Even when adaptive immunity is pre-stimulated by vaccination, it may take three days or more to respond to a pathogen whereas innate immunity is immediately or rapidly (hours) available. Innate immunity involves a variety of effector functions including phagocytic cells, complement, etc, but is generally incompletely understood. Generally speaking many innate immune responses are "triggered" by the binding of microbial signaling molecules with pattern recognition receptors termed Toll-like receptors on the surface of host cells. Many of these effector functions are grouped together in the inflammatory response. However too severe an inflammatory response can result in responses that are harmful to the body, and in an extreme case sepsis and potentially death can occur.

The release of structural components from infectious agents during infection causes an inflammatory response, which when unchecked can lead to the potentially lethal condition, sepsis. Sepsis occurs in approximately 780,000 patients in North America annually. Sepsis may develop as a result of infections acquired in the community such as pneumonia, or it may be a complication of the treatment of trauma, cancer or major surgery. Severe sepsis occurs when the body is overwhelmed by the inflammatory response and body organs begin to fail. Up to 120,000 deaths occur annually in the United Stated due to sepsis. Sepsis may also involve pathogenic microorganisms or toxins in the blood (e.g., septicemia), which is a leading cause of death among humans. Gram-negative bacteria are the organisms most commonly associated with such diseases. However, gram-positive bacteria are an increasing cause of infections. Gram-negative and Gram-positive bacteria and their components can all cause sepsis.

The presence of microbial components induce the release of pro-inflammatory cytokines of which tumor necrosis factor$\alpha$ (TNF-$\alpha$) is of extreme importance. TNF-$\alpha$ and other pro-inflammatory cytokines can then cause the release of other pro-inflammatory mediators and lead to an inflammatory cascade. Gram-negative sepsis is usually caused by the release of the bacterial outer membrane component, lipopolysaccharide (LPS; also referred to as endotoxin). Endotoxin in the blood, called endotoxemia comes primarily from a bacterial infection, and may be released during treatment with antibiotics. Gram-positive sepsis can be caused by the release of bacterial cell wall components such as lipoteichoic acid (LTA), peptidoglycan (PG), rhamnose-glucose polymers made by *Streptococci*, or capsular polysaccharides made by *Staphylococci*. Bacterial or other non-mammalian DNA that, unlike mammalian DNA, frequently contains unmethylated cytosine-guanosine dimers (CpG DNA) has also been shown to induce septic conditions including the production of TNF-$\alpha$. Mammalian DNA contains CpG dinucleotides at a much lower frequency, often in a methylated form. In addition to their natural release during bacterial infections, antibiotic treatment can also cause release of the bacterial cell wall components LPS and LTA and probably also bacterial DNA. This can then hinder recovery from infection or even cause sepsis.

Cationic peptides are being increasingly recognized as a form of defense against infection, although the major effects recognized in the scientific and patent literature are the antimicrobial effects (Hancock, R. E. W., and R. Lehrer. 1998. Cationic peptides: a new source of antibiotics. Trends in Biotechnology 16: 82-88.). Cationic peptides having antimicrobial activity have been isolated from a wide variety of organisms. In nature, such peptides provide a defense mechanism against microorganisms such as bacteria and yeast. Generally, these cationic peptides are thought to exert their antimicrobial activity on bacteria by interacting with the cytoplasmic membrane, and in most cases, forming channels or lesions. In gram-negative bacteria, they interact with LPS to permeabilize the outer membrane, leading to self promoted uptake across the outer membrane and access to the cytoplasmic membrane. Examples of cationic antimicrobial peptides include indolicidin, defensins, cecropins, and magainins.

Recently it has been increasingly recognized that such peptides are effectors in other aspects of innate immunity (Hancock, R. E. W. and G. Diamond. 2000. The role of cationic peptides in innate host defenses. Trends in Microbiology 8:402-410.; Hancock, R. E. W. 2001. Cationic peptides: effectors in innate immunity and novel antimicrobials. Lancet Infectious Diseases 1:156-164) although it was not known if the antimicrobial and effector functions are independent.

Some cationic peptides have an affinity for binding bacterial products such as LPS and LTA. Such cationic peptides can suppress cytokine production in response to LPS, and to varying extents can prevent lethal shock. However it has not been proven as to whether such effects are due to binding of the peptides to LPS and LTA, or due to a direct interaction of the peptides with host cells. Cationic peptides are induced, in response to challenge by microbes or microbial signaling molecules like LPS, by a regulatory pathway similar to that used by the mammalian immune system (involving Toll receptors and the transcription factor; NFκB). Cationic peptides therefore appear to have a key role in innate immunity. Mutations that affect the induction of antibacterial peptides can reduce survival in response to bacterial challenge. As well, mutations of the Toll pathway of Drosophila that lead to decreased antifungal peptide expression result in increased susceptibility to lethal fungal infections. In humans, patients with specific granule deficiency syndrome, completely lacking in α-defensins, suffer from frequent and severe bacterial infections. Other evidence includes the inducibility of some peptides by infectious agents, and the very high concentrations that have been recorded at sites of inflammation. Cationic peptides may also regulate cell migration, to promote the ability of leukocytes to combat bacterial infections. For example, two human α-defensin peptides, HNP-1 and HNP-2, have been indicated to have direct chemotactic activity for murine and human T cells and monocytes, and human β-defensins appear to act as chemoattractants for immature dendritic cells and memory T cells through interaction with CCR6. Similarly, the porcine cationic peptide, PR-39 was found to be chemotactic for neutrophils. It is unclear however as to whether peptides of different structures and compositions share these properties.

The single known cathelicidin from humans, LL-37, is produced by myeloid precursors, testis, human keratinocytes during inflammatory disorders and airway epithelium. The characteristic feature of cathelicidin peptides is a high level of sequence identity at the N-terminus prepro regions termed the cathelin domain. Cathelicidin peptides are stored as inactive propeptide precursors that, upon stimulation, are processed into active peptides.

SUMMARY OF THE INVENTION

The present invention is based on the seminal discovery that based on patterns of polynucleotide expression regulated by endotoxic lipopolysaccharide, lipoteichoic acid, CpG DNA, or other cellular components (e.g., microbe or their cellular components), and affected by cationic peptides, one can screen for novel compounds that block or reduce sepsis and/or inflammation in a subject. Further, based on the use of cationic peptides as a tool, one can identify selective enhancers of innate immunity that do not trigger the sepsis reaction and that can block/dampen inflammatory and/or septic responses.

Thus, in one embodiment, a method of identifying a polynucleotide or pattern of polynucleotides regulated by one or more sepsis or inflammatory inducing agents and inhibited by a cationic peptide, is provided. The method of the invention includes contacting the polynucleotide or polynucleotides with one or more sepsis or inflammatory inducing agents and contacting the polynucleotide or polynucleotides with a cationic peptide either simultaneously or immediately thereafter. Differences in expression are detected in the presence and absence of the cationic peptide, and a change in expression, either up- or down-regulation, is indicative of a polynucleotide or pattern of polynucleotides that is regulated by a sepsis or inflammatory inducing agent and inhibited by a cationic peptide. In another aspect the invention provides a polynucleotide or polynucleotides identified by the above method. Examples of sepsis or inflammatory regulatory agents include LPS, LTA or CpG DNA or microbial components (or any combination thereof), or related agents.

In another embodiment, the invention provides a method of identifying an agent that blocks sepsis or inflammation including combining a polynucleotide identified by the method set forth above with an agent wherein expression of the polynucleotide in the presence of the agent is modulated as compared with expression in the absence of the agent and wherein the modulation in expression affects an inflammatory or septic response.

In another embodiment, the invention provides a method of identifying a pattern of polynucleotide expression for inhibition of an inflammatory or septic response by 1) contacting cells with LPS, LTA and/or CpG DNA in the presence or absence of a cationic peptide and 2) detecting a pattern of polynucleotide expression for the cells in the presence and absence of the peptide. The pattern obtained in the presence of the peptide represents inhibition of an inflammatory or septic response. In another aspect the pattern obtained in the presence of the peptide is compared to the pattern of a test compound to identify a compound that provides a similar pattern. In another aspect the invention provides a compound identified by the foregoing method.

In another embodiment, the invention provides a method of identifying an agent that enhances innate immunity by contacting a polynucleotide or polynucleotides that encode a polypeptide involved in innate immunity, with an agent of interest, wherein expression of the polynucleotide in the presence of the agent is modulated as compared with expression of the polynucleotide in the absence of the agent and wherein the modulated expression results in enhancement of innate immunity. Preferably, the agent does not stimulate a sepsis reaction in a subject. In one aspect, the agent increases the expression of an anti-inflammatory polynucleotide. Exemplary, but non-limiting anti-inflammatory polynucleotides encode proteins such as IL-1 R antagonist homolog 1 (AI1 67887), IL-10 R beta (AA486393), IL-10 R alpha (U00672) TNF Receptor member 1B (AA150416), TNF receptor member 5 (H98636), TNF receptor member 11b (AA194983), IK cytokine down-regulator of HLA II (R39227), TGF-B inducible early growth response 2 (AI473938), CD2 (AA927710), IL-19(NM_013371) or IL-10 (M57627). In one aspect, the agent decreases the expression of polynucleotides encoding proteasome subunits involved in NF-κB activation such as proteasome subunit 26S (NM_013371). In one aspect, the agent may act as an antagonist of protein kinases. In one aspect, the agent is a peptide selected from SEQ ID NO: 4-54.

In another embodiment, the invention provides a method of identifying a pattern of polynucleotide expression for identification of a compound that selectively enhances innate immunity. The invention includes detecting a pattern of polynucleotide expression for cells contacted in the presence and absence of a cationic peptide, wherein the pattern in the presence of the peptide represents stimulation of innate immunity; detecting a pattern of polynucleotide expression for cells contacted in the presence of a test compound, wherein a pattern with the test compound that is similar to the pattern observed in the presence of the cationic peptide, is indicative of a compound that enhances innate immunity. It is preferred that the compound does not stimulate a septic reaction in a subject.

In another embodiment, the invention provides a method for inferring a state of infection in a mammalian subject from a nucleic acid sample of the subject by identifying in the nucleic acid sample a polynucleotide expression pattern exemplified by an increase in polynucleotide expression of at least 2 polynucleotides in Table 50, 51 and or 52, as compared to a non-infected subject. Also included is a polynucleotide expression pattern obtained by any of the methods described above.

In another aspect a cationic peptide that is an antagonist of CXCR-4 is provided. In still another aspect, a method of identifying a cationic peptide that is an antagonist of CXCR-4 by contacting T cells with SDF-1 in the presence of absence of a test peptide and measuring chemotaxis is provided. A decrease in chemotaxis in the presence of the test peptide is indicative of a peptide that is an antagonist of CXCR-4. Cationic peptide also acts to reduce the expression of the SDF-1 receptor polynucleotide (NM_013371).

In all of the above described methods, the compounds or agents of the invention include but are not limited to peptides, cationic peptides, peptidomimetics, chemical compounds, polypeptides, nucleic acid molecules and the like.

In still another aspect the invention provides an isolated cationic peptide. An isolated cationic peptide of the invention is represented by one of the following general formulas and the single letter amino acid code:

$X_1X_2X_3IX_4PX_4IPX_5X_2X_1$ (SEQ ID NO: 4), where $X_1$ is one or two of R, L or K, $X_2$ is one of C, S or A, $X_3$ is one of R or P, $X_4$ is one of A or V and $X_5$ is one of V or W;

$X_1LX_2X_3KX_4X_2X_5X_3PX_3X_1$ (SEQ ID NO: 11), where $X_1$ is one or two of D, E, S, T or N, X2 is one or two of P, G or D, $X_3$ is one of G, A, V, L, I or Y, $X_4$ is one of R, K or H and $X_5$ is one of S, T, C, M or R;

$X_1X_2X_3X_4WX_4WX_4X_5K$ (SEQ ID NO: 18), where $X_1$ is one to four chosen from A, P or R, $X_2$ is one or two aromatic amino acids (F, Y and W), $X_3$ is one of P or K, $X_4$ is one, two or none chosen from A, P, Y or W and $X_5$ is one to three chosen from R or P;

$X_1X_2X_3X_4X_1VX_3X_4RGX_4X_3X_4X_1X_3X_1$ (SEQ ID NO: 25) where $X_1$ is one or two of R or K, $X_2$ is a polar or charged amino acid (S, T, M, N, Q, D, E, K, R and H), $X_3$ is C, S, M, D or A and X4 is F, I, V, M or R;

$X_1X_2X_3X_4X_1VX_5X_4RGX_4X_5X_4X_1X_3X_1$ (SEQ ID NO: 32), where $X_1$ is one or two of R or K, $X_2$ is a polar or charged amino acid (S, T, M, N, Q, D, E, K, R and H), $X_3$ is one of C, S, M, D or A, $X_4$ is one of F, I, V, M or R and $X_5$ is one of A, I, S, M, D or R; and $KX_1KX_2FX_2KMLMX_2ALKKX_3$ (SEQ ID NO: 39), where $X_1$ is a polar amino acid (C, S, T, M, N and Q); $X_2$ is one of A, L, S or K and $X_3$ is 1-17 amino acids chosen from G, A, V, L, I, P, F, S, T, K and H;

$KWKX_2X_1X_1X_2X_2X_1X_2X_2X_1X_1X_2X_2IFHTALKPISS$ (SEQ ID NO: 46), where $X_1$ is a hydrophobic amino acid and $X_2$ is a hydrophilic amino acid.

Additionally, in another aspect the invention provides isolated cationic peptides KWKSFLRTFKSPVRTVFHTALKPISS (SEQ ID NO: 53) and KWKSYAHTIMSPVRLVFHTALKPISS (SEQ ID NO: 54).

Also provided are nucleic acid sequences encoding the cationic peptides of the invention, vectors including such polynucleotides and host cells containing the vectors.

DETAILED DESCRIPTION OF THE INVENTION

The present invention provides novel cationic peptides, characterized by a group of generic formulas, which have ability to modulate (e.g., up- and/or down regulate) polynucleotide expression, thereby regulating sepsis and inflammatory responses and/or innate immunity.

"Innate immunity" as used herein refers to the natural ability of an organism to defend itself against invasions by pathogens. Pathogens or microbes as used herein, may include, but are not limited to bacteria, fungi, parasite, and viruses. Innate immunity is contrasted with acquired/adaptive immunity in which the organism develops a defensive mechanism based substantially on antibodies and/or immune lymphocytes that is characterized by specificity, amplifiability and self vs. non-self dsicrimination. With innate immunity, broad, nonspecific immunity is provided and there is no immunologic memory of prior exposure. The hallmarks of innate immunity are effectiveness against a broad variety of potential pathogens, independence of prior exposure to a pathogen, and immediate effectiveness (in contrast to the specific immune response which takes days to weeks to be elicited). In addition, innate immunity includes immune responses that affect other diseases, such as cancer, inflammatory diseases, multiple sclerosis, various viral infections, and the like.

As used herein, the term "cationic peptide" refers to a sequence of amino acids from about 5 to about 50 amino acids in length. In one aspect, the cationic peptide of the invention is from about 10 to about 35 amino acids in length. A peptide is "cationic" if it possesses sufficient positively charged amino acids to have a pKa greater than 9.0. Typically, at least two of the amino acid residues of the cationic peptide will be positively charged, for example, lysine or arginine. "Positively charged" refers to the side chains of the amino acid residues which have a net positive charge at pH 7.0. Examples of naturally occurring cationic antimicrobial peptides which can be recombinantly produced according to the invention include defensins, cathelicidins, magainins, melittin, and cecropins, bactenecins, indolicidins, polyphemusins, tachyplesins, and analogs thereof. A variety of organisms make cationic peptides, molecules used as part of a non-specific defense mechanism against microorganisms. When isolated, these peptides are toxic to a wide variety of microorganisms, including bacteria, fungi, and certain enveloped viruses. While cationic peptides act against many pathogens, notable exceptions and varying degrees of toxicity exist. However this patent reveals additional cationic peptides with no toxicity towards microorganisms but an ability to protect against infections through stimulation of innate immunity, and this invention is not limited to cationic peptides with antimicrobial activity. In fact, many peptides useful in the present invention do not have antimicrobial activity.

Cationic peptides known in the art include for example, the human cathelicidin LL-37, and the bovine neutrophil peptide indolicidin and the bovine variant of bactenecin, Bac2A.

LL-37       LLGDFFRKSKEKIGKEFKRIVQRIKDFLRNLVPRTES         (SEQ ID NO: 1)

Indolicidin ILPWKWPWWPWRR-NH$_2$                         (SEQ ID NO: 2)

Bac2A       RLARIVVIRVAR-NH$_2$                          (SEQ ID NO: 3)

In innate immunity, the immune response is not dependent upon antigens. The innate immunity process may include the production of secretory molecules and cellular components as set forth above. In innate immunity, the pathogens are recognized by receptors encoded in the germline. These Toll-like receptors have broad specificity and are capable of recognizing many pathogens. When cationic peptides are present in the immune response, they aid in the host response to pathogens. This change in the immune response induces the release of chemokines, which promote the recruitment of immune cells to the site of infection.

Chemokines, or chemoattractant cytokines, are a subgroup of immune factors that mediate chemotactic and other pro-inflammatory phenomena (See, Schall, 1991, *Cytokine* 3:165-183). Chemokines are small molecules of approximately 70-80 residues in length and can generally be divided into two subgroups, α which have two N-terminal cysteines separated by a single amino acid (C×C) and β which have two adjacent cysteines at the N terminus (CC). RANTES, MIP-1α and MIP-1β are members of the β subgroup (reviewed by Horuk, R., 1994, *Trends Pharmacol. Sci,* 15:159-165; Murphy, P. M., 1994, *Annu. Rev. Immunol.,* 12:593-633). The amino terminus of the β chemokines RANTES, MCP-1, and MCP-3 have been implicated in the mediation of cell migration and inflammation induced by these chemokines. This involvement is suggested by the observation that the deletion of the amino terminal 8 residues of MCP-1, amino terminal 9 residues of MCP-3, and amino terminal 8 residues of RANTES and the addition of a methionine to the amino terminus of RANTES, antagonize the chemotaxis, calcium mobilization and/or enzyme release stimulated by their native counterparts (Gong et al., 1996 *J. Biol. Chem.* 271:10521-10527; Proudfoot et al., 1996 *J. Biol. Chem.* 271:2599-2603). Additionally, a chemokine-like chemotactic activity has been introduced into MCP-1 via a double mutation of Tyr 28 and Arg 30 to leucine and valine, respectively, indicating that internal regions of this protein also play a role in regulating chemotactic activity (Beall et al., 1992, *J. Biol. Chem.* 267: 3455-3459).

The monomeric forms of all chemokines characterized thus far share significant structural homology, although the quaternary structures of α and β groups are distinct. While the monomeric structures of the β and α chemokines are very similar, the dimeric structures of the two groups are completely different. An additional chemokine, lymphotactin, which has only one N terminal cysteine has also been identified and may represent an additional subgroup (γ) of chemokines (Yoshida et al., 1995, *FEBS Lett.* 360:155-159; and Kelner et al., 1994, *Science* 266:1395-1399).

Receptors for chemokines belong to the large family of G-protein coupled, 7transmembrane domain receptors (GCR's) (See, reviews by Horuk, R., 1994, *Trends Pharmacol. Sci.* 15:159-165; and Murphy, P. M., 1994, *Annu. Rev. Immunol.* 12:593-633). Competition binding and cross-desensitization studies have shown that chemokine receptors exhibit considerable promiscuity in ligand binding. Examples demonstrating the promiscuity among β chemokine receptors include: CC CKR-1, which binds RANTES and MIP-1α (Neote et al., 1993, *Cell* 72: 415-425), CC CKR-4, which binds RANTES, MIP-1α, and MCP-1 (Power et al., 1995, *J. Biol. Chem.* 270:19495-19500), and CC CKR-5, which binds RANTES, MIP-1α, and MIP-1β (Alkhatib et al., 1996, *Science*, in press and Dragic et al., 1996, *Nature* 381: 667-674). Erythrocytes possess a receptor (known as the Duffy antigen) which binds both α and β chemokines (Horuk et al., 1994, *J. Biol. Chem.* 269:17730-17733; Neote et al., 1994, *Blood* 84:44-52; and Neote et al., 1993, *J. Biol. Chem.* 268:12247-12249). Thus the sequence and structural homologies evident among chemokines and their receptors allows some overlap in receptor-ligand interactions.

In one aspect, the present invention provides the use of compounds including cationic peptides of the invention to reduce sepsis and inflammatory responses by acting directly on host cells. In this aspect, a method of identification of a polynucleotide or polynucleotides that are regulated by one or more sepsis or inflammatory inducing agents is provided, where the regulation is altered by a cationic peptide. Such sepsis or inflammatory inducing agents include, but are not limited to endotoxic lipopolysaccharide (LPS), lipoteichoic acid (LTA) and/or CpG DNA or intact bacteria or other bacterial components. The identification is performed by contacting the polynucleotide or polynucleotides with the sepsis or inflammatory inducing agents and further contacting with a cationic peptide either simultaneously or immediately after. The expression of the polynucleotide in the presence and absence of the cationic peptide is observed and a change in expression is indicative of a polynucleotide or pattern of polynucleotides that is regulated by a sepsis or inflammatory inducing agent and inhibited by a cationic peptide. In another aspect, the invention provides a polynucleotide identified by the method.

Once identified, such polynucleotides will be useful in methods of screening for compounds that can block sepsis or inflammation by affecting the expression of the polynucleotide. Such an effect on expression may be either up regulation or down regulation of expression. By identifying compounds that do not trigger the sepsis reaction and that can block or dampen inflammatory or septic responses, the present invention also presents a method of identifying enhancers of innate immunity. Additionally, the present invention provides compounds that are used or identified in the above methods.

Candidate compounds are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, and the like to produce structural analogs. Candidate agents are also found among biomolecules including, but not limited to: peptides, peptidiomimetics, saccharides, fatty acids, steroids, purines, pyrimidines, polypeptides, polynucleotides, chemical compounds, derivatives, structural analogs or combinations thereof.

Incubating components of a screening assay includes conditions which allow contact between the test compound and the polynucleotides of interest. Contacting includes in solution and in solid phase, or in a cell. The test compound may optionally be a combinatorial library for screening a plurality of compounds. Compounds identified in the method of the invention can be further evaluated, detected, cloned, sequenced, and the like, either in solution or after binding to a solid support, by any method usually applied to the detection of a compound.

Generally, in the methods of the invention, a cationic peptide is utilized to detect and locate a polynucleotide that is essential in the process of sepsis or inflammation. Once identified, a pattern of polynucleotide expression may be obtained by observing the expression in the presence and absence of the cationic peptide. The pattern obtained in the presence of the cationic peptide is then useful in identifying additional compounds that can inhibit expression of the polynucleotide and therefore block sepsis or inflammation. It is well known to one of skill in the art that non-peptidic chemicals and peptidomimetics can mimic the ability of peptides to bind to receptors and enzyme binding sites and thus can be used to block or stimulate biological reactions. Where an additional compound of interest provides a pattern of polynucleotide expression similar to that of the expression in the presence of a cationic peptide, that compound is also useful in the modulation of sepsis or an innate immune response. In this manner, the cationic peptides of the invention, which are known inhibitors of sepsis and inflammation and enhancers of innate immunity are useful as tools in the identification of additional compounds that inhibit sepsis and inflammation and enhance innate immunity.

As can be seen in the Examples below, peptides of the invention have a widespread ability to reduce the expression of polynucleotides regulated by LPS. High levels of endotoxin in the blood are responsible for many of the symptoms seen during a serious infection or inflammation such as fever and an elevated white blood cell count. Endotoxin is a component of the cell wall of Gram-negative bacteria and is a potent trigger of the pathophysiology of sepsis. The basic mechanisms of inflammation and sepsis are related. In Example 1, polynucleotide arrays were utilized to determine the effect of cationic peptides on the transcriptional response of epithelial cells. Specifically, the effects on over 14,000 different specific polynucleotide probes induced by LPS were observed. The tables show the changes seen with cells treated with peptide compared to control cells. The resulting data indicated that the peptides have the ability to reduce the expression of polynucleotides induced by LPS.

Example 2, similarly, shows that peptides of the invention are capable of neutralizing the stimulation of immune cells by Gram positive and Gram negative bacterial products. Additionally, it is noted that certain pro-inflammatory polynucleotides are down-regulated by cationic peptides, as set forth in table 24 such as TLR1 (AI339155), TLR2 (T57791), TLR5 (N41021), TNF receptor-associated factor 2(T55353), TNF receptor-associated factor 3 (AA504259), TNF receptor superfamily, member 12 (W71984), TNF receptor superfamily, member 17 (AA987627), small inducible cytokine subfamily B, member 6 (AI889554), IL-12R beta 2 (AA977194), IL-18 receptor 1 (AA482489), while anti-inflammatory polynucleotides are up-regulated by cationic peptides, as seen in table 25 such as IL,-1 R antagonist homolog 1 (AI167887), IL-10 R beta (AA486393), TNF Receptor member 1B (AA150416), TNF receptor member 5 (H98636), TNF receptor member 11b (AA 194983), IK cytokine down-regulator of HLA II (R39227), TGF-B inducible early growth response 2 (AI473938), or CD2 (AA927710). The relevance and application of these results are confirmed by an in vivo application to mice.

In another aspect, the invention provides a method of identifying an agent that enhances innate immunity. In the method, a polynucleotide or polynucleotides that encode a polypeptide involved in innate immunity is contacted with an agent of interest. Expression of the polynucleotide is determined, both in the presence and absence of the agent. The expression is compared and of the specific modulation of expression was indicative of an enhancement of innate immunity. In another aspect, the agent does not stimulate a septic reaction as revealed by the lack of upregulation of the pro-inflammatory cytokine TNF-α. In still another aspect the agent reduces or blocks the inflammatory or septic response. In yet another aspect, the agent reduces the expression of TNF-α and/or interleukins including, but not limited to, IL-1β, IL-6, IL-12 p40, IL-12p70, and IL-8.

In another aspect, the invention provides methods of direct polynucleotide regulation by cationic peptides and the use of compounds including cationic peptides to stimulate elements of innate immunity. In this aspect, the invention provides a method of identification of a pattern of polynucleotide expression for identification of a compound that enhances innate immunity. In the method of the invention, an initial detection of a pattern of polynucleotide expression for cells contacted in the presence and absence of a cationic peptide is made. The pattern resulting from polynucleotide expression in the presence of the peptide represents stimulation of innate immunity. A pattern of polynucleotide expression is then detected in the presence of a test compound, where a resulting pattern with the test compound that is similar to the pattern observed in the presence of the cationic peptide is indicative of a compound that enhances innate immunity. In another aspect, the invention provides compounds that are identified in the above methods. In another aspect, the compound of the invention stimulates chemokine or chemokine receptor expression. Chemokine or chemokine receptors may include, but are not limited to CXCR4, CXCR1, CXCR2, CCR2, CCR4, CCR5, CCR6, MIP-1 alpha, MDC, MIP-3 alpha, MCP-1, MCP-2, MCP-3, MCP-4, MCP-5, and RANTES. In still another aspect, the compound is a peptide, peptidomimetic, chemical compound, or a nucleic acid molecule.

In still another aspect the polynucleotide expression pattern includes expression of pro-inflammatory polynucleotides. Such pro-inflammatory polynucleotides may include, but are not limited to, ring finger protein 10 (D87451), serine/threonine protein kinase MASK (AB040057), KIAA0912 protein (AB020719), KIAA0239 protein (D87076), RAP1, GTPase activating protein 1 (M64788), FEM-1-like death receptor binding protein (AB007856), cathepsin S (M90696), hypothetical protein FLJ20308 (AK000315), pim- 1 oncogene (M54915), proteasome subunit beta type 5 (D29011), KIAA0239 protein (D87076), mucin 5 subtype B tracheobronchial (AJ001403), cAMP response element-binding protein CREBPa, integrin alpha M (J03925), Rho-associated kinase 2 (NM_004850), PTD017 protein (AL050361) unknown genes (AK001143, AK034348, AL049250, AL161991, AL031983) and any combination thereof In still another aspect the polynucleotide expression pattern includes expression of cell surface receptors that may include but is not limited to retinoic acid receptor (X06614), G protein-coupled receptors (Z94155, X81892, U52219, U22491, AF015257, U66579) chemokine (C-C motif) receptor 7(L31584), tumor necrosis factor receptor superfamily member 17 (Z29575), interferon gamma receptor 2 (U05875), cytokine receptor-like factor 1 (AF059293), class I cytokine receptor (AF053004), coagulation factor II (thrombin) receptor-like 2 (U92971), leukemia inhibitory factor receptor (NM_002310), interferon gamma receptor 1 (AL050337).

In Example 4 it can be seen that the cationic peptides of the invention alter polynucleotide expression in macrophage and epithelial cells. The results of this example show that pro-inflammatory polynucleotides are down-regulated by cationic peptides (Table 24) whereas anti-inflammatory polynucleotides are up-regulated by cationic peptides (Table 25).

It is shown below, for example, in tables 1-15, that cationic peptides can neutralize the host response to the signaling molecules of infectious agents as well as modify the transcriptional responses of host cells, mainly by down-regulating the pro-inflammatory response and/or up-regulating the anti-inflammatory response. Example 5shows that the cationic peptides can aid in the host response to pathogens by inducing the release of chemokines, which promote the recruitment of immune cells to the site of infection. The results are confirmed by an in vivo application to mice.

It is seen from the examples below that cationic peptides have a substantial influence on the host response to pathogens in that they assist, in regulation of the host immune response by inducing selective pro-inflammatory responses that for example promote the recruitment of immune cells to the site of infection but not inducing potentially harmful pro-inflammatory cytokines. Sepsis appears to be caused in part by an overwhelming pro-inflammatory response to infectious agents. Cationic peptides aid the host in a "balanced" response to pathogens by inducing an anti-inflammatory response and suppressing certain potentially harmful pro-inflammatory responses.

In Example 7, the activation of selected MAP kinases was examined, to study the basic mechanisms behind the effects of interaction of cationic peptides with cells. Macrophages activate MEK/ERK kinases in response to bacterial infection. MEK is a MAP kinase kinase that when activated, phosphorylates the downstream kinase ERK (extracellular regulated kinase), which then dimerizes and translocates to the nucleus where it activates transcription factors such as Elk-1 to modify polynucleotide expression. MEK/ERK kinases have been shown to impair replication of Salmonella within macrophages. Signal transduction by MEK kinase and NADPH oxidase may play an important role in innate host defense against intracellular pathogens. By affecting the MAP kinases as shown below the cationic peptides have an effect on bacterial infection. The cationic peptides can directly affect kinases. Table 21 demonstrates but is not limited to MAP kinase polynucleotide expression changes in response to peptide. The kinases include MAP kinase kinase 6 (H070920), MAP kinase kinase 5 (W69649), MAP kinase 7(H39192), MAP kinase 12 (AI936909) and MAP kinase-activated protein kinase 3(W68281).

In another method, the methods of the invention may be used in combination, to identify an agent with multiple characteristics, i.e. a peptide with anti-inflammatory/anti-sepsis activity, and the ability to enhance innate immunity, in part by inducing chemokines in vivo.

In another aspect, the invention provides a method for inferring a state of infection in a mammalian subject from a nucleic acid sample of the subject by identifying in the nucleic acid sample a polynucleotide expression pattern exemplified by an increase in polynucleotide expression of at least 2 polynucleotides in Table 55 as compared to a non-infected subject. In another aspect the invention provides a method for inferring a state of infection in a mammalian subject from a nucleic acid sample of the subject by identifying in the nucleic acid sample a polynucleotide expression pattern exemplified by a polynucleotide expression of at least 2 polynucleotides in Table 56 or Table 57 as compared to a non-infected subject. In one aspect of the invention, the state of infection is due to infectious agents or signaling molecules derived therefrom, such as, but not limited to, Gram negative bacteria and Gram positive bacteria, viral, fungal or parasitic agents. In still another aspect the invention provides a polynucleotide expression pattern of a subject having a state of infection identified by the above method. Once identified, such polynucleotides will be useful in methods of diagnosis of a condition associated with the activity or presence of such infectious agents or signaling molecules.

Example 10 below demonstrates this aspect of the invention. Specifically, table 61 demonstrates that both MEK and the NADPH oxidase inhibitors can limit bacterial replication (infection of IFN-γ-primed macrophages by S. typhimurium triggers a MEK kinase). This is an example of how bacterial survival can be impacted by changing host cell signaling molecules.

In still another aspect of the invention, compounds are presented that inhibit stromal derived factor-1 (SDF-1) induced chemotaxis of T cells. Compounds are also presented which decrease expression of SDF-1 receptor. Such compounds also may act as an antagonist or inhibitor of CXCR-4. In one aspect the invention provides a cationic peptide that is an antagonist of CXCR-4. In another aspect the invention provides a method of identifying a cationic peptide that is an antagonist of CXCR-4. The method includes contacting T cells with SDF-1 in the presence of absence of a test peptide and measuring chemotaxis. A decrease in chemotaxis in the presence of the test peptide is then indicative of a peptide that is an antagonist of CXCR-4. Such compounds and methods are useful in therapeutic applications in HIV patients. These types of compounds and the utility thereof is demonstrated, for example, in Example 11 (see also Tables 62, 63). In that example, cationic peptides are shown to inhibit cell migration and therefore antiviral activity.

In one embodiment, the invention provides an isolated cationic peptides having an amino acid sequence of the general formula (Formula A): $X_1X_2X_3IX_4PX_4IPX_5X_2X_1$ (SEQ ID NO: 4), wherein $X_1$ is one or two of R, L or K, $X_2$ is one of C, S or A, $X_3$ is one of R or P, $X_4$ is one of A or V and $X_5$ is one of V or W. Examples of the peptides of the invention include, but are not limited to: LLCRIVPVIPWCK (SEQ ID NO: 5), LRCPIAPVIPVCKK (SEQ ID NO: 6), KSRIVPAIPVSLL (SEQ ID NO: 7), KKSPIAPAIPWSR (SEQ ID NO: 8), RRARIVPAIPVARR (SEQ ID NO: 9) and LSRIAPAIP-WAKL (SEQ ID NO: 10).

In another embodiment, the invention provides an isolated linear cationic peptide having an amino acid sequence of the general formula (Formula B): $X_1LX_2X_3KX_4X_2X_5X_3PX_3X_1$ (SEQ ID NO: 11), wherein $X_1$ is one or two of D, E, S, T or N, X2 is one or two of P, G or D, $X_3$ is one of G, A, V, L, I or Y, $X_4$ is one of R, K or H and $X_5$ is one of S, T, C, M or R. Examples of the peptides of the invention include, but are not limited to: DLPAKRGSAPGST (SEQ ID NO: 12), SELPGLKHPCVPGS (SEQ ID NO: 13), TTLGPVKRD-SIPGE (SEQ ID NO: 14), SLPIKHDRLPATS (SEQ ID NO: 15), ELPLKRGRVPVE (SEQ ID NO: 16) and NLP-DLKKPRVPATS (SEQ ID NO: 17).

In another embodiment, the invention provides an isolated linear cationic peptide having an amino acid sequence of the general formula (Formula C): $X_1X_2X_3X_4WX_4WX_4X_5K$ (SEQ ID NO: 18) (this formula includes CP12a and CP12d), wherein $X_1$ is one to four chosen from A, P or R, $X_2$ is one or two aromatic amino acids (F, Y and W), $X_3$ is one of P or K, $X_4$ is one, two or none chosen from A, P, Y or W and $X_5$ is one to three chosen from R or P. Examples of the peptides of the invention include, but are not limited to: RPRYPWWPWW-PYRPRK (SEQ ID NO: 19), RRAWWKAWWARRK (SEQ ID NO: 20), RAPYWPWAWARPRK (SEQ ID NO: 21), RPAWKYWWPWPWPRRK (SEQ ID NO: 22), RAAFK-WAWAWWRRK (SEQ ID NO: 23) and RRRWKWAW-PRRK (SEQ ID NO: 24).

In another embodiment, the invention provides an isolated hexadecameric cationic peptide having an amino acid sequence of the general formula (Formula D): $X_1X_2X_3X_4X_1VX_3X_4RGX_4X_3X_4X_1X_3X_1$ (SEQ ID NO: 25) wherein $X_1$ is one or two of R or K, $X_2$ is a polar or charged amino acid (S, T, M, N, Q, D, E, K, R and H), $X_3$ is C, S, M, D or A and $X_4$ is F, I, V, M or R. Examples of the peptides of the invention include, but are not limited to: RRM-CIKVCVRGVCRRKCRK (SEQ ID NO: 26), KRSCFKVSMRGVSRRRCK (SEQ ID NO: 27), KKDAIKKVDIRGMDMRRAR (SEQ ID NO: 28), RKM-VKVDVRGIMIRKDRR (SEQ ID NO: 29), KQCVKVAM-RGMALRRCK (SEQ ID NO: 30) and RREAIRRVAMR-GRDMKRMRR (SEQ ID NO: 31).

In still another embodiment, the invention provides an isolated hexadecameric cationic peptide having an amino acid sequence of the general formula (Formula E): $X_1X_2X_3X_4X_1VX_5X_4RGX_4X_5X_4X_1X_3X_1$ (SEQ ID NO: 32), wherein $X_1$ is one or two of R or K, $X_2$ is a polar or charged amino acid (S, T, M, N, Q, D, E, K, R and H), $X_3$ is one of C, S, M, D or A, $X_4$ is one of F, I, V, M or R and $X_5$ is one of A, I, S, M, D or R. Examples of the peptides of the invention include, but are not limited to: RTCVKRVAMRGIIRKRCR (SEQ ID NO: 33), KKQMMKRVDVRGISVKRKR (SEQ ID NO: 34), KESIKVIIRGMMVRMKK (SEQ ID NO: 35), RRDCRRVMVRGIDIKAK (SEQ ID NO: 36), KRTAIKKVSRRGMSVKARR (SEQ ID NO: 37) and RHCIRRVSMRGIIMRRCK (SEQ ID NO: 38).

In another embodiment, the invention provides an isolated longer cationic peptide having an amino acid sequence of the general formula (Formula F): $KX_1KX_2FX_2KMLMX_2ALKKX_3$ (SEQ ID NO: 39), wherein $X_1$ is a polar amino acid (C, S, T, M, N and Q); $X_2$ is one of A, L, S or K and $X_3$ is 1-17 amino acids chosen from G, A, V, L, I, P, F, S, T, K and H. Examples of the peptides of the invention include, but are not limited to: KCKLFKKMLMLALKKV-LTTGLPALKLTK (SEQ ID NO: 40), KSKSFLKM-LMKALKKVLTTGLPALIS (SEQ ID NO: 41), KTKKFAK-MLMMALKKVVSTAKPLAILS (SEQ ID NO: 42), KMKSFAKMLMLALKKVLKVLTTALTLKAGLPS (SEQ ID NO: 43), KNKAFAKMLMKALKKVTTAAKPLTG (SEQ ID NO: 44) and KQKLFAKMLMSALKKKTLVT-TPLAGK (SEQ ID NO: 45).

In yet another embodiment, the invention provides an isolated longer cationic peptide having an amino acid sequence of the general formula (Formula G): $KWKX_2X_1X_1X_2X_2X_1X_2X_2X_1X_1X_2X_2IFHTALKPISS$ (SEQ ID NO: 46), wherein $X_1$ is a hydrophobic amino acid and $X_2$ is a hydrophilic amino acid. Examples of the peptides of the invention include, but are not limited to: KWKSFLRT-FKSPVRTIFHTALKPISS (SEQ ID NO: 47), KWKSYAHTIMSPVRLIFHTALKPISS (SEQ ID NO: 48), KWKRGAHRFMKFLSTIFHTALKPISS (SEQ ID NO: 49), KWKKWAHSPRKVLTRIFHTALKPISS (SEQ ID NO: 50), KWKSLVMMFKKPARRIFHTALKPISS (SEQ ID NO: 51) and KWKHALMKAHMLWHMIFHTALKPISS (SEQ ID NO: 52).

In still another embodiment, the invention provides an isolated cationic peptide having an amino acid sequence of the formula: KWKSFLRTFKSPVRTVFHTALKPISS (SEQ ID NO: 53) or KWKSYAHTIMSPVRLVFHTALKPISS (SEQ ID NO: 54).

The term "isolated" as used herein refers to a peptide that is substantially free of other proteins, lipids, and nucleic acids (e.g., cellular components with which an in vivo-produced peptide would naturally be associated). Preferably, the peptide is at least 70%, 80%, or most preferably 90% pure by weight.

The invention also includes analogs, derivatives, conservative variations, and cationic peptide variants of the enumerated polypeptides, provided that the analog, derivative, conservative variation, or variant has a detectable activity in which it enhances innate immunity or has anti-inflammatory activity. It is not necessary that the analog, derivative, variation, or variant have activity identical to the activity of the peptide from which the analog, derivative, conservative variation, or variant is derived.

A cationic peptide "variant" is an peptide that is an altered form of a referenced cationic peptide. For example, the term "variant" includes a cationic peptide in which at least one amino acid of a reference peptide is substituted in an expression library. The term "reference" peptide means any of the cationic peptides of the invention (e.g., as defined in the above formulas), from which a variant, derivative, analog, or conservative variation is derived. Included within the term "derivative" is a hybrid peptide that includes at least a portion of each of two cationic peptides (e.g., 30-80% of each of two cationic peptides). Also included are peptides in which one or more amino acids are deleted from the sequence of a peptide enumerated herein, provided that the derivative has activity in which it enhances innate immunity or has anti-inflammatory activity. This can lead to the development of a smaller active molecule which would also have utility. For example, amino or carboxy terminal amino acids which may not be required for enhancing innate immunity or anti-inflammatory activity of a peptide can be removed. Likewise, additional derivatives can be produced by adding one or a few (e.g., less than 5) amino acids to a cationic peptide without completely inhibiting the activity of the peptide. In addition, C-terminal derivatives, e.g., C-terminal methyl esters, and N-terminal derivatives can be produced and are encompassed by the invention. Peptides of the invention include any analog, homolog, mutant, isomer or derivative of the peptides disclosed in the present invention, so long as the bioactivity as described herein remains. Also included is the reverse sequence of a peptide encompassed by the general formulas set forth above. Additionally, an amino acid of "D" configuration may be substituted with an amino acid of "L" configuration and vice versa. Alternatively the peptide may be cyclized chemically or by the addition of two or more cysteine residues within the sequence and oxidation to form disulphide bonds.

The invention also includes peptides that are conservative variations of those peptides exemplified herein. The term "conservative variation" as used herein denotes a polypeptide in which at least one amino acid is replaced by another, biologically similar residue. Examples of conservative variations include the substitution of one hydrophobic residue, such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acid, or glutamine for asparagine, and the like. Neutral hydrophilic amino acids that can be substituted for one another include asparagine, glutamine, serine and threonine. The term "conservative variation" also encompasses a peptide having a substituted amino acid in place of an unsubstituted parent amino acid. Such substituted amino acids may include amino acids that have been methylated or amidated. Other substitutions will be known to those of skill in the art. In one aspect, antibodies raised to a substituted polypeptide will also specifically bind the unsubstituted polypeptide.

Peptides of the invention can be synthesized by commonly used methods such as those that include t-BOC or FMOC protection of alpha-amino groups. Both methods involve stepwise synthesis in which a single amino acid is added at each step starting from the C-terminus of the peptide (See, Coligan, et al., *Current Protocols in Immunology*, Wiley Interscience, 1991, Unit 9). Peptides of the invention can also be synthesized by the well known solid phase peptide synthesis methods such as those described by Merrifield, *J. Am. Chem. Soc.*, 85:2149, 1962) and Stewart and Young, *Solid Phase Peptides Synthesis*, Freeman, San Francisco, 1969, pp.27-62) using a copoly(styrene-divinylbenzene) containing 0.1-1.0 mMol amines/g polymer. On completion of chemical synthesis, the peptides can be deprotected and cleaved from the polymer by treatment with liquid HF-10% anisole for about ¼-1 hours at 0° C. After evaporation of the reagents, the peptides are extracted from the polymer with a 1% acetic acid solution, which is then lyophilized to yield the crude material. The peptides can be purified by such techniques as gel filtration on Sephadex G-15 using 5% acetic acid as a solvent. Lyophilization of appropriate fractions of the column eluate yield homogeneous peptide, which can then be characterized by standard techniques such as amino acid analysis, thin layer chromatography, high performance liquid chromatography, ultraviolet absorption spectroscopy, molar rotation, or measuring solubility. If desired, the peptides can be quantitated by the solid phase Edman degradation.

The invention also includes isolated nucleic acids (e.g., DNA, cDNA, or RNA) encoding the peptides of the invention. Included are nucleic acids that encode analogs, mutants, conservative variations, and variants of the peptides described herein. The term "isolated" as used herein refers to a nucleic acid that is substantially free of proteins, lipids, and other nucleic acids with which an in vivo-produced nucleic acids naturally associated. Preferably, the nucleic acid is at least 70%, 80%, or preferably 90% pure by weight, and conventional methods for synthesizing nucleic acids in vitro can be used in lieu of in vivo methods. As used,herein, "nucleic acid" refers to a polymer of deoxyribo-nucleotides or ribonucleotides, in the form of a separate fragment or as a component of a larger genetic construct (e.g., by operably linking a promoter to a nucleic acid encoding a peptide of the invention). Numerous genetic constructs (e.g., plasmids and other expression vectors) are known in the art and can be used to produce the peptides of the invention in cell-free systems or prokaryotic or eukaryotic (e.g., yeast, insect, or mammalian) cells. By taking into account the degeneracy of the genetic code, one of ordinary skill in the art can readily synthesize nucleic acids encoding the polypeptides of the invention. The nucleic acids of the invention can readily be used in conventional molecular biology methods to produce the peptides of the invention.

DNA encoding the cationic peptides of the invention can be inserted into an "expression vector." The term "expression vector" refers to a genetic construct such as a plasmid, virus or other vehicle known in the art that can be engineered to contain a nucleic acid encoding a polypeptide of the invention. Such expression vectors are preferably plasmids that contain a promoter sequence that facilitates transcription of the inserted genetic sequence in a host cell. The expression vector typically contains an origin of replication, and a promoter, as well as polynucleotides that allow phenotypic selection of the transformed cells (e.g., an antibiotic resistance polynucleotide). Various promoters, including inducible and constitutive promoters, can be utilized in the invention. Typically, the expression vector contains a replicon site and control sequences that are derived from a species compatible with the host cell.

Transformation or transfection of a recipient with a nucleic acid of the invention can be carried out using conventional techniques well known to those skilled in the art. For example, where the host cell is *E. coli*, competent cells that are capable of DNA uptake can be prepared using the $CaCl_2$, $MgCl_2$ or RbCl methods known in the art. Alternatively, physical means, such as electroporation or microinjection can be used. Electroporation allows transfer of a nucleic acid into a cell by high voltage electric impulse. Additionally, nucleic acids can be introduced into host cells by protoplast fusion, using methods well known in the art. Suitable methods for transforming eukaryotic cells, such as electroporation and lipofection, also are known.

"Host cells" or "Recipient cells" encompassed by of the invention are any cells in which the nucleic acids of the invention can be used to express the polypeptides of the invention. The term also includes any progeny of a recipient or host cell. Preferred recipient or host cells of the invention include *E. coli, S. aureuis* and *P. aeruginosa*, although other Gram-negative and Gram-positive bacterial, fungal and mammalian cells and organisms known in the art can be utilized as long as the expression vectors contain an origin of replication to permit expression in the host.

The cationic peptide polynucleotide sequence used according to the method of the invention can be isolated from an organism or synthesized in the laboratory. Specific DNA sequences encoding the cationic peptide of interest can be obtained by: 1) isolation of a double-stranded DNA sequence from the genomic DNA; 2) chemical manufacture of a DNA sequence to provide the necessary codons for the cationic peptide of interest; and 3) in vitro synthesis of a double-stranded DNA sequence by reverse transcription of mRNA isolated from a donor cell. In the latter case, a double-stranded DNA complement of MRNA is eventually formed which is generally referred to as cDNA.

The synthesis of DNA sequences is frequently the method of choice when the entire sequence of amino acid residues of the desired peptide product is known. In the present invention, the synthesis of a DNA sequence has the advantage of allowing the incorporation of codons which are more likely to be recognized by a bacterial host, thereby permitting high level expression without difficulties in translation. In addition, virtually any peptide can be synthesized, including those encoding natural cationic peptides, variants of the same, or synthetic peptides.

When the entire sequence of the desired peptide is not known, the direct synthesis of DNA sequences is not possible and the method of choice is the formation of cDNA sequences. Among the standard procedures for isolating cDNA sequences of interest is the formation of plasmid or phage containing cDNA libraries which are derived from reverse transcription of MRNA which is abundant in donor cells that have a high level of genetic expression. When used in combination with polymerase chain reaction technology, even rare expression products can be cloned. In those cases where significant portions of the amino acid sequence of the cationic peptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single stranded form (Jay, et al., Nuc. Acid Res., 11:2325, 1983).

The peptide of the invention can be administered parenterally by injection or by gradual infusion over time. The peptide can be administered intravenously, intraperitoneally, intramuscularly, subcutaneously, intracavity, or transdermally. Preferred methods for delivery of the peptide include orally, by encapsulation in microspheres or proteinoids, by aerosol delivery to the lungs, or transdermally by iontophoresis or transdermal electroporation. Other methods of administration will be known to those skilled in the art.

Preparations for parenteral administration of a peptide of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention will now be described in greater detail by reference to the following non-limiting examples. While the invention has been described in detail with reference to certain preferred embodiments thereof, it will be understood that modifications and variations are within the spirit and scope of that which is described and claimed.

EXAMPLE 1

Anti-Sepsis/Anti-Inflammatory Activity

Polynucleotide arrays were utilized to determine the effect of cationic peptides on the transcriptional response of epithelial cells. The A549 human epithelial cell line was maintained in DMEM (Gibco) supplemented with 10% fetal bovine serum (FBS, Medicorp). The A549 cells were plated in 100 mm tissue culture dishes at $2.5 \times 10^6$ cells/dish, cultured overnight and then incubated with 100 ng/ml E. coli O111: B4 LPS (Sigma), without (control) or with 50 µg/ml peptide or medium alone for 4 h. After stimulation, the cells were washed once with diethyl pyrocarbonate-treated phosphate buffered saline (PBS), and detached from the dish using a cell scraper. Total RNA was isolated using RNAqueous (Ambion, Austin, Tex.). The RNA pellet was resuspended in RNase-free water containing Superase-In (RNase inhibitor; Ambion). DNA contamination was removed with DNA-free kit, Ambion). The quality of the RNA was assessed by gel electrophoresis on a 1% agarose gel.

The polynucleotide arrays used were the Human Operon arrays (identification number for the genome is PRHU04-S1), which consist of about 14,000 human oligos spotted in duplicate. Probes were prepared from 10 µg of total RNA and labeled with Cy3 or Cy5 labeled dUTP. The probes were purified and hybridized to printed glass slides overnight at 42° C. and washed. After washing, the image was captured using a Perkin Elmer array scanner. The image processing software (Imapolynucleotide 5.0, Marina Del Rey, Calif.) determines the spot mean intensity, median intensities, and background intensities. A "homemade" program was used to remove background. The program calculates the bottom 10% intensity for each subgiid and subtracts this for each grid. Analysis was performed with Genespring software (Redwood City, Calif.). The intensities for each spot were normalized by taking the median spot intensity value from the population of spot values within a slide and comparing this value to the values of all slides in the experiment. The relative changes seen with cells treated with peptide compared to control cells can be found in Tables 1 and 2. These tables 2 reflect only those polynucleotides that demonstrated significant changes in expression of the 14,000polynucleotides that were tested for altered expression. The data indicate that the peptides have a widespread ability to reduce the expression of polynucleotides that were induced by LPS.

In Table 1, the peptide, SEQ ID NO: 27 is shown to potently reduce the expression of many of the polynucleotides up-regulated by E. coli O111:B4 LPS as studied by polynucleotide microarrays. Peptide (50 µg/ml) and LPS (0.1 µg/ml) or LPS alone was incubated with the A549 cells for 4 h and the RNA was isolated. Five µg total RNA was used to make Cy3/Cy5 labeled cDNA probes and hybridized onto Human Operon arrays (PRHU04). The intensity of unstimulated cells is shown in the third column of Table 1. The "Ratio: LPS/control" column refers to the intensity of polynucleotide expression in LPS simulated cells divided by in the intensity of unstimulated cells. The "Ratio: LPS+ID 27/control" column refers to the intensity of polynucleotide expression in cells stimulated with LPS and peptide divided by unstimulated cells.

TABLE 1

Reduction, by peptide SEQ ID 27, of A549 human epithelial cell polynucleotide expression up-regulated by E. coli O111:B4 LPS

| Accession Number[a] | Polynucleotide Gene Function | Control: Media only Intensity | Ratio: LPS/control | Ratio: LPS + ID 27/control |
|---|---|---|---|---|
| AL031983 | Unknown | 0.032 | 302.8 | 5.1 |
| L04510 | ADP-ribosylation factor | 0.655 | 213.6 | 1.4 |
| D87451 | ring finger protein 10 | 3.896 | 183.7 | 2.1 |

TABLE 1-continued

Reduction, by peptide SEQ ID 27, of A549 human epithelial cell polynucleotide expression up-regulated by *E. coli* O111:B4 LPS

| Accession Number[a] | Polynucleotide Gene Function | Control: Media only Intensity | Ratio: LPS/control | Ratio: LPS + ID 27/control |
|---|---|---|---|---|
| AK000869 | hypothetical protein | 0.138 | 120.1 | 2.3 |
| U78166 | Ric-like expressed in neurons | 0.051 | 91.7 | 0.2 |
| AJ001403 | mucin 5 subtype B tracheobronchial | 0.203 | 53.4 | 15.9 |
| AB040057 | serine/threonine protein kinase MASK | 0.95 | 44.3 | 15.8 |
| Z99756 | Unknown | 0.141 | 35.9 | 14.0 |
| L42243 | interferon receptor 2 | 0.163 | 27.6 | 5.2 |
| NM_016216 | RNA lariat debranching enzyme | 6.151 | 22.3 | 10.9 |
| AK001589 | hypothetical protein | 0.646 | 19.2 | 1.3 |
| AL137376 | Unknown | 1.881 | 17.3 | 0.6 |
| AB007856 | FEM-1-like death receptor binding protein | 2.627 | 15.7 | 0.6 |
| AB007854 | growth arrest-specific 7 | 0.845 | 14.8 | 2.2 |
| AK000353 | cytosolic ovarian carcinoma antigen 1 | 0.453 | 13.5 | 1.0 |
| D14539 | myeloid/lymphoid or mixed-lineage leukemia translocated to 1 | 2.033 | 11.6 | 3.1 |
| X76785 | integration site for Epstein-Barr virus | 0.728 | 11.6 | 1.9 |
| M54915 | pim-1 oncogene | 1.404 | 11.4 | 0.6 |
| NM_006092 | caspase recruitment domain 4 | 0.369 | 11.0 | 0.5 |
| J03925 | integrin_alpha M | 0.272 | 9.9 | 4.2 |
| NM_001663 | ADP-ribosylation factor 6 | 0.439 | 9.7 | 1.7 |
| M23379 | RAS p21 protein activator | 0.567 | 9.3 | 2.8 |
| K02581 | thymidine kinase 1 soluble | 3.099 | 8.6 | 3.5 |
| U94831 | transmembrane 9 superfamily member 1 | 3.265 | 7.1 | 1.5 |
| X70394 | zinc finger protein 146 | 1.463 | 6.9 | 1.7 |
| AL137614 | hypothetical protein | 0.705 | 6.8 | 1.0 |
| U43083 | guanine nucleotide binding protein | 0.841 | 6.6 | 1.6 |
| AL137648 | DKFZp434J1813 protein | 1.276 | 6.5 | 0.8 |
| AF085692 | ATP-binding cassette sub-family C (CFTR/MRP) member 3 | 3.175 | 6.5 | 2.4 |
| AK001239 | hypothetical protein FLJ10377 | 2.204 | 6.4 | 1.3 |

TABLE 1-continued

Reduction, by peptide SEQ ID 27, of A549 human epithelial cell polynucleotide expression up-regulated by *E. coli* O111:B4 LPS

| Accession Number[a] | Polynucleotide Gene Function | Control: Media only Intensity | Ratio: LPS/control | Ratio: LPS + ID 27/control |
|---|---|---|---|---|
| NM_001679 | ATPase Na+/K+ transporting beta 3 polypeptide | 2.402 | 6.3 | 0.9 |
| L24804 | unactive progesterone receptor | 3.403 | 6.1 | 1.1 |
| U15932 | dual specificity phosphatase 5 | 0.854 | 6.1 | 2.1 |
| M36067 | ligase I DNA_ATP-dependent | 1.354 | 6.1 | 2.2 |
| AL161951 | Unknown | 0.728 | 5.8 | 1.9 |
| M59820 | colony stimulating factor 3 receptor | 0.38 | 5.7 | 2.0 |
| AL050290 | spermidine/spermine N1-acetyltransferase | 2.724 | 5.6 | 1.4 |
| NM_002291 | laminin_beta 1 | 1.278 | 5.6 | 1.8 |
| X06614 | retinoic acid receptor_alpha | 1.924 | 5.5 | 0.8 |
| AB007896 | putative L-type neutral amino acid transporter | 0.94 | 5.3 | 1.8 |
| AL050333 | DKFZP564B11 6 protein | 1.272 | 5.3 | 0.6 |
| AK001093 | hypothetical protein | 1.729 | 5.3 | 2.0 |
| NM_016406 | hypothetical protein | 1.314 | 5.2 | 1.2 |
| M86546 | pre-B-cell leukemia transcription factor 1 | 1.113 | 5.2 | 2.2 |
| X56777 | zona pellucida glycoprotein 3A | 1.414 | 5.0 | 1.4 |
| NM_013400 | replication initiation region protein | 1.241 | 4.9 | 2.0 |
| NM_002309 | leukemia inhibitory factor | 1.286 | 4.8 | 1.9 |
| NM_001940 | dentatorubral-pallidoluysian atrophy | 2.034 | 4.7 | 1.2 |
| U91316 | cytosolic acyl coenzyme A thioester hydrolase | 2.043 | 4.7 | 1.4 |
| X76104 | death-associated protein kinase 1 | 1.118 | 4.6 | 1.8 |
| AF131838 | Unknown | 1.879 | 4.6 | 1.4 |
| AL050348 | Unknown | 8.502 | 4.4 | 1.7 |
| D42085 | KIAA0095 gene product | 1.323 | 4.4 | 1.2 |
| X92896 | Unknown | 1.675 | 4.3 | 1.5 |
| U26648 | syntaxin 5A | 1.59 | 4.3 | 1.4 |
| X85750 | monocyte to macrophage differentiation-associated | 1.01 | 4.3 | 1.1 |
| D14043 | CD164 antigen_sialomucin | 1.683 | 4.2 | 1.0 |
| J04513 | fibroblast growth factor 2 | 1.281 | 4.0 | 0.9 |
| U19796 | melanoma-associated antigen | 1.618 | 4.0 | 0.6 |

TABLE 1-continued

Reduction, by peptide SEQ ID 27, of A549 human epithelial cell polynucleotide expression up-regulated by *E. coli* O111:B4 LPS

| Accession Number[a] | Polynucleotide Gene Function | Control: Media only Intensity | Ratio: LPS/control | Ratio: LPS + ID 27/control |
|---|---|---|---|---|
| AK000087 | hypothetical protein | 1.459 | 3.9 | 1.0 |
| AK001569 | hypothetical protein | 1.508 | 3.9 | 1.2 |
| AF189009 | ubiquilin 2 | 1.448 | 3.8 | 1.3 |
| U60205 | sterol-C4-methyl oxidase-like | 1.569 | 3.7 | 0.8 |
| AK000562 | hypothetical protein | 1.166 | 3.7 | 0.6 |
| AL096739 | Unknown | 3.66 | 3.7 | 0.5 |
| AK000366 | hypothetical protein | 15.192 | 3.5 | 1.0 |
| NM_006325 | RAN member RAS oncogene family | 1.242 | 3.5 | 1.4 |
| X51688 | cyclin A2 | 1.772 | 3.3 | 1.0 |
| U34252 | aldehyde dehydrogenase 9 | 1.264 | 3.3 | 1.2 |
| NM_013241 | FH1/FH2 domain-containing protein | 1.264 | 3.3 | 0.6 |
| AF112219 | esterase D/formylglutathione hydrolase | 1.839 | 3.3 | 1.1 |
| NM_016237 | anaphase-promoting complex subunit 5 | 2.71 | 3.2 | 0.9 |
| AB014569 | KIAA0669 gene product | 2.762 | 3.2 | 0.2 |
| AF151047 | hypothetical protein | 3.062 | 3.1 | 1.0 |
| X92972 | protein phosphatase 6 catalytic subunit | 2.615 | 3.1 | 1.1 |
| AF035309 | proteasome 26S subunit ATPase 5 | 5.628 | 3.1 | 1.3 |
| U52960 | SRB7 homolog | 1.391 | 3.1 | 0.8 |
| J04058 | electron-transfer-flavoprotein alpha polypeptide | 3.265 | 3.1 | 1.2 |
| M57230 | interleukin 6 signal transducer | 0.793 | 3.1 | 1.0 |
| U78027 | galactosidase_alpha | 3.519 | 3.1 | 1.1 |
| AK000264 | Unknown | 2.533 | 3.0 | 0.6 |
| X80692 | mitogen-activated protein kinase 6 | 2.463 | 2.9 | 1.3 |
| L25931 | lamin B receptor | 2.186 | 2.7 | 0.7 |
| X13334 | CD14 antigen | 0.393 | 2.5 | 1.1 |
| M32315 | tumor necrosis factor receptor superfamily member 1B | 0.639 | 2.4 | 0.4 |
| NM_004862 | LPS-induced TNF-alpha factor | 6.077 | 2.3 | 1.1 |
| AL050337 | interferon gamma receptor 1 | 2.064 | 2.1 | 1.0 |

[a]All Accession Numbers in Table 1 through Table 64 refer to GenBank Accession Numbers.

In Table 2, the cationic peptides at a concentration of 50 µg/ml were shown to potently reduce the expression of many of the polynucleotides up-regulated by 100 ng/ml *E. coli* O111:B4 LPS as studied by polynucleotide microarrays. Peptide and LPS or LPS alone was incubated with the A549 cells for 4 h and the RNA was isolated. 5 µg total RNA was used to make Cy3/Cy5 labeled CDNA probes and hybridized onto Human Operon arrays (PRHU04). The intensity of unstimulated cells is shown in the third column of Table 2. The "Ratio: LPS/control" column refers to the intensity of polynucleotide expression in LPS-simulated cells divided by in the intensity of unstimulated cells. The other columns refer to the intensity of polynucleotide expression in cells stimulated with LPS and peptide divided by unstimulated cells.

TABLE 2

Human A549 Epithelial Cell Polynucleotide Expression up-regulated by *E.coli* O111:B4 LPS and reduced by Cationic Peptides

| Accession Number | Gene | Control: Media only Intensity | Ratio: LPS/control | Ratio: LPS + ID 27/ control | Ratio: LPS + ID 16/ control | Ratio: LPS + ID 22/ control |
|---|---|---|---|---|---|---|
| AL031983 | Unknown | 0.03 | 302.8 | 5.06 | 6.91 | 0.31 |
| L04510 | ADP-ribosylation factor | 0.66 | 213.6 | 1.4 | 2.44 | 3.79 |
| D87451 | ring finger protein | 3.90 | 183.7 | 2.1 | 3.68 | 4.28 |
| AK000869 | hypothetical protein | 0.14 | 120.1 | 2.34 | 2.57 | 2.58 |
| U78166 | Ric like | 0.05 | 91.7 | 0.20 | 16.88 | 21.37 |
| X03066 | MHC class II DO beta | 0.06 | 36.5 | 4.90 | 12.13 | 0.98 |
| AK001904 | hypothetical protein | 0.03 | 32.8 | 5.93 | 0.37 | 0.37 |
| AB037722 | Unknown | 0.03 | 21.4 | 0.30 | 0.30 | 2.36 |
| AK001589 | hypothetical protein | 0.65 | 19.2 | 1.26 | 0.02 | 0.43 |
| AL137376 | Unknown | 1.88 | 17.3 | 0.64 | 1.30 | 1.35 |
| L19185 | thioredoxin-dependent peroxide reductase 1 | 0.06 | 16.3 | 0.18 | 2.15 | 0.18 |
| J05068 | transcobalamin I | 0.04 | 15.9 | 1.78 | 4.34 | 0.83 |
| AB007856 | FEM-1-like death receptor binding protein | 2.63 | 15.7 | 0.62 | 3.38 | 0.96 |
| AK000353 | cytosolic ovarian carcinoma ag 1 | 0.45 | 13.5 | 1.02 | 1.73 | 2.33 |
| X16940 | smooth muscle enteric actin γ2 | 0.21 | 11.8 | 3.24 | 0.05 | 2.26 |
| M54915 | pim-1 oncogene | 1.40 | 11.4 | 0.63 | 1.25 | 1.83 |
| AL122111 | hypothetical protein | 0.37 | 10.9 | 0.21 | 1.35 | 0.03 |
| M95678 | phospholipase C beta 2 | 0.22 | 7.2 | 2.38 | 0.05 | 1.33 |
| AK001239 | hypothetical protein | 2.20 | 6.4 | 1.27 | 1.89 | 2.25 |
| AC004849 | Unknown | 0.14 | 6.3 | 0.07 | 2.70 | 0.07 |
| X06614 | retinoic acid receptor_alpha | 1.92 | 5.5 | 0.77 | 1.43 | 1.03 |
| AB007896 | putative L-type neutral amino acid transporter | 0.94 | 5.3 | 1.82 | 2.15 | 2.41 |
| AB010894 | BAI1-associated protein | 0.69 | 5.0 | 1.38 | 1.03 | 1.80 |
| U52522 | partner of RAC1 | 1.98 | 2.9 | 1.35 | 0.48 | 1.38 |
| AK001440 | hypothetical protein | 1.02 | 2.7 | 0.43 | 1.20 | 0.01 |
| NM_001148 | ankyrin 2_neuronal | 0.26 | 2.5 | 0.82 | 0.04 | 0.66 |
| X07173 | inter-alpha inhibitor H2 | 0.33 | 2.2 | 0.44 | 0.03 | 0.51 |
| AF095687 | brain and nasopharyngeal carcinoma susceptibility protein | 0.39 | 2.1 | 0.48 | 0.03 | 0.98 |
| NM_016382 | NKcell activation inducing ligand NAIL | 0.27 | 2.1 | 0.81 | 0.59 | 0.04 |
| AB023198 | KIAA0981 protein | 0.39 | 2.0 | 0.43 | 0.81 | 0.92 |

EXAMPLE 2

Neutralization of the Stimulation of Immune Cells

The ability of compounds to neutralize the stimulation of immune cells by both Gram-negative and Gram-positive bacterial products was tested. Bacterial products stimulate cells of the immune system to produce inflammatory cytokines and when unchecked this can lead to sepsis. Initial experiments utilized the murine macrophage cell line RAW 264.7, which was obtained from the American Type Culture Collection, (Manassas, Va.), the human epithelial cell line, A549, and primary macrophages derived from the bone marrow of BALB/c mice (Charles River Laboratories, Wilmington, Mass.). The cells from mouse bone marrow were cultured in 150-mm plates in Dulbecco's modified Eagle medium (DMEM; Life Technologies, Burlington, ON) supplemented with 20% FBS (Sigma Chemical Co, St. Louis, Mo.) and 20% L cell-conditioned medium as a source of M-CSF. Once macrophages were 60-80% confluent, they were deprived of L cell-conditioned medium for 14-16 h to render the cells quiescent and then were subjected to treatments with 100 ng/ml LPS or 100 ng/ml LPS+20 µg/ml peptide for 24 hours. The release of cytokines into the culture supernatant was determined by ELISA (R&D Systems, Minneapolis, Minn.). The cell lines, RAW 264.7 and A549, were maintained in DMEM supplemented with 10% fetal calf serum. RAW 264.7 cells were seeded in 24 well plates at a density of $10^6$ cells per well in DMEM and A549 cells were seeded in 24 well plates at a density of $10^5$ cells per well in DMEM and both were incubated at 37° C. in 5% $CO_2$ overnight. DMEM was aspirated from cells grown overnight and replaced with fresh medium. In some experiments, blood from volunteer human donors was collected (according to procedures accepted by UBC Clinical Research Ethics Board, certificate C00-0537) by venipuncture into tubes (Becton Dickinson, Franklin Lakes, N.J.) containing 14.3 USP units heparin/ml blood. The blood was mixed with LPS with or without peptide in polypropylene tubes at 37° C. for 6 h. The samples were centrifuged for 5 min at 2000×g, the plasma was collected and then stored at −20° C. until being analyzed for IL-8 by ELISA (R&D Systems). In the experiments with cells, LPS or other bacterial products were incubated with the cells for 6-24 hr at 37° C. in 5% $CO_2$. S. typhimurium LPS and E. coli O111:B4 LPS were purchased from Sigma. Lipoteichoic acid (LTA) from S. aureus (Sigma) was resuspended in endotoxin free water (Sigma). The Limulus amoebocyte lysate assay (Sigma) was performed on LTA preparations to confirm that lots were not significantly contaminated by endotoxin. Endotoxin contamination was less than 1 ng/ml, a concentration that did not cause significant cytokine production in the RAW 264.7 cells. Non-capped lipoarabinomannan (AraLAM) was a gift from Dr. John T. Belisle of Colorado State University. The AraLAM from Mycobacterium was filter sterilized and the endotoxin contamination was found to be 3.75 ng per 1.0 mg of LAM as determined by Limulus Amebocyte assay. At the same time as LPS addition (or later where specifically described), cationic peptides were added at a range of concentrations. The supernatants were removed and tested for cytokine production by ELISA (R&D Systems). All assays were performed at least three times with similar results. To confirm the anti-sepsis activity in vivo, sepsis was induced by intraperitoneal injection of 2 or 3 µg of E. coli O111:B4 LPS in phosphate-buffered saline (PBS; pH 7.2) into galactosamine-sensitized 8- to 10- week-old female CD-1 or BALB/c mice. In experiments involving peptides, 200 µg in 100µl of sterile water was injected at separate intraperitoneal sites within 10 min of LPS injection. In other experiments, CD-1 mice were injected with 400 µg E. coli O111:B4 LPS and 10 min later peptide (200 µg) was introduced by intraperitoneal injection. Survival was monitored for 48 hours post injection.

Hyperproduction of TNF-α has been classically linked to development of sepsis. The three types of LPS, LTA or AraLAM used in this example represented products released by both Gram-negative and Gram-positive bacteria. Peptide, SEQ ID NO: 1, was able to significantly reduce TNF-α production stimulated by S. typhimurium, B. cepacia, and E. coli O111:B4 LPS, with the former being affected to a somewhat lesser extent (Table 3). At concentrations as low as 1 µg/ml of peptide (0.25 nM) substantial reduction of TNF-α production was observed in the latter two cases. A different peptide, SEQ ID NO: 3 did not reduce LPS-induced production of TNF-α in RAW macrophage cells, demonstrating that this is not a uniform and predictable property of cationic peptides. Representative peptides from each Formula were also tested for their ability to affect TNF-α production stimulated by E. coli O111:B4 LPS (Table 4). The peptides had a varied ability to reduce TNF-α production although many of them lowered TNF-α by at least 60%.

At certain concentrations peptides SEQ ID NO: 1 and SEQ ID NO: 2, could also reduce the ability of bacterial products to stimulate the production of IL-8 by an epithelial cell line. LPS is a known potent stimulus of IL-8 production by epithelial cells. Peptides, at low concentrations (1-20 µg/ml), neutralized the IL-8 induction responses of epithelial cells to LPS (Table 5-7). Peptide SEQ ID 2 also inhibited LPS-induced production of IL-8 in whole human blood (Table 4). Conversely, high concentrations of peptide SEQ ID NO: 1 (50 to 100 µg/ml) actually resulted in increased levels of IL-8 (Table 5). This suggests that the peptides have different effects at different concentrations.

The effect of peptides on inflammatory stimuli was also demonstrated in primary murine cells, in that peptide SEQ ID NO: 1 significantly reduced TNF-α production (>90%) by bone marrow-derived macrophages from BALB/c mice that had been stimulated with 100 ng/ml E. coli O111:B4 LPS (Table 8). These experiments were performed in the presence of serum, which contains LPS-binding protein (LBP), a protein that can mediate the rapid binding of LPS to CD14. Delayed addition of SEQ ID NO: 1to the supernatants of macrophages one hour after stimulation with 100 ng/ml E. coli LPS still resulted in substantial reduction (70%) of TNF-α production (Table 9).

Consistent with the ability of SEQ ID NO: 1 to prevent LPS-induced production of TNF-α in vitro, certain peptides also protected mice against lethal shock induced by high concentrations of LPS. In some experiments, CD-1 mice were sensitized to LPS with a prior injection of galactosamine. Galactosainine-sensitized mice that were injected with 3 µg of E. coli O111:B4 LPS were all killed within 4-6 hours. When 200 µg of SEQ ID NO: 1 was injected 15 min after the LPS, 50% of the mice survived (Table 10). In other experiments when a higher concentration of LPS was injected into BALB/c mice with no D-galactosamine, peptide protected 100% compared to the control group in which there was no survival (Table 13). Selected other peptides were also found to be protective in these models (Tables 11,12).

Cationic peptides were also able to lower the stimulation of macrophages by Gram-positive bacterial products such as *Mycobacterium* non-capped lipoarabinomannan (AraLAM) and *S. aureus* LTA. For example, SEQ ID NO: 1 inhibited induction of TNF-α in RAW 264.7 cells by the Gram-positive bacterial products, LTA (Table 14) and to a lesser extent AraLAM (Table 15). Another peptide, SEQ ID NO: 2, was also found to reduce LTA-induced TNF-α production by RAW 264.7 cells. At a concentration of 1μg/ml SEQ ID NO: 1 was able to substantially reduce (>75%) the induction of TNF-α production by 1 μg/ml *S. aureus* LTA. At 20 μg/ml SEQ ID NO: 1, there was >60% inhibition of AraLAM induced TNF-α. Polymyxin B (PMB) was included as a control to demonstrate that contaminating endotoxin was not a significant factor in the inhibition by SEQ ID NO: 1 of AraLAM induced TNF-α. These results demonstrate that cationic peptides can reduce the pro-inflammatory cytokine response of the immune system to bacterial products.

Table 3: Reduction by SEQ ID 1 of LPS induced TNF-α production in RAW 264.7 cells. RAW 264.7 mouse macrophage cells were stimulated with 100 ng/ml *S. typhimurium* LPS, 100 ng/ml *B. cepacia* LPS and 100 ng/ml *E. coli* O111:B4 LPS in the presence of the indicated concentrations of SEQ ID 1 for 6 hr. The concentrations of TNF-α released into the culture supernatants were determined by ELISA. 100% represents the amount of TNF-α resulting from RAW 264.7 cells incubated with LPS alone for 6 hours (*S. typhimurium* LPS=34.5±3.2 ng/ml, *B. cepacia* LPS=11.6±2.9ng/ml, and *E. coli* O111:B4 LPS =30.8±2.4 ng/ml). Background levels of TNF-α production by the RAW 264.7 cells cultured with no stimuli for 6 hours resulted in TNF-α levels ranging from 0.037-0.192 ng/ml. The data is from duplicate samples and presented as the mean of three experiments+standard error.

| Amount of SEQ ID | Inhibition of TNF-α (%)* | | |
|---|---|---|---|
| 1 (μg/ml) | *B. cepacia* LPS | *E. coli* LPS | *S. typhimurium* LPS |
| 0.1 | 8.5 ± 2.9 | 0.0 ± 0.6 | 0.0 ± 0 |
| 1 | 23.0 ± 11.4 | 36.6 ± 7.5 | 9.8 ± 6.6 |
| 5 | 55.4 ± 8 | 65.0 ± 3.6 | 31.1 ± 7.0 |
| 10 | 63.1 ± 8 | 75.0 ± 3.4 | 37.4 ± 7.5 |
| 20 | 71.7 ± 5.8 | 81.0 ± 3.5 | 58.5 ± 10.5 |
| 50 | 86.7 ± 4.3 | 92.6 ± 2.5 | 73.1 ± 9.1 |

Table 4: Reduction by Cationic Peptides of *E. coli* LPS induced TNF-α production in RAW 264.7 cells. RAW 264.7 mouse macrophage cells were stimulated with 100 ng/ml *E. coli* O111:B4 LPS in the presence of the indicated concentrations of cationic peptides for 6 h. The concentrations of TNF-α released into the culture supernatants were determined by ELISA. Background levels of TNF-α production by the RAW 264.7 cells cultured with no stimuli for 6 hours resulted in TNF-α levels ranging from 0.037-0.192 ng/ml. The data is from duplicate samples and presented as the mean of three experiments+standard deviation.

| Peptide (20 μg/ml) | Inhibition of TNF-α (%) |
|---|---|
| SEQ ID 5 | 65.6 ± 1.6 |
| SEQ ID 6 | 59.8 ± 1.2 |
| SEQ ID 7 | 50.6 ± 0.6 |
| SEQ ID 8 | 39.3 ± 1.9 |
| SEQ ID 9 | 58.7 ± 0.8 |
| SEQ ID 10 | 55.5 ± 0.52 |
| SEQ ID 12 | 52.1 ± 0.38 |
| SEQ ID 13 | 62.4 ± 0.85 |
| SEQ ID 14 | 50.8 ± 1.67 |
| SEQ ID 15 | 69.4 ± 0.84 |
| SEQ ID 16 | 37.5 ± 0.66 |
| SEQ ID 17 | 28.3 ± 3.71 |
| SEQ ID 19 | 69.9 ± 0.09 |
| SEQ ID 20 | 66.1 ± 0.78 |
| SEQ ID 21 | 67.8 ± 0.6 |
| SEQ ID 22 | 73.3 ± 0.36 |
| SEQ ID 23 | 83.6 ± 0.32 |
| SEQ ID 24 | 60.5 ± 0.17 |
| SEQ ID 26 | 54.9 ± 1.6 |
| SEQ ID 27 | 51.1 ± 2.8 |
| SEQ ID 28 | 56 ± 1.1 |
| SEQ ID 29 | 58.9 ± 0.005 |
| SEQ ID 31 | 60.3 ± 0.6 |
| SEQ ID 33 | 62.1 ± 0.08 |
| SEQ ID 34 | 53.3 ± 0.9 |
| SEQ ID 35 | 60.7 ± 0.76 |
| SEQ ID 36 | 63 ± 0.24 |
| SEQ ID 37 | 58.9 ± 0.67 |
| SEQ ID 38 | 54 ± 1 |
| SEQ ID 40 | 75 ± 0.45 |
| SEQ ID 41 | 86 ± 0.37 |
| SEQ ID 42 | 80.5 ± 0.76 |
| SEQ ID 43 | 88.2 ± 0.65 |
| SEQ ID 44 | 44.9 ± 1.5 |
| SEQ ID 45 | 44.7 ± 0.39 |
| SEQ ID 47 | 36.9 ± 2.2 |
| SEQ ID 48 | 64 ± 0.67 |
| SEQ ID 49 | 86.9 ± 0.69 |
| SEQ ID 53 | 46.5 ± 1.3 |
| SEQ ID 54 | 64 ± 0.73 |

TABLE 5

Reduction by SEQ ID 1 of LPS induced IL-8 production in A549 cells. A549 cells were stimulated with increasing concentrations of SEQ ID 1 in the presence of LPS (100 ng/ml *E. coli* O111:B4) for 24 hours. The concentration of IL-8 in the culture supernatants was determined by ELISA. The background levels of IL-8 from cells alone was 0.172 ± 0.029 ng/ml. The data is presented as the mean of three experiments + standard error.

| SEQ ID 1 (μg/ml) | Inhibition of IL-8 (%) |
|---|---|
| 0.1 | 1 ± 0.3 |
| 1 | 32 ± 10 |
| 10 | 60 ± 9 |
| 20 | 47 ± 12 |
| 50 | 40 ± 13 |
| 100 | 0 |

TABLE 6

Reduction by SEQ ID 2 of *E. coli* LPS induced IL-8 production in A549 cells. Human A549 epithelial cells were stimulated with increasing concentrations of SEQ ID 2 in the presence of LPS (100 ng/ml *E. coli* O111:B4) for 24 hours. The concentration of IL-8 in the culture supernatants was determined by ELISA. The data is presented as the mean of three experiments + standard error.

| Concentration of SEQ ID 2 (μg/ml) | Inhibition of IL-8 (%) |
|---|---|
| 0.1 | 6.8 ± 9.6 |
| 1 | 12.8 ± 24.5 |
| 10 | 29.0 ± 26.0 |
| 50 | 39.8 ± 1.6 |
| 100 | 45.0 ± 3.5 |

TABLE 7

Reduction by SEQ ID 2 of *E. coli* LPS induced IL-8 in human blood. Whole human blood was stimulated with increasing concentrations of peptide and *E. coli* O111:B4 LPS for 4 hr. The human blood samples were centrifuged and the serum was removed and tested for IL-8 by ELISA. The data is presented as the average of 2 donors.

| SEQ ID 2 (μg/ml) | IL-8 (pg/ml) |
|---|---|
| 0 | 3205 |
| 10 | 1912 |
| 50 | 1458 |

TABLE 8

Reduction by SEQ ID 1 of *E. coli* LPS induced TNF-α production in murine bone marrow macrophages. BALB/c Mouse bone marrow-derived macrophages were cultured for either 6 h or 24 h with 100 ng/ml *E. coli* 0111: B4 LPS in the presence or absence of 20 μg/ml of peptide. The supernatant was collected and tested for levels of TNF-α by ELISA. The data represents the amount of TNF-α resulting from duplicate wells of bone marrow-derived macrophages incubated with LPS alone for 6 h (1.1 ± 0 0.09 ng/ml) or 24 h (1.7 ± 0.2 ng/ml). Background levels of TNF-α were 0.038 ± 0.008 ng/ml for 6 h and 0.06 ± 0.012 ng/ml for 24 h.

| | Production of TNF-α (ng/ml) | |
|---|---|---|
| SEQ ID 1 (μg/ml) | 6 hours | 24 hours |
| LPS alone | 1.1 | 1.7 |
| 1 | 0.02 | 0.048 |
| 10 | 0.036 | 0.08 |
| 100 | 0.033 | 0.044 |
| No LPS control | 0.038 | 0.06 |

TABLE 9

Inhibition of *E. coli* LPS-induced TNF-α production by delayed addition of SEQ ID 1 to A549 cells. Peptide (20 μg/ml) was added at increasing time points to wells already containing A549 human epithelial cells and 100 ng/ml *E. coli* 0111: B4 LPS. The supernatant was collected after 6 hours and tested for levels of TNF-α by ELISA. The data is presented as the mean of three experiments + standard error.

| Time of addition of SEQ ID 1 after LPS (min) | Inhibition of TNF-α (%) |
|---|---|
| 0 | 98.3 ± 0.3 |
| 15 | 89.3 ± 3.8 |
| 30 | 83 ± 4.6 |
| 60 | 68 ± 8 |
| 90 | 53 ± 8 |

TABLE 10

Protection against lethal endotoxaemia in galactosamine-sensitized CD-1 mice by SEQ ID 1. CD-1 mice (9 weeks-old) were sensitized to endotoxin by three intraperitoneal injections of galactosamine (20 mg in 0.1 ml sterile PBS). Then endotoxic shock was induced by intraperitoneal injection of *E. coli* 0111: B4 LPS (3 μg in 0.1 ml PBS). Peptide, SEQ ID 1, (200 μg/mouse = 8 mg/kg) was injected at a separate intraperitoneal site 15 min after injection of LPS. The mice were monitored for 48 hours and the results were recorded.

| D-Galactosamine treatment | *E. coli* 0111: B4 LPS | Peptide or buffer | Total mice | Survival post endotoxin shock |
|---|---|---|---|---|
| 0 | 3 μg | PBS | 5 | 5 (100%) |
| 20 mg | 3 μg | PBS | 12 | 0 (0%) |
| 20 mg | 3 μg | SEQ ID 1 | 12 | 6 (50%) |

TABLE 11

Protection against lethal endotoxaemia in galactosamine-sensitized CD-1 mice by Cationic Peptides. CD-1 mice (9 weeks-old) were sensitized to endotoxin by intraperitoneal injection of galactosamine (20 mg in 0.1 ml sterile PBS). Then endotoxic shock was induced by intraperitoneal injection of *E. coli* 0111: B4 LPS (2 μg in 0.1 ml PBS). Peptide (200 μg/mouse = 8 mg/kg) was injected at a separate intraperitoneal site 15 min after injection of LPS. The mice were monitored for 48 hours and the results were recorded.

| Peptide Treatment | *E. coli* 0111: B4 LPS added | Number of Mice | Survival (%) |
|---|---|---|---|
| Control (no peptide) | 2 μg | 5 | 0 |
| SEQ ID 6 | 2 μg | 5 | 40 |
| SEQ ID 13 | 2 μg | 5 | 20 |
| SEQ ID 17 | 2 μg | 5 | 40 |
| SEQ ID 24 | 2 μg | 5 | 0 |
| SEQ ID 27 | 2 μg | 5 | 20 |

TABLE 12

Protection against lethal endotoxaemia in galactosamine-sensitized BALB/c mice by Cationic Peptides. BALB/c mice (8 weeks-old) were sensitized to endotoxin by intraperitoneal injection of galactosamine (20 mg in 0.1 ml sterile PBS). Then endotoxic shock was induced by intraperitoneal injection of *E. coli* 0111:B4 LPS (2 μg in 0.1 ml PBS). Peptide (200 μg/mouse = 8 mg/kg) was injected at a separate intraperitoneal site 15 min after injection of LPS. The mice were monitored for 48 hours and the results were recorded.

| Peptide Treatment | *E. coli* 0111:B4 LPS added | Number of Mice | Survival (%) |
|---|---|---|---|
| No peptide | 2 μg | 10 | 10 |
| SEQ ID 1 | 2 μg | 6 | 17 |
| SEQ ID 3 | 2 μg | 6 | 0 |
| SEQ ID 5 | 2 μg | 6 | 17 |
| SEQ ID 6 | 2 μg | 6 | 17 |
| SEQ ID 12 | 2 μg | 6 | 17 |
| SEQ ID 13 | 2 μg | 6 | 33 |
| SEQ ID 15 | 2 μg | 6 | 0 |
| SEQ ID 16 | 2 μg | 6 | 0 |
| SEQ ID 17 | 2 μg | 6 | 17 |
| SEQ ID 23 | 2 μg | 6 | 0 |
| SEQ ID 24 | 2 μg | 6 | 17 |
| SEQ ID 26 | 2 μg | 6 | 0 |
| SEQ ID 27 | 2 μg | 6 | 50 |
| SEQ ID 29 | 2 μg | 6 | 0 |
| SEQ ID 37 | 2 μg | 6 | 0 |
| SEQ ID 38 | 2 μg | 6 | 0 |
| SEQ ID 41 | 2 μg | 6 | 0 |
| SEQ ID 44 | 2 μg | 6 | 0 |
| SEQ ID 45 | 2 μg | 6 | 0 |

TABLE 13

Protection against lethal endotoxaemia in BALB/c mice by SEQ ID 1. BALB/c mice were injected intraperitoneal with 400 μg E. coli 0111:B4 LPS. Peptide (200 μg/mouse = 8 mg/kg) was injected at a separate intraperitoneal site and the mice were monitored for 48 hours and the results were recorded.

| Peptide Treatment | E. coli 0111:B4 LPS | Number of Mice | Survival (%) |
|---|---|---|---|
| No peptide | 400 μg | 5 | 0 |
| SEQ ID 1 | 400 μg | 5 | 100 |

TABLE 14

Peptide inhibition of TNF-α production induced by S. aureus LTA. RAW 264.7 mouse macrophage cells were stimulated with 1 μg/ml S. aureus LTA in the absence and presence of increasing concentrations of peptide. The supernatant was collected and tested for levels of TNF-α by ELISA. Background levels of TNF-α production by the RAW 264.7 cells cultured with no stimuli for 6 hours resulted in TNF-α levels ranging from 0.037-0.192 ng/ml. The data is presented as the mean of three or more experiments + standard error.

| SEQ ID 1 added (μg/ml) | Inhibition of TNF-α (%) |
|---|---|
| 0.1 | 44.5 ± 12.5 |
| 1 | 76.7 ± 6.4 |
| 5 | 91 ± 1 |
| 10 | 94.5 ± 1.5 |
| 20 | 96 ± 1 |

TABLE 15

Peptide inhibition of TNF-α production induced by Mycobacterium non-capped lipoarabinomannan. RAW 264.7 mouse macrophage cells were stimulated with 1 μg/ml AraLAM in the absence and presence of 20 μg/ml peptide or Polymyxin B. The supernatant was collected and tested for levels of TNF-α by ELISA. Background levels of TNF-α production by the RAW 264.7 cells cultured with no stimuli for 6 hours resulted in TNF-α levels ranging from 0.037-0.192 ng/ml. The data is presented as the mean inhibition of three or more experiments + standard error.

| Peptide (20 μg/ml) | Inhibition of TNF-α (%) |
|---|---|
| No peptide | 0 |
| SEQ ID 1 | 64 ± 5.9 |
| Polymyxin B | 15 ± 2 |

EXAMPLE 3

Assessment of Toxicity of the Cationic Peptides

The potential toxicity of the peptides was measured in two ways. First, the Cytotoxicity Detection Kit (Roche) (Lactate dehydrogenase -LDH) Assay was used. It is a calorimetric assay for the quantification of cell death and cell lysis, based on the measurement of LDH activity released from the cytosol of damaged cells into the supernatant. LDH is a stable cytoplasmic enzyme present in all cells and it is released into the cell culture supernatant upon damage of the plasma membrane. An increase in the amount of dead or plasma membrane-damaged cells results in an increase of the LDH enzyme activity in the culture supernatant as measured with an ELISA plate reader, $OD_{490}$ nm (the amount of color formed in the assay is proportional to the number of lysed cells). In this assay, human bronchial epithelial cells (16HBEo14, HBE) cells were incubated with 100 μg of peptide for 24 hours, the supernatant removed and tested for LDH. The other assay used to measure toxicity of the cationic peptides was the WST-1assay (Roche). This assay is a calorimetric assay for the quantification of cell proliferation and cell viability, based on the cleavage of the tetrazolium salt WST-1 by mitochondrial dehydrogenases in viable cells (a non-radioactive alternative to the $[^3H]$-thymidine incorporation assay). In this assay, HBE cells were incubated with 100 μg of peptide for 24 hours, and then 10 μl/well Cell Proliferation Reagent WST-1 was added. The cells are incubated with the reagent and the plate is then measured with an ELISA plate reader, $OD_{490}$ nm.

The results shown below in Tables 16 and 17 demonstrate that most of the peptides are not toxic to the cells tested. However, four of the peptides from Formula F (SEQ ID NOS: 40, 41, 42 and 43) did induce membrane damage as measured by both assays.

TABLE 16

Toxicity of the Cationic Peptides as Measured by the LDH Release Assay. Human HBE bronchial epithelial cells were incubated with 100 μg/ml peptide or Polymyxin B for 24 hours. LDH activity was assayed in the supernatant of the cell cultures. As a control for 100% LDH release, Triton X-100 was added. The data is presented as the mean ± standard deviation. Only peptides SEQ ID 40, 41, 42 and 43 showed any significant toxicity.

| Treatment | LDH Release ($OD_{490}$ nm) |
|---|---|
| No cells Control | 0.6 ± 0.1 |
| Triton X-100 Control | 4.6 ± 0.1 |
| No peptide control | 1.0 ± 0.05 |
| SEQ ID 1 | 1.18 ± 0.05 |
| SEQ ID 3 | 1.05 ± 0.04 |
| SEQ ID 6 | 0.97 ± 0.02 |
| SEQ ID 7 | 1.01 ± 0.04 |
| SEQ ID 9 | 1.6 ± 0.03 |
| SEQ ID 10 | 1.04 ± 0.04 |
| SEQ ID 13 | 0.93 ± 0.06 |
| SEQ ID 14 | 0.99 ± 0.05 |
| SEQ ID 16 | 0.91 ± 0.04 |
| SEQ ID 17 | 0.94 ± 0.04 |
| SEQ ID 19 | 1.08 ± 0.02 |
| SEQ ID 20 | 1.05 ± 0.03 |
| SEQ ID 21 | 1.06 ± 0.04 |
| SEQ ID 22 | 1.29 ± 0.12 |
| SEQ ID 23 | 1.26 ± 0.46 |
| SEQ ID 24 | 1.05 ± 0.01 |
| SEQ ID 26 | 0.93 ± 0.04 |
| SEQ ID 27 | 0.91 ± 0.04 |
| SEQ ID 28 | 0.96 ± 0.06 |
| SEQ ID 29 | 0.99 ± 0.02 |
| SEQ ID 31 | 0.98 ± 0.03 |
| SEQ ID 33 | 1.03 ± 0.05 |
| SEQ ID 34 | 1.02 ± 0.03 |
| SEQ ID 35 | 0.88 ± 0.03 |
| SEQ ID 36 | 0.85 ± 0.04 |
| SEQ ID 37 | 0.96 ± 0.04 |
| SEQ ID 38 | 0.95 ± 0.02 |
| SEQ ID 40 | 2.8 ± 0.5 |
| SEQ ID 41 | 3.3 ± 0.2 |
| SEQ ID 42 | 3.4 ± 0.2 |
| SEQ ID 43 | 4.3 ± 0.2 |
| SEQ ID 44 | 0.97 ± 0.03 |
| SEQ ID 45 | 0.98 ± 0.04 |
| SEQ ID 47 | 1.05 ± 0.05 |
| SEQ ID 48 | 0.95 ± 0.05 |
| SEQ ID 53 | 1.03 ± 0.06 |
| Polymyxin B | 1.21 ± 0.03 |

TABLE 17

Toxicity of the Cationic Peptides as Measured by the WST-1 Assay. HBE cells were incubated with 100 μg/ml peptide or Polymyxin B for 24 hours and cell viability was tested. The data is presented as the mean ± standard deviation. As a control for 100% LDH release, Triton X-100 was added. Only peptides SEQ ID 40, 41, 42 and 43 showed any significant toxicity.

| Treatment | OD$_{490}$ nm |
|---|---|
| No cells Control | 0.24 ± 0.01 |
| Triton X-100 Control | 0.26 ± 0.01 |
| No peptide control | 1.63 ± 0.16 |
| SEQ ID 1 | 1.62 ± 0.34 |
| SEQ ID 3 | 1.35 ± 0.12 |
| SEQ ID 10 | 1.22 ± 0.05 |
| SEQ ID 6 | 1.81 ± 0.05 |
| SEQ ID 7 | 1.78 ± 0.10 |
| SEQ ID 9 | 1.69 ± 0.29 |
| SEQ ID 13 | 1.23 ± 0.11 |
| SEQ ID 14 | 1.25 ± 0.02 |
| SEQ ID 16 | 1.39 ± 0.26 |
| SEQ ID 17 | 1.60 ± 0.46 |
| SEQ ID 19 | 1.42 ± 0.15 |
| SEQ ID 20 | 1.61 ± 0.21 |
| SEQ ID 21 | 1.28 ± 0.07 |
| SEQ ID 22 | 1.33 ± 0.07 |
| SEQ ID 23 | 1.14 ± 0.24 |
| SEQ ID 24 | 1.27 ± 0.16 |
| SEQ ID 26 | 1.42 ± 0.11 |
| SEQ ID 27 | 1.63 ± 0.03 |
| SEQ ID 28 | 1.69 ± 0.03 |
| SEQ ID 29 | 1.75 ± 0.09 |
| SEQ ID 31 | 1.84 ± 0.06 |
| SEQ ID 33 | 1.75 ± 0.21 |
| SEQ ID 34 | 0.96 ± 0.05 |
| SEQ ID 35 | 1.00 ± 0.08 |
| SEQ ID 36 | 1.58 ± 0.05 |
| SEQ ID 37 | 1.67 ± 0.02 |
| SEQ ID 38 | 1.83 ± 0.03 |
| SEQ ID 40 | 0.46 ± 0.06 |
| SEQ ID 41 | 0.40 ± 0.01 |
| SEQ ID 42 | 0.39 ± 0.08 |
| SEQ ID 43 | 0.46 ± 0.10 |
| SEQ ID 44 | 1.49 ± 0.39 |
| SEQ ID 45 | 1.54 ± 0.35 |
| SEQ ID 47 | 1.14 ± 0.23 |
| SEQ ID 48 | 0.93 ± 0.08 |
| SEQ ID 53 | 1.51 ± 0.37 |
| Polymyxin B | 1.30 ± 0.13 |

EXAMPLE 4

Polynucleotide Regulation by Cationic Peptides

Polynucleotide arrays were utilized to determine the effect of cationic peptides by themselves on the transcriptional response of macrophages and epithelial cells. Mouse macrophage RAW 264.7, Human Bronchial cells (HBE), or A549 human epithelial cells were plated in 150 mm tissue culture dishes at 5.6×10$^6$ cells/dish, cultured overnight and then incubated with 50 μg/ml peptide or medium alone for 4 h. After stimulation, the cells were washed once with diethyl pyrocarbonate-treated PBS, and detached from the dish using a cell scraper. Total RNA was isolated using Trizol (Gibco Life Technologies). The RNA pellet was resuspended in RNase-free water containing RNase inhibitor (Ambion, Austin, Tex.). The RNA was treated with DNaseI (Clontech, Palo Alto, Calif.) for 1 h at 37° C. After adding termination mix (0.1 M EDTA [pH 8.0], 1 mg/ml glycogen), the samples were extracted once with phenol: chloroform: isoamyl alcohol (25: 24:1), and once with chloroform. The RNA was then precipitated by adding 2.5 volumes of 100% ethanol7 and 1/10$^{th}$ volume sodium acetate, pH 5.2. The RNA was resuspended in RNase-free water with RNase inhibitor (Ambion) and stored at −70° C. The quality of the RNA was assessed by gel electrophoresis on a 1% agarose gel. Lack of genomic DNA contamination was assessed by using the isolated RNA as a template for PCR amplification with β-actin-specific primers (5'-GTCCCTGTATGCCTCTGGTC-3'(SEQ ID NO: 55) and 5'-GATGTCACGCACGATTTCC-3'(SEQ ID NO: 56)). Agarose gel electrophoresis and ethidium bromide staining confirmed the absence of an amplicon after 35 cycles.

Atlas cDNA Expression Arrays (Clontech, Palo Alto, Calif.), which consist of 588 selected mouse cDNAs spotted in duplicate on positively charged membranes were used for early polynucleotide array studies (Tables 18,19). $^{32}$P-radiolabeled CDNA probes prepared from 5 μg total RNA were incubated with the arrays overnight at 71° C. The filters were washed extensively and then exposed to a phosphoimager screen (Molecular Dynamics, Sunnyvale, Calif.) for 3 days at 4° C. The image was captured using a Molecular Dynamics PSI phosphoimager. The hybridization signals were analyzed using AtlasImage 1.0 Image Analysis software (Clontech) and Excel (Microsoft, Redmond, Wash.). The intensities for each spot were corrected for background levels and normalized for differences in probe labeling using the average values for 5 polynucleotides observed to vary little between the stimulation conditions: β-actin, ubiquitin, ribosomal protein S29, glyceraldehyde-3-phosphate dehydrogenase (GAPDH), and Ca$^{2+}$ binding protein. When the normalized hybridization intensity for a given cDNA was less than 20, it was assigned a value of 20 to calculate the ratios and relative expression.

The next polynucleotide arrays used (Tables 21-26) were the Resgen Human cDNA arrays (identification number for the genome is PRHU03-S3), which consist of 7,458 human cDNAs spotted in duplicate. Probes were prepared from 15-20 μg of total RNA and labeled with Cy3 labeled dUTP. The probes were purified and hybridized to printed glass slides overnight at 42° C. and washed. After washing, the image was captured using a Virtek slide reader. The image processing software (Imagene 4.1, Marina Del Rey, Calif.) determines the spot mean intensity, median intensities, and background intensities. Normalization and analysis was performed with Genespring software (Redwood City, Calif.). Intensity values were calculated by subtracting the mean background intensity from the mean intensity value determined by Imagene. The intensities for each spot were normalized by taking the median spot intensity value from the population of spot values within a slide and comparing this value to the values of all slides in the experiment. The relative changes seen with cells treated with peptide compared to control cells can be found in the Tables below.

The other polynucleotide arrays used (Tables 27-35) were the Human Operon arrays (identification number for the genome is PRHU04-S1), which consist of about 14,000 human oligos spotted in duplicate. Probes were prepared from 10 μg of total RNA and labeled with Cy3 or Cy5 labeled dUTP. In these experiments, A549 epithelial cells were plated in 100 mm tissue culture dishes at 2.5×10$^6$ cells/dish. Total RNA was isolated using RNAqueous (Ambion). DNA contamination was removed with DNA-free kit (Ambion). The probes prepared from total RNA were purified and hybridized to printed glass slides overnight at 42° C. and washed. After washing, the image was captured using a Perkin Elmer array scanner. The image processing software (Imagene 5.0, Marina Del Rey, Calif.) determines the spot mean intensity, median intensities, and background intensities. An "in house" program was used to remove background. The program calculates the bottom 10% intensity for each subgrid and subtracts this for each grid. Analysis was performed with Genespring software (Redwood City, Calif.). The intensities for each spot were normalized by taking the median spot intensity value from the population of spot values within a slide and comparing this value to the values of all slides in the experiment. The relative changes seen with cells treated with peptide compared to control cells can be found in the Tables below.

Semi-quantitative RT-PCR was performed to confirm polynucleotide array results. 1 µg RNA samples were incubated with 1 µl oligodT (500 µg/ml) and 1 µl mixed dNTP stock at 1 mM, in a 12 µl volume with DEPC treated water at 65° C. for 5 min in a thermocycler. 4 µl 5X First Strand buffer, 2 µl 0.1M DTT, and 1 µl RNaseOUT recombinant ribonuclease inhibitor (40 units/µl) were added and incubated at 42° C. for 2min, followed by the addition of 1 µl (200 units) of Superscript II (Invitrogen, Burlington, ON). Negative controls for each RNA source were generated using parallel reactions in the absence of Superscript II. cDNAs were amplified in the presence of 5' and 3' primers (1.0 µM), 0.2 mM dNTP mixture, 1.5 mM MgCl, 1 U of Taq DNA polymerase (New England Biolabs, Missisauga, ON), and 1×PCR buffer. Each PCR was performed with a thermal cycler by using 30-40 cycles consisting of 30s of denaturation at 94° C., 30s of annealing at either 52° C. or 55° C. and 40s of extension at 72° C. The number of cycles of PCR was optimized to lie in the linear phase of the reaction for each primer and set of RNA samples. A housekeeping polynucleotide β-actin was amplified in each experiment to evaluate extraction procedure and to estimate the amount of RNA. The reaction product was visualized by electrophoresis and analyzed by densitometry, with relative starting RNA concentrations calculated with reference to β-actin amplification.

Table 18 demonstrates that SEQ ID NO: 1 treatment of RAW 264.7 cells up-regulated the expression of more than 30 different polynucleotides on small Atlas microarrays with selected known polynucleotides. The polynucleotides up-regulated by peptide, SEQ ID NO: 1, were mainly from two categories: one that includes receptors (growth, chemokine, interleukin, interferon, hormone, neurotransmitter), cell surface antigens and cell adhesion and another one that includes cell-cell communication (growth factors, cytokines, chemokines, interleukin, interferons, hormones), cytoskeleton, motility, and protein turnover. The specific polynucleotides up-regulated included those encoding chemokine MCP-3, the anti-inflammatory cytokine IL-10, macrophage colony stimulating factor, and receptors such as IL-1R-2 (a putative antagonist of productive IL-1 binding to IL-1R1), PDGF receptor B, NOTCH4, LIF receptor, LFA-1, TGFβ receptor 1, G-CSF receptor, and IFNγ receptor. The peptide also up-regulated polynucleotides encoding several metalloproteinases, and inhibitors thereof, including the bone morphogenetic proteins BMP-1, BMP-2, BMP-8a, TIMP2 and TIMP3. As well, the peptide up-regulated specific transcription factors, including JunD, and the YY and LIM-1 transcription factors, and kinases such as Etk1 and Csk demonstrating its widespread effects. It was also discovered from the polynucleotide array studies that SEQ ID NO: 1 down-regulated at least 20 polynucleotides in RAW 264.7 macrophage cells (Table 19). The polynucleotides down-regulated by peptide included DNA repair proteins and several inflammatory mediators such as MIP-1α, oncostatin M and IL-12. A number of the effects of peptide on polynucleotide expression were confirmed by RT-PCR (Table 20). The peptides, SEQ ID NO: 2, SEQ ID NO: 3, SEQ ID NO: 19, and SEQ ID NO: 1, and representative peptides from each of the formulas also altered the transcriptional responses in a human epithelial cell line using mid-sized microarrays (7835 polynucleotides). The effect of SEQ ID NO: 1 on polynucleotide expression was compared in 2 human epithelial cell lines, A549 and HBE. Polynucleotides related to the host immune response that were up-regulated by 2 peptides or more by a ratio of 2-fold more than unstimulated cells are described in Table 21. Polynucleotides that were down-regulated by 2 peptides or more by a ratio of 2-fold more than unstimulated cells are described in Table 22. In Table 23 and Table 24, the human epithelial pro-inflammatory polynucleotides that are up- and down-regulated respectively are shown. In Table 25 and Table 26 the anti-inflammatory polynucleotides affected by cationic peptides are shown. The trend becomes clear that the cationic peptides up-regulate the anti-inflammatory response and down-regulate the pro-inflammatory response. It was very difficult to find a polynucleotide related to the anti-inflammatory response that was down-regulated (Table 26). The pro-inflammatory polynucleotides upregulated by cationic peptides were mainly polynucleotides related to migration and adhesion. Of the down-regulated pro-inflammatory polynucleotides, it should be noted that all the cationic peptides affected several toll-like receptor (TLR) polynucleotides, which are very important in signaling the host response to infectious agents. An important anti-inflammatory polynucleotide that was up-regulated by all the peptides is the IL-10 receptor. IL-10 is an important cytokine involved in regulating the pro-inflammatory cytokines. These polynucleotide expression effects were also observed using primary human macrophages as observed for peptide SEQ ID NO: 6 in Tables 27 and 28. The effect of representative peptides from each of the formulas on human epithelial cell expression of selected polynucleotides (out of 14,000 examined) is shown in Tables 31-37 below. At least 6 peptides from each formula were tested for their ability to alter human epithelial polynucleotide expression and indeed they had a wide range of stimulatory effects. In each of the formulas there were at least 50 polynucleotides commonly up-regulated by each of the peptides in the group.

TABLE 18

Polynucleotides up-regulated by peptide, SEQ ID NO: 1, treatment of RAW macrophage cells[a].

The cationic peptides at a concentration of 50 µg/ml were shown to potently induce the expression of several polynucleotides. Peptide was incubated with the RAW cells for 4 h and the RNA was isolated, converted into labeled cDNA probes and hybridized to Atlas arrays. The intensity of unstimulated cells is shown in the third column. The "Ratio Peptide: Unstimulated" column refers to the intensity of polynucleotide expression in peptide-simulated cells divided by the intensity of unstimulated cells.

The changes in the normalized intensities of the housekeeping polynucleotides ranged from 0.8-1.2 fold, validating the use of these polynucleotides for normalization. When the normalized hybridization intensity for a given cDNA was less than 20, it was assigned a value of 20 to calculate the ratios and relative expression. The array experiments were repeated 3 times with different RNA preparations and the average fold change is shown above. Polynucleotides with a two fold or greater change in relative expression levels are presented.

| Polynucleotide/ Protein | Polynucleotide Function | Unstimulated Intensity | Ratio peptide: Unstimulated[b] | Accession Number |
|---|---|---|---|---|
| Etk1 | Tyrosine-protein kinase receptor | 20 | 43 | M68513 |
| PDGFRB | Growth factor receptor | 24 | 25 | X04367 |
|  | Corticotropin releasing factor receptor | 20 | 23 | X72305 |
| NOTCH4 | proto-oncopolynucleotide | 48 | 18 | M80456 |
| IL-1R2 | Interleukin receptor | 20 | 16 | X59769 |
| MCP-3 | Chemokine | 56 | 14 | S71251 |
| BMP-1 | Bone morphopolynucleotidetic protein | 20 | 14 | L24755 |
| Endothelin b receptor | Receptor | 20 | 14 | U32329 |
| c-ret | Oncopolynucleotide precursor | 20 | 13 | X67812 |
| LIFR | Cytokine receptor | 20 | 12 | D26177 |
| BMP-8a | Bone morphopolynucleotidetic protein | 20 | 12 | M97017 |
| Zfp92 | Zinc finger protein 92 | 87 | 11 | U47104 |
| MCSF | Macrophage colony stimulating factor 1 | 85 | 11 | X05010 |
| GCSFR | Granulocyte colony-stimulating factor receptor | 20 | 11 | M58288 |
| IL-8RB | Chemokine receptor | 112 | 10 | D17630 |
| IL-9R | Interleukin receptor | 112 | 6 | M84746 |
| Cas | Crk-associated substrate | 31 | 6 | U48853 |
| p58/GTA | Kinase | 254 | 5 | M58633 |
| CASP2 | Caspase precursor | 129 | 5 | D28492 |
| IL-1β precursor | Interleukin precursor | 91 | 5 | M15131 |
| SPI2-2 | Serine protease inhibitor | 62 | 5 | M64086 |
| C5AR | Chemokine receptor | 300 | 4 | S46665 |
| L-myc | Oncopolynucleotide | 208 | 4 | X13945 |
| IL-10 | Interleukin | 168 | 4 | M37897 |
| p19ink4 | cdk4 and cdk6 inhibitor | 147 | 4 | U19597 |
| ATOH2 | Atonal homolog 2 | 113 | 4 | U29086 |
| DNAse1 | DNase | 87 | 4 | U00478 |
| CXCR-4 | Chemokine receptor | 36 | 4 | D87747 |
| Cyclin D3 | Cyclin | 327 | 3 | U43844 |
| IL-7Rα | Interleukin receptor | 317 | 3 | M29697 |
| POLA | DNA polymerase$_\alpha$ | 241 | 3 | D17384 |
| Tie-2 | Oncopolynucleotide | 193 | 3 | S67051 |
| DNL1 | DNA ligase I | 140 | 3 | U04674 |
| BAD | Apoptosis protein | 122 | 3 | L37296 |
| GADD45 | DNA-damage-inducible protein | 88 | 3 | L28177 |
| Sik | Src-related kinase | 82 | 3 | U16805 |
| integrin$_\alpha$4 | Integrin | 2324 | 2 | X53176 |
| TGFβR1 | Growth factor receptor | 1038 | 2 | D25540 |
| LAMR1 | Receptor | 1001 | 2 | J02870 |
| Crk | Crk adaptor protein | 853 | 2 | S72408 |
| ZFX | Chromosomal protein | 679 | 2 | M32309 |
| Cyclin E1 | Cylcin | 671 | 2 | X75888 |
| POLD1 | DNA polymerase subunit | 649 | 2 | Z21848 |
| Vav | proto-oncopolynucleotide | 613 | 2 | X64361 |

TABLE 18-continued

Polynucleotides up-regulated by peptide, SEQ ID NO: 1, treatment of RAW macrophage cells[a].

| | | | | |
|---|---|---|---|---|
| YY (NF-E1) | Transcription factor | 593 | 2 | L13968 |
| JunD | Transcription factor | 534 | 2 | J050205 |
| Csk | c-src kinase | 489 | 2 | U05247 |
| Cdk7 | Cyclin-dependent kinase | 475 | 2 | U11822 |
| MLC1A | Myosin light subunit isoform | 453 | 2 | M19436 |
| ERBB-3 | Receptor | 435 | 2 | L47240 |
| UBF | Transcription factor | 405 | 2 | X60831 |
| TRAIL | Apoptosis ligand | 364 | 2 | U37522 |
| LFA-1 | Cell adhesion receptor | 340 | 2 | X14951 |
| SLAP | Src-like adaptor protein | 315 | 2 | U29056 |
| IFNGR | Interferon gamma receptor | 308 | 2 | M28233 |
| LIM-1 | Transcription factor | 295 | 2 | Z27410 |
| ATF2 | Transcription factor | 287 | 2 | S76657 |
| FST | Follistatin precursor | 275 | 2 | Z29532 |
| TIMP3 | Protease inhibitor | 259 | 2 | L19622 |
| RU49 | Transcription factor | 253 | 2 | U41671 |
| IGF-1Rα | Insulin-like growth factor receptor | 218 | 2 | U00182 |
| Cyclin G2 | Cyclin | 214 | 2 | U95826 |
| fyn | Tyrosine-protein kinase | 191 | 2 | U70324 |
| BMP-2 | Bone morphopolynucleotidetic protein | 186 | 2 | L25602 |
| Brn-3.2 POU | Transcription factor | 174 | 2 | S68377 |
| KIF1A | Kinesin family protein | 169 | 2 | D29951 |
| MRC1 | Mannose receptor | 167 | 2 | Z11974 |
| PAI2 | Protease inhibitor | 154 | 2 | X19622 |
| BKLF | CACCC Box-binding protein | 138 | 2 | U36340 |
| TIMP2 | Protease inhibitor | 136 | 2 | X62622 |
| Mas | Proto-oncopolynucleotide | 131 | 2 | X67735 |
| NURR-1 | Transcription factor | 129 | 2 | S53744 |

TABLE 19

Polynucleotides down-regulated by SEQ ID NO: 1 treatment of RAW macrophage cells[a].

The cationic peptides at a concentration of 50 μg/ml were shown to reduce the expression of several polynucleotides. Peptide was incubated with the RAW cells for 4 h and the RNA was isolated, converted into labeled cDNA probes and hybridized to Atlas arrays. The intensity of unstimulated cells is shown in the third column. The "Ratio Peptide: Unstimulated" column refers to the intensity of polynucleotide expression in peptide-simulated cells divided by the intensity of unstimulated cells. The array experiments were repeated 3 times with different cells and the average fold change is shown below. Polynucleotides with an approximately two fold or greater change in relative expression levels are presented.

| Polynucleotide/ Protein | Polynucleotide Function | Unstimulated Intensity | Ratio peptide: Unstimulated | Accession Number |
|---|---|---|---|---|
| sodium channel | Voltage-gated ion channel | 257 | 0.08 | L36179 |
| XRCC1 | DNA repair protein | 227 | 0.09 | U02887 |
| ets-2 | Oncopolynucleotide | 189 | 0.11 | J04103 |
| XPAC | DNA repair protein | 485 | 0.12 | X74351 |
| EPOR | Receptor precursor | 160 | 0.13 | J04843 |
| PEA 3 | Ets-related protein | 158 | 0.13 | X63190 |
| orphan receptor | Nuclear receptor | 224 | 0.2 | U11688 |
| N-cadherin | Cell adhesion receptor | 238 | 0.23 | M31131 |
| OCT3 | Transcription factor | 583 | 0.24 | M34381 |
| PLCβ | phospholipase | 194 | 0.26 | U43144 |
| KRT18 | Intermediate filament proteins | 318 | 0.28 | M11686 |
| THAM | Enzyme | 342 | 0.32 | X58384 |
| CD40L | CD40 ligand | 66 | 0.32 | X65453 |
| CD86 | T-lymphocyte antigen | 195 | 0.36 | L25606 |
| oncostatin M | Cytokine | 1127 | 0.39 | D31942 |

TABLE 19-continued

Polynucleotides down-regulated by SEQ ID NO: 1 treatment of RAW macrophage cells[a].

The cationic peptides at a concentration of 50 μg/ml were shown to reduce the expression of several polynucleotides. Peptide was incubated with the RAW cells for 4 h and the RNA was isolated, converted into labeled cDNA probes and hybridized to Atlas arrays. The intensity of unstimulated cells is shown in the third column. The "Ratio Peptide: Unstimulated" column refers to the intensity of polynucleotide expression in peptide-simulated cells divided by the intensity of unstimulated cells. The array experiments were repeated 3 times with different cells and the average fold change is shown below. Polynucleotides with an approximately two fold or greater change in relative expression levels are presented.

| Polynucleotide/Protein | Polynucleotide Function | Unstimulated Intensity | Ratio peptide: Unstimulated | Accession Number |
|---|---|---|---|---|
| PMS2 | DNA repair protein | 200 | 0.4 | U28724 |
| IGFBP6 | Growth factor | 1291 | 0.41 | X81584 |
| MIP-1β | Cytokine | 327 | 0.42 | M23503 |
| ATBF1 | AT motif-binding factor | 83 | 0.43 | D26046 |
| nucleobindin | Golgi resident protein | 367 | 0.43 | M96823 |
| bcl-x | Apoptosis protein | 142 | 0.43 | L35049 |
| uromodulin | glycoprotein | 363 | 0.47 | L33406 |
| IL-12 p40 | Interleukin | 601 | 0.48 | M86671 |
| MmRad52 | DNA repair protein | 371 | 0.54 | Z32767 |
| Tob1 | Antiproliferative factor | 956 | 0.5 | D78382 |
| Ung1 | DNA repair protein | 535 | 0.51 | X99018 |
| KRT19 | Intermediate filament proteins | 622 | 0.52 | M28698 |
| PLCγ | phospholipase | 251 | 0.52 | X95346 |
| Integrin α₆ | Cell adhesion receptor | 287 | 0.54 | X69902 |
| GLUT1 | Glucose transporter | 524 | 0.56 | M23384 |
| CTLA4 | immunoglobin superfamily | 468 | 0.57 | X05719 |
| FRA2 | Fos-related antigen | 446 | 0.57 | X83971 |
| MTRP | Lysosome-associated protein | 498 | 0.58 | U34259 |

TABLE 20

Polynucleotide Expression changes in response to peptide, SEQ ID NO: 1, could be confirmed by RT-PCR. RAW 264.7 macrophage cells were incubated with 50 μg/ml of peptide or media only for 4 hours and total RNA isolated and subjected to semi-quantitative RT-PCR. Specific primer pairs for each polynucleotide were used for amplification of RNA. Amplification of β-actin was used as a positive control and for standardization. Densitometric analysis of RT-PCR products was used. The results refer to the relative fold change in polynucleotide expression of peptide treated cells compared to cells incubated with media alone. The data is presented as the mean ± standard error of three experiments.

| Polynucleotide | Array Ratio-* | RT-PCR Ratio-* |
|---|---|---|
| CXCR-4 | 4.0 ± 1.7 | 4.1 ± 0.9 |
| IL-8RB | 9.5 ± 7.6 | 7.1 ± 1.4 |
| MCP-3 | 13.5 ± 4.4 | 4.8 ± 0.88 |
| IL-10 | 4.2 ± 2.1 | 16.6 ± 6.1 |
| CD14 | 0.9 ± 0.1 | 0.8 ± 0.3 |
| MIP-1B | 0.42 ± 0.09 | 0.11 ± 0.04 |
| XRCC1 | 0.12 ± 0.01 | 0.25 ± 0.093 |
| MCP-1 | Not on array | 3.5 ± 1.4 |

TABLE 21

Polynucleotides up-regulated by peptide treatment of A549 epithelial cells[a].
The cationic peptides at concentrations of 50 μg/ml were shown to increase the expression of several polynucleotides. Peptide was incubated with the human A549 epithelial cells for 4 h and the RNA was isolated, converted into labeled cDNA probes and hybridized to Human cDNA arrays ID#PRHU03-S3. The intensity of polynucleotides in unstimulated cells is shown in the second column. The "Ratio Peptide: Unstimulated" columns refers to the intensity of polynucleotide expression in peptide-simulated cells divided by the intensity of unstimulated cells.

| Polynucleotide/Protein | Unstimulated Intensity | Ratio Peptide: Unstimulated | | | | Accession Number |
|---|---|---|---|---|---|---|
| | | ID 2 | ID 3 | ID 19 | ID 1 | |
| IL-1 R antagonist homolog 1 | 0.00 | 3086 | 1856 | 870 | | AI167887 |
| IL-10 R beta | 0.53 | 2.5 | 1.6 | 1.9 | 3.1 | AA486393 |
| IL-11 R alpha | 0.55 | 2.4 | 1.0 | 4.9 | 1.8 | AA454657 |
| IL-17 R | 0.54 | 2.1 | 2.0 | 1.5 | 1.9 | AW029299 |
| TNF R superfamily, member 1B | 0.28 | 18 | 3.0 | 15 | 3.6 | AA150416 |
| TNF R superfamily, member 5 (CD40LR) | 33.71 | 3.0 | 0.02 | | | H98636 |
| TNF R superfamily, member 11b | 1.00 | 5.3 | 4.50 | 0.8 | | AA194983 |
| IL-8 | 0.55 | 3.6 | 17 | 1.8 | 1.1 | AA102526 |
| interleukin enhancer binding factor 2 | 0.75 | 1.3 | 2.3 | 0.8 | 4.6 | AA894687 |
| interleukin enhancer binding factor 1 | 0.41 | 2.7 | | 5.3 | 2.5 | R56553 |
| cytokine inducible SH2-containing protein | 0.03 | 33 | 44 | 39 | 46 | AA427521 |
| IK cytokine, down-regulator of HLA II | 0.50 | 3.1 | 2.0 | 1.7 | 3.3 | R39227 |
| cytokine inducible SH2-containing Protein | 0.03 | 33 | 44 | 39 | 46 | AA427521 |
| IK cytokine, down-regulator of HLA II | 0.50 | 3.1 | 2.0 | 1.7 | 3.3 | R39227 |
| small inducible cytokine subfamily A (Cys-Cys), member 21 | 1.00 | 3.9 | | | 2.4 | AI922341 |
| TGFB inducible early growth response 2 | 0.90 | 2.4 | 2.1 | 0.9 | 1.1 | AI473938 |
| NK cell R | 1.02 | 2.5 | 0.7 | 0.3 | 1.0 | AA463248 |
| CCR6 | 0.14 | 4.5 | 7.8 | 6.9 | 7.8 | N57964 |
| cell adhesion molecule | 0.25 | 4.0 | 3.9 | 3.9 | 5.1 | R40400 |
| melanoma adhesion molecule | 0.05 | 7.9 | 20 | 43 | 29.1 | AA497002 |
| CD31 | 0.59 | 2.7 | 3.1 | 1.0 | 1.7 | R22412 |
| integrin, alpha 2 (CD49B, alpha 2 subunit of VLA-2 receptor | 1.00 | 0.9 | 2.4 | 3.6 | 0.9 | AA463257 |
| integrin, alpha 3 (antigen CD49C, alpha 3 subunit of VLA-3 receptor) | 0.94 | 0.8 | 2.5 | 1.9 | 1.1 | AA424695 |
| integrin, alpha E | 0.01 | 180 | 120 | 28 | 81 | AA425451 |
| integrin, beta 1 | 0.47 | 2.1 | 2.1 | 7.0 | 2.6 | W67174 |
| integrin, beta 3 | 0.55 | 2.7 | 2.8 | 1.8 | 1.0 | AA037229 |
| integrin, beta 3 | 0.57 | 2.6 | 1.4 | 1.8 | 2.0 | AA666269 |
| integrin, beta 4 | 0.65 | 0.8 | 2.2 | 4.9 | 1.5 | AA485668 |
| integrin beta 4 binding protein | 0.20 | 1.7 | 5.0 | 6.6 | 5.3 | AI017019 |
| calcium and integrin binding protein | 0.21 | 2.8 | 4.7 | 9.7 | 6.7 | AA487575 |
| disintegrin and metalloproteinase domain 8 | 0.46 | 3.1 | | 2.2 | 3.8 | AA279188 |
| disintegrin and metalloproteinase domain 9 | 0.94 | 1.1 | 2.3 | 3.6 | 0.5 | H59231 |
| disintegrin and metalloproteinase domain 10 | 0.49 | 1.5 | 2.1 | 3.3 | 2.2 | AA043347 |
| disintegrin and metalloproteinase domain 23 | 0.44 | 1.9 | 2.3 | 2.5 | 4.6 | H11006 |
| cadherin 1, type 1, E-cadherin (epithelial) | 0.42 | 8.1 | 2.2 | 2.4 | 7.3 | H97778 |
| cadherin 12, type 2 (N-cadherin 2) | 0.11 | 13 | 26 | 9.5 | | AI740827 |
| protocadherin 12 | 0.09 | 14.8 | 11.5 | 2.6 | 12.4 | AI652584 |
| protocadherin gamma subfamily C, 3 | 0.34 | 3.0 | 2.5 | 4.5 | 9.9 | R89615 |
| catenin (cadherin-associated protein), delta 1 | 0.86 | 1.2 | 2.2 | 2.4 | | AA025276 |
| laminin R 1 (67 kD, ribosomal protein SA) | 0.50 | 0.4 | 2.0 | 4.4 | 3.0 | AA629897 |
| killer cell lectin-like receptor subfamily C, member 2 | 0.11 | 9.7 | 9.0 | 4.1 | 13.4 | AA190627 |
| killer cell lectin-like receptor subfamily C, member 3 | 1.00 | 3.2 | 1.0 | 0.9 | 1.3 | W93370 |
| killer cell lectin-like receptor subfamily G, member 1 | 0.95 | 2.3 | 1.7 | 0.7 | 1.1 | AI433079 |
| C-type lectin-like receptor-2 | 0.45 | 2.1 | 8.0 | 2.2 | 5.3 | H70491 |
| CSF 3 R | 0.40 | 1.9 | 2.5 | 3.5 | 4.0 | AA458507 |
| macrophage stimulating 1 R | 1.00 | 1.7 | 2.3 | 0.4 | 0.7 | AA173454 |
| BMP R type IA | 0.72 | 1.9 | 2.8 | 0.3 | 1.4 | W15390 |

TABLE 21-continued

Polynucleotides up-regulated by peptide treatment of A549 epithelial cells[a].
The cationic peptides at concentrations of 50 μg/ml were shown to increase the expression of several polynucleotides. Peptide was incubated with the human A549 epithelial cells for 4 h and the RNA was isolated, converted into labeled cDNA probes and hybridized to Human cDNA arrays ID#PRHU03-S3. The intensity of polynucleotides in unstimulated cells is shown in the second column. The "Ratio Peptide: Unstimulated" columns refers to the intensity of polynucleotide expression in peptide-simulated cells divided by the intensity of unstimulated cells.

| Polynucleotide/Protein | Unstimulated Intensity | Ratio Peptide: Unstimulated | | | | Accession Number |
|---|---|---|---|---|---|---|
| | | ID 2 | ID 3 | ID 19 | ID 1 | |
| formyl peptide receptor 1 | 1.00 | 3.1 | 1.4 | 0.4 | | AA425767 |
| CD2 | 1.00 | 2.6 | 0.9 | 1.2 | 0.9 | AA927710 |
| CD36 | 0.18 | 8.2 | 5.5 | 6.2 | 2.5 | N39161 |
| vitamin D R | 0.78 | 2.5 | 1.3 | 1.1 | 1.4 | AA485226 |
| Human proteinase activated R-2 | 0.54 | 6.1 | 1.9 | 2.2 | | AA454652 |
| prostaglandin E receptor 3 (subtype EP3) | 0.25 | 4.1 | 4.9 | 3.8 | 4.9 | AA406362 |
| PDGF R beta polypeptide | 1.03 | 2.5 | 1.0 | 0.5 | 0.8 | R56211 |
| VIP R 2 | 1.00 | 3.1 | | | 2.0 | AI057229 |
| growth factor receptor-bound protein 2 | 0.51 | 2.2 | 2.0 | 2.4 | 0.3 | AA449831 |
| Mouse Mammary Tumor Virus Receptor homolog | 1.00 | 6.9 | | 16 | | W93891 |
| adenosine A2a R | 0.41 | 3.1 | 1.8 | 4.0 | 2.5 | N57553 |
| adenosine A3 R | 0.83 | 2.0 | 2.3 | 1.0 | 1.2 | AA863086 |
| T cell R delta locus | 0.77 | 2.7 | 1.3 | | 1.8 | AA670107 |
| prostaglandin E receptor 1 (subtype EP1) | 0.65 | 7.2 | | 6.0 | 1.5 | AA972293 |
| growth factor receptor-bound protein 14 | 0.34 | | 3.0 | 6.3 | 2.9 | R24266 |
| Epstein-Barr virus induced polynucleotide 2 | 0.61 | 1.6 | 2.4 | | 8.3 | AA037376 |
| complement component receptor 2 | 0.22 | 26 | 4.5 | 2.6 | 18.1 | AA521362 |
| endothelin receptor type A | 0.07 | 12 | 14 | 14 | 16 | AA450009 |
| v-SNARE R | 0.56 | 11 | 12 | 1.8 | | AA704511 |
| tyrosine kinase, non-receptor, 1 | 0.12 | 7.8 | 8.5 | 10 | 8.7 | AI936324 |
| receptor tyrosine kinase-like orphan receptor 2 | 0.40 | 7.3 | 5.0 | 1.6 | 2.5 | N94921 |
| protein tyrosine phosphatase, non-receptor type 3 | 1.02 | 1.0 | 13.2 | 0.5 | 0.8 | AA682684 |
| protein tyrosine phosphatase, non-receptor type 9 | 0.28 | 3.5 | 4.0 | 0.9 | 5.3 | AA434420 |
| protein tyrosine phosphatase, non-receptor type 11 | 0.42 | 2.9 | 2.4 | 2.2 | 3.0 | AA995560 |
| protein tyrosine phosphatase, non-receptor type 12 | 1.00 | 2.3 | 2.2 | 0.8 | 0.5 | AA446259 |
| protein tyrosine phosphatase, non-receptor type 13 | 0.58 | 1.7 | 2.4 | 3.6 | 1.7 | AA679180 |
| protein tyrosine phosphatase, non-receptor type 18 | 0.52 | 3.2 | 0.9 | 1.9 | 6.5 | AI668897 |
| protein tyrosine phosphatase, receptor type, A | 0.25 | 4.0 | 2.4 | 16.8 | 12.8 | H82419 |
| protein tyrosine phosphatase, receptor type, J | 0.60 | 3.6 | 3.2 | 1.6 | 1.0 | AA045326 |
| protein tyrosine phosphatase, receptor type, T | 0.73 | 1.2 | 2.8 | 3.0 | 1.4 | R52794 |
| protein tyrosine phosphatase, receptor type, U | 0.20 | 6.1 | 1.2 | 5.6 | 5.0 | AA644448 |
| protein tyrosine phosphatase, receptor type, C-associated protein | 1.00 | 5.1 | | | 2.4 | AA481547 |
| phospholipase A2 receptor 1 | 0.45 | 2.8 | 2.2 | 1.9 | 2.2 | AA086038 |
| MAP kinase-activated protein kinase 3 | 0.52 | 2.1 | 2.7 | 1.1 | 1.9 | W68281 |
| MAP kinase kinase 6 | 0.10 | 18 | 9.6 | | 32 | H07920 |
| MAP kinase kinase 5 | 1.00 | 3.0 | 5.2 | 0.8 | 0.2 | W69649 |
| MAP kinase 7 | 0.09 | | 11.5 | 12 | 33 | H39192 |
| MAP kinase 12 | 0.49 | 2.1 | 1.7 | 2.2 | 2.0 | AI936909 |
| G protein-coupled receptor 4 | 0.40 | 3.7 | 3.0 | 2.4 | 2.5 | AI719098 |
| G protein-coupled receptor 49 | 0.05 | | 19 | 19 | 27 | AA460530 |
| G protein-coupled receptor 55 | 0.08 | 19 | 15 | 12 | | N58443 |
| G protein-coupled receptor 75 | 0.26 | 5.2 | 3.1 | 7.1 | 3.9 | H84878 |
| G protein-coupled receptor 85 | 0.20 | 6.8 | 5.4 | 4.9 | 5.0 | N62306 |
| regulator of G-protein signalling 20 | 0.02 | 48 | 137 | 82 | | AI264190 |
| regulator of G-protein signalling 6 | 0.27 | | 3.7 | 8.9 | 10.6 | R39932 |
| BCL2-interacting killer (apoptosis-inducing) | 1.00 | 1.9 | | 5.2 | | AA291323 |

TABLE 21-continued

Polynucleotides up-regulated by peptide treatment of A549 epithelial cells[a].
The cationic peptides at concentrations of 50 μg/ml were shown to increase the expression of several polynucleotides. Peptide was incubated with the human A549 epithelial cells for 4 h and the RNA was isolated, converted into labeled cDNA probes and hybridized to Human cDNA arrays ID#PRHU03-S3. The intensity of polynucleotides in unstimulated cells is shown in the second column. The "Ratio Peptide: Unstimulated" columns refers to the intensity of polynucleotide expression in peptide-simulated cells divided by the intensity of unstimulated cells.

| Polynucleotide/Protein | Unstimulated Intensity | ID 2 | ID 3 | ID 19 | ID 1 | Accession Number |
|---|---|---|---|---|---|---|
| apoptosis inhibitor 5 | 0.56 | 2.8 | 1.6 | 2.4 | 1.8 | AI972925 |
| caspase 6, apoptosis-related cysteine protease | 0.79 | 0.7 | 2.6 | 1.3 | 2.8 | W45688 |
| apoptosis-related protein PNAS-1 | 0.46 | 2.2 | 1.4 | 2.3 | 2.9 | AA521316 |
| caspase 8, apoptosis-related cysteine protease | 0.95 | 2.2 | 1.0 | 0.6 | 2.0 | AA448468 |

TABLE 22

Polynucleotides down-regulated by peptide treatment of A549 epithelial cells[a].
The cationic peptides at concentrations of 50 μg/ml were shown to decrease the expression of several polynucleotides. Peptide was incubated with the human A549 epithelial cells for 4 h and the RNA was isolated, converted into labeled cDNA probes and hybridized to Human cDNA arrays ID#PRHU03-S3. The intensity of polynucleotides in unstimulated cells is shown in the second column. The "Ratio Peptide: Unstimulated" columns refers to the intensity of polynucleotide expression in peptide-simulated cells divided by the intensity of unstimulated cells.

| Polynucleotide/Protein | Unstimulated Intensity | ID 2 | ID 3 | ID 19 | ID 1 | Accession Number |
|---|---|---|---|---|---|---|
| TLR 1 | 3.22 | 0.35 | 0.31 | 0.14 | 0.19 | AI339155 |
| TLR 2 | 2.09 | 0.52 | 0.31 | 0.48 | 0.24 | T57791 |
| TLR 5 | 8.01 | 0.12 | 0.39 | | | N41021 |
| TLR 7 | 5.03 | 0.13 | 0.11 | 0.20 | 0.40 | N30597 |
| TNF receptor-associated factor 2 | 0.82 | 1.22 | 0.45 | 2.50 | 2.64 | T55353 |
| TNF receptor-associated factor 3 | 3.15 | 0.15 | | 0.72 | 0.32 | AA504259 |
| TNF receptor superfamily, member 12 | 4.17 | 0.59 | 0.24 | | 0.02 | W71984 |
| TNF R superfamily, member 17 | 2.62 | | 0.38 | 0.55 | 0.34 | AA987627 |
| TRAF and TNF receptor-associated protein | 1.33 | 0.75 | 0.22 | 0.67 | 0.80 | AA488650 |
| IL-1 receptor, type I | 1.39 | 0.34 | 0.72 | 1.19 | 0.34 | AA464526 |
| IL-2 receptor, alpha | 2.46 | 0.41 | 0.33 | 0.58 | | AA903183 |
| IL-2 receptor, gamma (severe combined immunodeficiency) | 3.34 | 0.30 | 0.24 | | 0.48 | N54821 |
| IL-12 receptor, beta 2 | 4.58 | 0.67 | 0.22 | | | AA977194 |
| IL-18 receptor 1 | 1.78 | 0.50 | 0.42 | 0.92 | 0.56 | AA482489 |
| TGF beta receptor III | 2.42 | 0.91 | 0.24 | 0.41 | 0.41 | H62473 |
| leukotriene b4 receptor (chemokine receptor-like 1) | 1.00 | | 1.38 | 4.13 | 0.88 | AI982606 |
| small inducible cytokine subfamily A (Cys-Cys), member 18 | 2.26 | 0.32 | | 0.44 | 1.26 | AA495985 |
| small inducible cytokine subfamily A (Cys-Cys), member 20 | 2.22 | 0.19 | 0.38 | 0.45 | 0.90 | AI285199 |
| small inducible cytokine subfamily A (Cys-Cys), member 23 | 2.64 | 0.38 | 0.31 | 1.53 | | AA916836 |
| small inducible cytokine subfamily B (Cys-X-Cys), member 6 (granulocyte chemotactic protein 2) | 3.57 | 0.11 | 0.06 | 0.28 | 0.38 | AI889554 |
| small inducible cytokine subfamily B (Cys-X-Cys), member 10 | 2.02 | 0.50 | 1.07 | 0.29 | 0.40 | AA878880 |
| small inducible cytokine A3 (homologous to mouse Mip-1a) | 2.84 | 1.79 | 0.32 | 0.35 | | AA677522 |
| cytokine-inducible kinase | 2.70 | 0.41 | 0.37 | 0.37 | 0.34 | AA489234 |
| complement component C1q receptor | 1.94 | 0.46 | 0.58 | 0.51 | 0.13 | AI761788 |
| cadherin 11, type 2, OB-cadherin (osteoblast) | 2.00 | 0.23 | 0.57 | 0.30 | 0.50 | AA136983 |
| cadherin 3, type 1, P-cadherin (placental) | 2.11 | 0.43 | 0.53 | 0.10 | 0.47 | AA425217 |

TABLE 22-continued

Polynucleotides down-regulated by peptide treatment of A549 epithelial cells[a].
The cationic peptides at concentrations of 50 μg/ml were shown to decrease the expression of several polynucleotides. Peptide was incubated with the human A549 epithelial cells for 4 h and the RNA was isolated, converted into labeled cDNA probes and hybridized to Human cDNA arrays ID#PRHU03-S3. The intensity of polynucleotides in unstimulated cells is shown in the second column. The "Ratio Peptide: Unstimulated" columns refers to the intensity of polynucleotide expression in peptide-simulated cells divided by the intensity of unstimulated cells.

| Polynucleotide/Protein | Unstimulated Intensity | Ratio Peptide: Unstimulated | | | | Accession Number |
|---|---|---|---|---|---|---|
| | | ID 2 | ID 3 | ID 19 | ID 1 | |
| cadherin, EGF LAG seven-pass G-type receptor 2, flamingo (Drosophila) homolog | 1.67 | 0.42 | 0.41 | 1.21 | 0.60 | H39187 |
| cadherin 13, H-cadherin (heart) | 1.78 | 0.37 | 0.40 | 0.56 | 0.68 | R41787 |
| selectin L (lymphocyte adhesion molecule 1) | 4.43 | 0.03 | 0.23 | 0.61 | | H00662 |
| vascular cell adhesion molecule 1 | 1.40 | 0.20 | 0.72 | 0.77 | 0.40 | H16591 |
| intercellular adhesion molecule 3 | 1.00 | 0.12 | 0.31 | 2.04 | 1.57 | AA479188 |
| integrin, alpha 1 | 2.42 | 0.41 | 0.26 | | 0.56 | AA450324 |
| integrin, alpha 7 | 2.53 | 0.57 | 0.39 | 0.22 | 0.31 | AA055979 |
| integrin, alpha 9 | 1.16 | 0.86 | 0.05 | 0.01 | 2.55 | AA865557 |
| integrin, alpha 10 | 1.00 | 0.33 | 0.18 | 1.33 | 2.25 | AA460959 |
| integrin, beta 5 | 1.00 | 0.32 | 1.52 | 1.90 | 0.06 | AA434397 |
| integrin, beta 8 | 3.27 | 0.10 | 1.14 | 0.31 | 0.24 | W56754 |
| disintegrin and metalloproteinase domain 18 | 2.50 | 0.40 | 0.29 | 0.57 | 0.17 | AI205675 |
| disintegrin-like and metalloprotease with thrombospondin type 1 motif, 3 | 2.11 | 0.32 | 0.63 | 0.47 | 0.35 | AA398492 |
| disintegrin-like and metalloprotease with thrombospondin type 1 motif, 5 | 1.62 | 0.39 | 0.42 | 1.02 | 0.62 | AI375048 |
| T-cell receptor interacting molecule | 1.00 | 0.41 | 1.24 | 1.41 | 0.45 | AI453185 |
| diphtheria toxin receptor (heparin-binding epidermal growth factor-like growth factor) | 1.62 | 0.49 | 0.85 | 0.62 | 0.15 | R45640 |
| vasoactive intestinal peptide receptor 1 | 2.31 | 0.43 | 0.31 | 0.23 | 0.54 | H73241 |
| Fc fragment of IgG, low affinity IIIb, receptor for (CD16) | 3.85 | −0.20 | 0.26 | 0.76 | 0.02 | H20822 |
| Fc fragment of IgG, low affinity IIb, receptor for (CD32) | 1.63 | 0.27 | 0.06 | 1.21 | 0.62 | R68106 |
| Fc fragment of IgE, high affinity I, receptor for; alpha polypeptide | 1.78 | 0.43 | 0.00 | 0.56 | 0.84 | AI676097 |
| leukocyte immunoglobulin-like receptor, subfamily A | 2.25 | 0.44 | 0.05 | 0.38 | 0.99 | N63398 |
| leukocyte immunoglobulin-like receptor, subfamily B (with TM and ITIM domains), member 3 | 14.21 | | | 1.10 | 0.07 | AI815229 |
| leukocyte immunoglobulin-like receptor, subfamily B (with TM and ITIM domains), member 4 | 2.31 | 0.75 | 0.43 | 0.19 | 0.40 | AA076350 |
| leukocyte immunoglobulin-like receptor, subfamily B | 1.67 | 0.35 | 0.60 | 0.18 | 0.90 | H54023 |
| peroxisome proliferative activated receptor, alpha | 1.18 | 0.38 | 0.85 | 0.87 | 0.26 | AI739498 |
| protein tyrosine phosphatase, receptor type, f polypeptide (PTPRF), interacting protein (liprin), α1 | 2.19 | 0.43 | | 1.06 | 0.46 | N49751 |
| protein tyrosine phosphatase, receptor type, C | 1.55 | 0.44 | 0.64 | 0.30 | 0.81 | H74265 |
| protein tyrosine phosphatase, receptor type, E | 2.08 | 0.23 | 0.37 | 0.56 | 0.48 | AA464542 |
| protein tyrosine phosphatase, receptor type, N polypeptide 2 | 2.27 | 0.02 | 0.44 | | 0.64 | AA464590 |
| protein tyrosine phosphatase, receptor type, H | 2.34 | 0.11 | 0.43 | 0.24 | 0.89 | AI924306 |
| protein tyrosine phosphatase, receptor-type, Z polypeptide 1 | 1.59 | 0.63 | 0.34 | 0.72 | 0.35 | AA476461 |
| protein tyrosine phosphatase, non-receptor type 21 | 1.07 | 0.94 | 0.43 | 0.25 | 1.13 | H03504 |
| MAP kinase 8 interacting protein 2 | 1.70 | 0.07 | 0.85 | 0.47 | 0.59 | AA418293 |
| MAP kinase kinase kinase 4 | 1.27 | 0.37 | 0.79 | 1.59 | −5.28 | AA402447 |
| MAP kinase kinase kinase 14 | 1.00 | 0.34 | 0.66 | 2.10 | 1.49 | W61116 |
| MAP kinase 8 interacting protein 2 | 2.90 | 0.16 | 0.35 | 0.24 | 0.55 | AI202738 |
| MAP kinase kinase kinase 12 | 1.48 | 0.20 | 0.91 | 0.58 | 0.68 | AA053674 |
| MAP kinase kinase kinase kinase 3 | 2.21 | 0.45 | 0.20 | 1.03 | 0.41 | AA043537 |
| MAP kinase kinase kinase 6 | 2.62 | 0.37 | 0.38 | | 0.70 | AW084649 |

TABLE 22-continued

Polynucleotides down-regulated by peptide treatment of A549 epithelial cells[a].
The cationic peptides at concentrations of 50 μg/ml were shown to decrease the expression of several polynucleotides. Peptide was incubated with the human A549 epithelial cells for 4 h and the RNA was isolated, converted into labeled cDNA probes and hybridized to Human cDNA arrays ID#PRHU03-S3. The intensity of polynucleotides in unstimulated cells is shown in the second column. The "Ratio Peptide: Unstimulated" columns refers to the intensity of polynucleotide expression in peptide-simulated cells divided by the intensity of unstimulated cells.

| Polynucleotide/Protein | Unstimulated Intensity | Ratio Peptide: Unstimulated | | | | Accession Number |
|---|---|---|---|---|---|---|
| | | ID 2 | ID 3 | ID 19 | ID 1 | |
| MAP kinase kinase kinase kinase 4 | 1.04 | 0.96 | 0.09 | 0.29 | 2.79 | AA417711 |
| MAP kinase kinase kinase 11 | 1.53 | 0.65 | 0.41 | 0.99 | 0.44 | R80779 |
| MAP kinase kinase kinase 10 | 1.32 | 1.23 | 0.27 | 0.50 | 0.76 | H01340 |
| MAP kinase 9 | 2.54 | 0.57 | 0.39 | 0.16 | 0.38 | AA157286 |
| MAP kinase kinase kinase 1 | 1.23 | 0.61 | 0.42 | 0.81 | 1.07 | AI538525 |
| MAP kinase kinase kinase 8 | 0.66 | 1.52 | 1.82 | 9.50 | 0.59 | W56266 |
| MAP kinase-activated protein kinase 3 | 0.52 | 2.13 | 2.68 | 1.13 | 1.93 | W68281 |
| MAP kinase kinase 2 | 0.84 | 1.20 | 3.35 | 0.02 | 1.31 | AA425826 |
| MAP kinase kinase kinase 7 | 1.00 | 0.97 | | 1.62 | 7.46 | AA460969 |
| MAP kinase 7 | 0.09 | | 11.45 | 11.80 | 33.43 | H39192 |
| MAP kinase kinase 6 | 0.10 | 17.83 | 9.61 | | 32.30 | H07920 |
| regulator of G-protein signalling 5 | 3.7397 | 0.27 | 0.06 | 0.68 | 0.18 | AA668470 |
| regulator of G-protein signalling 13 | 1.8564 | 0.54 | 0.45 | 0.07 | 1.09 | H70047 |
| G protein-coupled receptor | 1.04 | 1.84 | 0.16 | 0.09 | 0.96 | R91916 |
| G protein-coupled receptor 17 | 1.78 | 0.32 | 0.56 | 0.39 | 0.77 | AI953187 |
| G protein-coupled receptor kinase 7 | 2.62 | | 0.34 | 0.91 | 0.38 | AA488413 |
| orphan seven-transmembrane receptor, chemokine related | 7.16 | 1.06 | 0.10 | 0.11 | 0.14 | AI131555 |
| apoptosis antagonizing transcription factor | 1.00 | 0.28 | 2.50 | 1.28 | 0.19 | AI439571 |
| caspase 1, apoptosis-related cysteine protease (interleukin 1, beta, convertase) | 2.83 | 0.44 | | 0.33 | 0.35 | T95052 |
| programmed cell death 8 (apoptosis-inducing factor) | 1.00 | 1.07 | 0.35 | 1.94 | 0.08 | AA496348 |

TABLE 23

Pro-inflammatory polynucleotides up-regulated by peptide treatment of A549 cells.
The cationic peptides at concentrations of 50 μg/ml were shown to increase the expression of certain pro-inflammatory polynucleotides (data is a subset of Table 21). Peptide was incubated with the human A549 epithelial cells for 4 h and the RNA was isolated, converted into labeled cDNA probes and hybridized to Human cDNA arrays ID#PRHU03-S3. The intensity of polynucleotides in unstimulated cells is shown in the second column. The "Ratio Peptide: Unstimulated" columns refers to the intensity of polynucleotide expression in peptide-simulated cells divided by the intensity of unstimulated cells.

| Polynucleotide/Protein and function | Unstim Intensity | Ratio Peptide: Unstimulated | | | | Accession Number |
|---|---|---|---|---|---|---|
| | | ID 2 | ID 3 | ID 19 | ID 1 | |
| IL-11 Rα; Receptor for pro-inflammatory cytokine, inflammation | 0.55 | 2.39 | 0.98 | 4.85 | 1.82 | AA454657 |
| IL-17 R; Receptor for IL-17, an inducer of cytokine production in epithelial cells | 0.54 | 2.05 | 1.97 | 1.52 | 1.86 | AW029299 |
| small inducible cytokine subfamily A, member 21; a chemokine | 1.00 | 3.88 | | | 2.41 | AI922341 |
| CD31; Leukocyte and cell to cell adhesion (PECAM) | 0.59 | 2.71 | 3.13 | 1.01 | 1.68 | R22412 |
| CCR6; Receptor for chemokine MIP-3α | 0.14 | 4.51 | 7.75 | 6.92 | 7.79 | N57964 |
| integrin, alpha 2 (CD49B, alpha 2 subunit of VLA-2 receptor; Adhesion to leukocytes | 1.00 | 0.89 | 2.44 | 3.62 | 0.88 | AA463257 |
| integrin, alpha 3 (antigen CD49C, alpha 3 subunit of VLA-3 receptor); Leukocyte Adhesion | 0.94 | 0.79 | 2.51 | 1.88 | 1.07 | AA424695 |
| integrin, alpha E; Adhesion | 0.01 | 179.33 | 120.12 | 28.48 | 81.37 | AA425451 |
| integrin, beta 4; Leukocyte adhesion | 0.65 | 0.79 | 2.17 | 4.94 | 1.55 | AA485668 |
| C-type lectin-like receptor-2;Leukocyte adhesion | 0.45 | 2.09 | 7.92 | 2.24 | 5.29 | H70491 |

TABLE 24

Pro-inflammatory polynucleotides down-regulated by peptide treatment of A549 cells.
The cationic peptides at concentrations of 50 μg/ml were shown to decrease the expression of certain pro-inflammatory polynucleotides (data is a subset of Table 22). Peptide was incubated with the human A549 epithelial cells for 4 h and the RNA was isolated, converted into labeled cDNA probes and hybridized to Human cDNA arrays ID#PRHU03-S3. The intensity of polynucleotides in unstimulated cells is shown in the second column. The "Ratio Peptide: Unstimulated" columns refers to the intensity of polynucleotide expression in peptide-simulated cells divided by the intensity of unstimulated cells.

| Polynucleotide/Protein; Function | Unstim Intensity | Ratio Peptide: Unstimulated | | | | Accession Number |
|---|---|---|---|---|---|---|
| | | ID 2 | ID 3 | ID 19 | ID 1 | |
| Toll-like receptor (TLR) 1; Response to gram positive bacteria | 3.22 | 0.35 | 0.31 | 0.14 | 0.19 | AI339155 |
| TLR 2; Response to gram positive bacteria and yeast | 2.09 | 0.52 | 0.31 | 0.48 | 0.24 | T57791 |
| TLR 5; May augment other TLR responses, Responsive to flagellin | 8.01 | 0.12 | 0.39 | | | N41021 |
| TLR 7; Putative host defence mechanism | 5.03 | 0.13 | 0.11 | 0.20 | 0.40 | N30597 |
| TNF receptor-associated factor 2; Inflammation | 0.82 | 1.22 | 0.45 | 2.50 | 2.64 | T55353 |
| TNF receptor-associated factor 3; Inflammation | 3.15 | 0.15 | | 0.72 | 0.32 | AA504259 |
| TNF receptor superfamily, member 12; Inflammation | 4.17 | 0.59 | 0.24 | | 0.02 | W71984 |
| TNF R superfamily, member 17; Inflammation | 2.62 | | 0.38 | 0.55 | 0.34 | AA987627 |
| TRAF and TNF receptor-associated protein; TNF signalling | 1.33 | 0.75 | 0.22 | 0.67 | 0.80 | AA488650 |
| small inducible cytokine subfamily A, member 18; Chemokine | 2.26 | 0.32 | | 0.44 | 1.26 | AA495985 |
| small inducible cytokine subfamily A, member 20; Chemokine | 2.22 | 0.19 | 0.38 | 0.45 | 0.90 | AI285199 |
| small inducible cytokine subfamily A, member 23; Chemokine | 2.64 | 0.38 | 0.31 | 1.53 | | AA916836 |
| small inducible cytokine subfamily B, member 6 (granulocyte chemotactic protein); Chemokine | 3.57 | 0.11 | 0.06 | 0.28 | 0.38 | AI889554 |
| small inducible cytokine subfamily B, member 10; Chemokine | 2.02 | 0.50 | 1.07 | 0.29 | 0.40 | AA878880 |
| small inducible cytokine A3 (homologous to mouse Mip-1α); Chemokine | 2.84 | 1.79 | 0.32 | 0.35 | | AA677522 |
| IL-12 receptor, beta 2; Interleukin and Interferon receptor | 4.58 | 0.67 | 0.22 | | | AA977194 |
| IL-18 receptor 1; Induces IFN-γ | 1.78 | 0.50 | 0.42 | 0.92 | 0.56 | AA482489 |
| selectin L (lymphocyte adhesion molecule 1); Leukocyte adhesion | 4.43 | 0.03 | 0.23 | 0.61 | | H00662 |
| vascular cell adhesion molecule 1; Leukocyte adhesion | 1.40 | 0.20 | 0.72 | 0.77 | 0.40 | H16591 |
| intercellular adhesion molecule 3; Leukocyte adhesion | 1.00 | 0.12 | 0.31 | 2.04 | 1.57 | AA479188 |
| integrin, alpha 1; Leukocyte adhesion | 2.42 | 0.41 | 0.26 | | 0.56 | AA450324 |

TABLE 25

Anti-inflammatory polynucleotides up-regulated by peptide treatment of A549 cells.
The cationic peptides at concentrations of 50 μg/ml were shown to increase the expression of certain anti-inflammatory polynucleotides (data is a subset of Table 21). Peptide was incubated with the human A549 epithelial cells for 4 h and the RNA was isolated, converted into labeled cDNA probes and hybridized to Human cDNA arrays ID#PRHU03-S3. The intensity of polynucleotides in unstimulated cells is shown in the second column. The "Ratio Peptide: Unstimulated" columns refers to the intensity of polynucleotide expression in peptide-simulated cells divided by the intensity of unstimulated cells.

| Polynucleotide/Protein; Function | Unstim Intensity | Ratio Peptide: Unstimulated | | | | Accession Number |
|---|---|---|---|---|---|---|
| | | ID 2 | ID 3 | ID 19 | ID 1 | |
| IL-1 R antagonist homolog 1; Inhibitor of septic shock | 0.00 | 3085.96 | 1855.90 | 869.57 | | AI167887 |
| IL-10 R beta; Receptor for cytokine synthesis inhibitor | 0.53 | 2.51 | 1.56 | 1.88 | 3.10 | AA486393 |
| TNF R, member 1B; Apoptosis | 0.28 | 17.09 | 3.01 | 14.93 | 3.60 | AA150416 |
| TNF R, member 5; Apoptosis (CD40L) | 33.71 | 2.98 | 0.02 | | | H98636 |
| TNF R, member 11b; Apoptosis | 1.00 | 5.29 | 4.50 | 0.78 | | AA194983 |

TABLE 25-continued

Anti-inflammatory polynucleotides up-regulated by peptide treatment of A549 cells.
The cationic peptides at concentrations of 50 μg/ml were shown to increase the expression of certain anti-inflammatory polynucleotides (data is a subset of Table 21). Peptide was incubated with the human A549 epithelial cells for 4 h and the RNA was isolated, converted into labeled cDNA probes and hybridized to Human cDNA arrays ID#PRHU03-S3. The intensity of polynucleotides in unstimulated cells is shown in the second column. The "Ratio Peptide: Unstimulated" columns refers to the intensity of polynucleotide expression in peptide-simulated cells divided by the intensity of unstimulated cells.

| Polynucleotide/Protein; Function | Unstim Intensity | Ratio Peptide: Unstimulated | | | | Accession Number |
|---|---|---|---|---|---|---|
| | | ID 2 | ID 3 | ID 19 | ID 1 | |
| IK cytokine, down-regulator of HLA II; Inhibits antigen presentation | 0.50 | 3.11 | 2.01 | 1.74 | 3.29 | R39227 |
| TGFB inducible early growth response 2; anti-inflammatory cytokine | 0.90 | 2.38 | 2.08 | 0.87 | 1.11 | AI473938 |
| CD2; Adhesion molecule, binds LFAp3 | 1.00 | 2.62 | 0.87 | 1.15 | 0.88 | AA927710 |

TABLE 26

Anti-inflammatory polynucleotides down-regulated by peptide treatment of A549 cells.
The cationic peptides at concentrations of 50 μg/ml were shown to increase the expression of certain anti-inflammatory polynucleotides (data is a subset of Table 21). Peptide was incubated with the human A549 epithelial cells for 4 h and the RNA was isolated, converted into labeled cDNA probes and hybridized to Human cDNA arrays ID#PRHU03-S3. The intensity of polynucleotides in unstimulated cells is shown in the second column. The "Ratio Peptide: Unstimulated" columns refers to the intensity of polynucleotide expression in peptide-simulated cells divided by the intensity of unstimulated cells.

| Polynucleotide/Protein; Function | Unstim Intensity | Ratio Peptide: Unstimulated | | | | Accession Number |
|---|---|---|---|---|---|---|
| | | ID 2 | ID 3 | ID 19 | ID 1 | |
| MAP kinase 9 | 2.54 | 0.57 | 0.39 | 0.16 | 0.38 | AA157286 |

TABLE 27

Polynucleotides up-regulated by SEQ ID NO: 6, in primary human macrophages. The peptide SEQ ID NO: 6 at a concentration of 50 μg/ml was shown to increase the expression of many polynucleotides. Peptide was incubated with the human macrophages for 4 h and the RNA was isolated, converted into labeled cDNA probes and hybridized to Human Operon arrays (PRHU04). The intensity of polynucleotides in unstimulated cells is shown in the second column. The "Ratio peptide treated: Control" columns refer to the intensity of polynucleotide expression in peptide-simulated cells divided by the intensity of unstimulated cells.

| Gene (Accession Number) | Control: Unstimulated cells | Ratio peptide treated: control |
|---|---|---|
| proteoglycan 2 (Z26248) | 0.69 | 9.3 |
| Unknown (AK001843) | 26.3 | 8.2 |
| phosphorylase kinase alpha 1 (X73874) | 0.65 | 7.1 |
| actinin, alpha 3 (M86407) | 0.93 | 6.9 |
| DKFZP586B2420 protein (AL050143) | 0.84 | 5.9 |
| Unknown (AL109678) | 0.55 | 5.6 |
| transcription factor 21 (AF047419) | 0.55 | 5.4 |
| Unknown (A433612) | 0.62 | 5.0 |
| chromosome condensation 1-like (AF060219) | 0.69 | 4.8 |
| Unknown (AL137715) | 0.66 | 4.4 |
| apoptosis inhibitor 4 (U75285) | 0.55 | 4.2 |
| TERF1 (TRF1)-interacting nuclear factor 2 (NM_012461) | 0.73 | 4.2 |
| LINE retrotransposable element 1 (M22333) | 6.21 | 4.0 |
| 1-acylglycerol-3-phosphate O-acyltransferase 1 (U56417) | 0.89 | 4.0 |
| Vacuolar proton-ATPase, subunit D; V-ATPase, subunit D (X71490) | 1.74 | 4.0 |
| KIAA0592 protein (AB011164) | 0.70 | 4.0 |
| potassium voltage-gated channel KQT-like subfamily member 4 (AF105202) | 0.59 | 3.9 |
| CDC14 homolog A (AF000367) | 0.87 | 3.8 |

TABLE 27-continued

Polynucleotides up-regulated by SEQ ID NO: 6, in primary human macrophages. The peptide SEQ ID NO: 6 at a concentration of 50 μg/ml was shown to increase the expression of many polynucleotides. Peptide was incubated with the human macrophages for 4 h and the RNA was isolated, converted into labeled cDNA probes and hybridized to Human Operon arrays (PRHU04). The intensity of polynucleotides in unstimulated cells is shown in the second column. The "Ratio peptide treated: Control" columns refer to the intensity of polynucleotide expression in peptide-simulated cells divided by the intensity of unstimulated cells.

| Gene (Accession Number) | Control: Unstimulated cells | Ratio peptide treated: control |
|---|---|---|
| histone fold proteinCHRAC17 (AF070640) | 0.63 | 3.8 |
| Cryptochrome 1 (D83702) | 0.69 | 3.8 |
| pancreatic zymogen granule membrane associated protein (AB035541) | 0.71 | 3.7 |
| Sp3 transcription factor (X68560) | 0.67 | 3.6 |
| hypothetical protein FLJ20495 (AK000502) | 0.67 | 3.5 |
| E2F transcription factor 5, p130-binding (U31556) | 0.56 | 3.5 |
| hypothetical protein FLJ20070 (AK000077) | 1.35 | 3.4 |
| glycoprotein IX (X52997) | 0.68 | 3.4 |
| KIAA1013 protein (AB023230) | 0.80 | 3.4 |
| eukaryotic translation initiation factor 4A, isoform 2 (AL137681) | 2.02 | 3.4 |
| FYN-binding protein (AF198052) | 1.04 | 3.3 |
| guanine nucleotide binding protein, gamma transducing activity polypeptide 1 (U41492) | 0.80 | 3.3 |
| glypican 1 (X54232) | 0.74 | 3.2 |
| mucosal vascular addressin cell adhesion molecule 1 (U43628) | 0.65 | 3.2 |
| lymphocyte antigen (M38056) | 0.70 | 3.2 |
| H1 histone family, member 4 (M60748) | 0.81 | 3.0 |
| translational inhibitor protein p14.5 (X95384) | 0.78 | 3.0 |
| hypothetical protein FLJ20689 (AB032978) | 1.03 | 2.9 |
| KIAA1278 protein (AB03104) | 0.80 | 2.9 |
| unknown (AL031864) | 0.95 | 2.9 |
| chymotrypsin-like protease (X71877) | 3.39 | 2.9 |
| calumenin (NM_001219) | 2.08 | 2.9 |
| protein kinase, cAMP-dependent, regulatory, type I, beta (M65066) | 7.16<br>7.16 | 2.9<br>2.9 |
| POU domain, class 4, transcription factor 2 (U06233) | 0.79 | 2.8 |
| POU domain, class 2, associating factor 1 (Z49194) | 1.09 | 2.8 |
| KIAA0532 protein (AB011104) | 0.84 | 2.8 |
| unknown (AF068289) | 1.01 | 2.8 |
| unknown (AL117643) | 0.86 | 2.7 |
| cathepsin E (M84424) | 15.33 | 2.7 |
| matrix metalloproteinase 23A (AF056200) | 0.73 | 2.7 |
| interferon receptor 2 (L42243) | 0.70 | 2.5 |
| MAP kinase kinase 1 (L11284) | 0.61 | 2.4 |
| protein kinase C, alpha (X52479) | 0.76 | 2.4 |
| c-Cbl-interacting protein (AF230904) | 0.95 | 2.4 |
| c-fos induced growth factor (Y12864) | 0.67 | 2.3 |
| cyclin-dependent kinase inhibitor 1B (S76988) | 0.89 | 2.2 |
| zinc finger protein 266 (X78924) | 1.67 | 2.2 |
| MAP kinase 14 (L35263) | 1.21 | 2.2 |
| KIAA0922 protein (AB023139) | 0.96 | 2.1 |
| bone morphogenetic protein 1 (NM_006129) | 1.10 | 2.1 |
| NADH dehydrogenase 1 alpha subcomplex, 10 (AF087661) | 1.47 | 2.1 |
| bone morphogenetic protein receptor, type IB (U89326) | 0.50 | 2.1 |
| interferon regulatory factor 2 (NM_002199) | 1.46 | 2.0 |
| protease, serine, 21 (AB031331) | 0.89 | 2.0 |

TABLE 28

Polynucleotides down-regulated by SEQ ID NO: 6, in primary human macrophages. The peptide SEQ ID NO: 6 at a concentration of 50 μg/ml was shown to increase the expression of many polynucleotides. Peptide was incubated with the human macrophages for 4 h and the RNA was isolated, converted into labeled cDNA probes and hybridized to Human Operon arrays (PRHU04). The intensity of polynucleotides in unstimulated cells is shown in the second column. The "Ratio of Peptide: Control" columns refer to the intensity of polynucleotide expression in peptide-simulated cells divided by the intensity of unstimulated cells.

| Gene (Accession Number) | Control: Unstimulated cells | Ratio peptide treated: control |
|---|---|---|
| Unknown (AL049263) | 17 | 0.06 |
| integrin-linked kinase (U40282) | 2.0 | 0.13 |
| KIAA0842 protein (AB020649) | 1.1 | 0.13 |
| Unknown (AB037838) | 13 | 0.14 |
| Granulin (AF055008) | 8.6 | 0.14 |
| glutathione peroxidase 3 (NM_002084) | 1.2 | 0.15 |
| KIAA0152 gene product (D63486) | 0.9 | 0.17 |
| TGFB1-induced anti-apoptotic factor 1 (D86970) | 0.9 | 0.19 |
| disintegrin protease (Y13323) | 1.5 | 0.21 |
| proteasome subunit beta type 7 (D38048) | 0.7 | 0.22 |
| cofactor required for Sp1 transcriptional activation subunit 3 (AB033042) | 0.9 | 0.23 |
| TNF receptor superfamily, member 14 (U81232) | 0.8 | 0.26 |
| proteasome 26S subunit non-ATPase 8 (D38047) | 1.1 | 0.28 |
| proteasome subunit beta type, 4 (D26600) | 0.7 | 0.29 |
| TNF receptor superfamily member 1B (M32315) | 1.7 | 0.29 |
| cytochrome c oxidase subunit Vic (X13238) | 3.3 | 0.30 |
| S100 calcium-binding protein A4 (M80563) | 3.8 | 0.31 |
| proteasome subunit alpha type, 6 (X59417) | 2.9 | 0.31 |
| proteasome 26S subunit non-ATPase, 10 (AL031177) | 1.0 | 0.32 |
| MAP kinase kinase kinase 2 (NM_006609) | 0.8 | 0.32 |
| ribosomal protein L11 (X79234) | 5.5 | 0.32 |
| matrix metalloproteinase 14 (Z48481) | 1.0 | 0.32 |
| proteasome subunit beta type, 5 (D29011) | 1.5 | 0.33 |
| MAP kinase-activated protein kinase 2 (U12779) | 1.5 | 0.34 |
| caspase 3 (U13737) | 0.5 | 0.35 |
| jun D proto-oncogene (X56681) | 3.0 | 0.35 |
| proteasome 26S subunit, ATPase, 3 (M34079) | 1.3 | 0.35 |
| IL-1 receptor-like 1 (AB012701) | 0.7 | 0.35 |
| interferon alpha-inducible protein (AB019565) | 13 | 0.35 |
| SDF receptor 1 (NM_012428) | 1.6 | 0.35 |
| Cathepsin D (M63138) | 46 | 0.36 |
| MAP kinase kinase 3 (D87116) | 7.4 | 0.37 |
| TGF, beta-induced, (M77349) | 1.8 | 0.37 |
| TNF receptor superfamily, member 10b (AF016266) | 1.1 | 0.37 |
| proteasome subunit beta type, 6 (M34079) | 1.3 | 0.38 |
| nuclear receptor binding protein (NM_013392) | 5.2 | 0.38 |
| Unknown (AL050370) | 1.3 | 0.38 |
| protease inhibitor 1 alpha-1-antitrypsin (X01683) | 0.7 | 0.40 |
| proteasome subunit alpha type, 7 (AF054185) | 5.6 | 0.40 |
| LPS-induced TNF-alpha factor (NM_004862) | 5.3 | 0.41 |
| transferrin receptor (X01060) | 14 | 0.42 |
| proteasome 26S subunit non-ATPase 13 (AB009398) | 1.8 | 0.44 |
| MAP kinase kinase 5 (U25265) | 1.3 | 0.44 |
| Cathepsin L (X12451) | 15 | 0.44 |
| IL-1 receptor-associated kinase 1 (L76191) | 1.7 | 0.45 |
| MAP kinase kinase kinase 2 (U07349) | 1.1 | 0.46 |
| peroxisome proliferative activated receptor delta (AL022721) | 2.2 | 0.46 |
| TNF superfamily, member 15 (AF039390) | 16 | 0.46 |
| defender against cell death 1 (D15057) | 3.9 | 0.46 |
| TNF superfamily member 10 (U37518) | 287 | 0.46 |
| cathepsin H (X16832) | 14 | 0.47 |
| protease inhibitor 12 (Z81326) | 0.6 | 0.48 |
| proteasome subunit alpha type, 4 (D00763) | 2.6 | 0.49 |
| proteasome 26S subunit ATPase, 1 (L02426) | 1.8 | 0.49 |
| proteasome 26S subunit ATPase, 2 (D11094) | 2.1 | 0.49 |

TABLE 28-continued

Polynucleotides down-regulated by SEQ ID NO: 6, in primary human macrophages.
The peptide SEQ ID NO: 6 at a concentration of 50 µg/ml was shown to increase the expression of many polynucleotides. Peptide was incubated with the human macrophages for 4 h and the RNA was isolated, converted into labeled cDNA probes and hybridized to Human Operon arrays (PRHU04). The intensity of polynucleotides in unstimulated cells is shown in the second column. The "Ratio of Peptide: Control" columns refer to the intensity of polynucleotide expression in peptide-simulated cells divided by the intensity of unstimulated cells.

| Gene (Accession Number) | Control: Unstimulated cells | Ratio peptide treated: control |
|---|---|---|
| caspase 7 (U67319) | 2.4 | 0.49 |
| matrix metalloproteinase 7 (Z11887) | 2.5 | 0.49 |

TABLE 29

Polynucleotides up-regulated by SEQ ID NO: 1, in HBE cells.
The peptide SEQ ID NO: 1 at a concentration of 50 µg/ml was shown to increase the expression of many polynucleotides. Peptide was incubated with the human HBE epithelial cells for 4 h and the RNA was isolated, converted into labeled cDNA probes and hybridized to Human Operon arrays (PRHU04). The intensity of polynucleotides in unstimulated cells is shown in the second column. The "Ratio Peptide: Control" columns refer to the intensity of polynucleotide expression in peptide-simulated cells divided by the intensity of unstimulated cells.

| Accession Number | Gene | Control: Unstimulated cells | Ratio peptide treated: control |
|---|---|---|---|
| AL110161 | Unknown | 0.22 | 5218.3 |
| AF131842 | Unknown | 0.01 | 573.1 |
| AJ000730 | solute carrier family | 0.01 | 282.0 |
| Z25884 | chloride channel 1 | 0.01 | 256.2 |
| M93426 | protein tyrosine phosphatase receptor-type,zeta | 0.01 | 248.7 |
| X65857 | olfactory receptor, family 1, subfamily D,member 2 | 0.01 | 228.7 |
| M55654 | TATA box binding protein | 0.21 | 81.9 |
| AK001411 | hypothetical protein | 0.19 | 56.1 |
| D29643 | dolichyl-diphosphooligosaccharide-protein glycosyltransferase | 1.56 | 55.4 |
| AF006822 | myelin transcription factor 2 | 0.07 | 55.3 |
| AL117601 | Unknown | 0.05 | 53.8 |
| AL117629 | DKFZP434C245 protein | 0.38 | 45.8 |
| M59465 | tumor necrosis factor,alpha-induced protein 3 | 0.50 | 45.1 |
| AB013456 | aquaporin 8 | 0.06 | 41.3 |
| AJ131244 | SEC24 related gene family, member A | 0.56 | 25.1 |
| AL110179 | Unknown | 0.87 | 24.8 |
| AB037844 | Unknown | 1.47 | 20.6 |
| Z47727 | polymerase II polypeptide K | 0.11 | 20.5 |
| AL035694 | Unknown | 0.81 | 20.4 |
| X68994 | H.sapiens CREB gene | 0.13 | 19.3 |
| AJ238379 | hypothetical protein | 1.39 | 18.5 |
| NM_003519 | H2B histone family member | 0.13 | 18.3 |
| U16126 | glutamate receptor, ionotropic kainate 2 | 0.13 | 17.9 |
| U29926 | adenosine monophosphate deaminase | 0.16 | 16.3 |
| AK001160 | hypothetical protein | 0.39 | 14.4 |
| U18018 | ets variant gene 4 | 0.21 | 12.9 |
| D80006 | KIAA0184 protein | 0.21 | 12.6 |
| AK000768 | hypothetical protein | 0.30 | 12.3 |
| X99894 | insulin promoter factor 1, | 0.26 | 12.0 |
| AL031177 | Unknown | 1.09 | 11.2 |
| AF052091 | unknown | 0.28 | 10.9 |
| L38928 | 5,10-methenyltetrahydrofolate synthetase | 0.22 | 10.6 |
| AL117421 | unknown | 0.89 | 10.1 |

TABLE 29-continued

Polynucleotides up-regulated by SEQ ID NO: 1, in HBE cells.
The peptide SEQ ID NO: 1 at a concentration of 50 µg/ml
was shown to increase the expression of many polynucleotides.
Peptide was incubated with the human HBE epithelial cells
for 4 h and the RNA was isolated, converted into labeled cDNA
probes and hybridized to Human Operon arrays (PRHU04). The intensity of
polynucleotides in unstimulated cells is shown in the second column.
The "Ratio Peptide: Control" columns refer to the intensity of
polynucleotide expression in peptide-simulated
cells divided by the intensity of unstimulated cells.

| Accession Number | Gene | Control: Unstimulated cells | Ratio peptide treated: control |
|---|---|---|---|
| AL133606 | hypothetical protein | 0.89 | 9.8 |
| NM_016227 | membrane protein CH1 | 0.28 | 9.6 |
| NM_006594 | adaptor-related protein complex 4 | 0.39 | 9.3 |
| U54996 | ZW10 homolog, protein | 0.59 | 9.3 |
| AJ007557 | potassium channel, | 0.28 | 9.0 |
| AF043938 | muscle RAS oncogene | 1.24 | 8.8 |
| AK001607 | unknown | 2.74 | 8.7 |
| AL031320 | peroxisomal biogenesis factor 3 | 0.31 | 8.4 |
| D38024 | unknown | 0.31 | 8.3 |
| AF059575 | LIM homeobox TF | 2.08 | 8.2 |
| AF043724 | hepatitis A virus cellular receptor 1 | 0.39 | 8.1 |
| AK002062 | hypothetical protein | 2.03 | 8.0 |
| L13436 | natriuretic peptide receptor | 0.53 | 7.8 |
| U33749 | thyroid transcription factor 1 | 0.36 | 7.6 |
| AF011792 | cell cycle progression 2 protein | 0.31 | 7.6 |
| AK000193 | hypothetical protein | 1.18 | 6.8 |
| AF039022 | exportin, tRNA | 0.35 | 6.8 |
| M17017 | interleukin 8 | 0.50 | 6.7 |
| AF044958 | NADH dehydrogenase | 0.97 | 6.5 |
| U35246 | vacuolar protein sorting | 0.48 | 6.5 |
| AK001326 | tetraspan 3 | 1.59 | 6.5 |
| M55422 | Krueppel-related zinc finger protein | 0.34 | 6.4 |
| U44772 | palmitoyl-protein thioesterase | 1.17 | 6.3 |
| AL117485 | hypothetical protein | 0.67 | 5.9 |
| AB037776 | unknown | 0.75 | 5.7 |
| AF131827 | unknown | 0.69 | 5.6 |
| AL137560 | unknown | 0.48 | 5.2 |
| X05908 | annexin A1 | 0.81 | 5.1 |
| X68264 | melanoma adhesion molecule | 0.64 | 5.0 |
| AL161995 | neurturin | 0.86 | 4.9 |
| AF037372 | cytochrome c oxidase | 0.48 | 4.8 |
| NM_016187 | bridging integrator 2 | 0.65 | 4.8 |
| AL137758 | unknown | 0.57 | 4.8 |
| U59863 | TRAF family member-associated NFKB activator | 0.46 | 4.7 |
| Z30643 | chloride channel Ka | 0.70 | 4.7 |
| D16294 | acetyl-Coenzyme A acyltransferase 2 | 1.07 | 4.6 |
| AJ132592 | zinc finger protein 281 | 0.55 | 4.6 |
| X82324 | POU domain TF | 1.73 | 4.5 |
| NM_016047 | CGI-110 protein | 1.95 | 4.5 |
| AK001371 | hypothetical protein | 0.49 | 4.5 |
| M60746 | H3 histone family member D | 3.05 | 4.5 |
| AB033071 | hypothetical protein | 4.47 | 4.4 |
| AB002305 | KIAA0307 gene product | 1.37 | 4.4 |
| X92689 | UDP-N-acetyl-alpha-D-galactosamine: polypeptide N-acetylgalactosaminyltransferase 3 | 0.99 | 4.4 |
| AL049543 | glutathione peroxidase 5 | 1.62 | 4.3 |
| U43148 | patched homolog | 0.96 | 4.3 |
| M67439 | dopamine receptor D5 | 2.61 | 4.2 |
| U09850 | zinc finger protein 143 | 0.56 | 4.2 |
| L20316 | glucagon receptor | 0.75 | 4.2 |
| AB037767 | a disintegrin-like and metalloprotease | 0.69 | 4.2 |
| NM_017433 | myosin IIIA | 99.20 | 4.2 |
| D26579 | a disintegrin and metalloprotease domain 8 | 0.59 | 4.1 |
| L10333 | reticulon 1 | 1.81 | 4.1 |
| AK000761 | unknown | 1.87 | 4.1 |
| U91540 | NK homeobox family 3, A | 0.80 | 4.1 |
| Z17227 | interleukin 10 receptor, beta | 0.75 | 4.0 |

TABLE 30

Polynucleotides down-regulated by Peptide (50 μg/ml), SEQ ID NO: 1, in HBE cells.
The peptide SEQ ID NO: 1 at a concentration of 50 μg/ml was shown to decrease the expression of many polynucleotides. Peptide was incubated with the human A549 epithelial cells for 4 h and the RNA was isolated, converted into labelled cDNA probes and hybridized to Human Operon arrays (PRHU04). The intensity of polynucleotides in unstimulated cells in shown is the third column. The "Ratio Peptide: Control" columns refer to the intensity of polynucleotide expression in peptide-simulated cells divided by the intensity of unstimulated cells.

| Accession Number | Gene | Control: Unstimulated Cells | Ratio of SEQ ID NO: 1-treated: control |
|---|---|---|---|
| AC004908 | Unknown | 32.4 | 0.09 |
| S70622 | G1 phase-specific gene | 43.1 | 0.10 |
| Z97056 | DEAD/H box polypeptide | 12.8 | 0.11 |
| AK002056 | hypothetical protein | 11.4 | 0.12 |
| L33930 | CD24 antigen | 28.7 | 0.13 |
| X77584 | thioredoxin | 11.7 | 0.13 |
| NM_014106 | PRO1914 protein | 25.0 | 0.14 |
| M37583 | H2A histone family member | 22.2 | 0.14 |
| U89387 | polymerase (RNA) II polypeptide D | 10.2 | 0.14 |
| D25274 | ras-related C3 botulinum toxin substrate 1 | 10.3 | 0.15 |
| J04173 | phosphoglycerate mutase 1 | 11.4 | 0.15 |
| U19765 | zinc finger protein 9 | 8.9 | 0.16 |
| X67951 | proliferation-associated gene A | 14.1 | 0.16 |
| AL096719 | profilin 2 | 20.0 | 0.16 |
| AF165217 | tropomodulin 4 | 14.6 | 0.16 |
| NM_014341 | mitochondrial carrier homolog 1 | 11.1 | 0.16 |
| AL022068 | Unknown | 73.6 | 0.17 |
| X69150 | ribosomal protein S18 | 42.8 | 0.17 |
| AL031577 | Unknown | 35.0 | 0.17 |
| AL031281 | Unknown | 8.9 | 0.17 |
| AF090094 | Human mRNA for ornithine decarboxylase antizyme, | 10.3 | 0.17 |
| AL022723 | HLA-G histocompatibility antigen, class I, G | 20.6 | 0.18 |
| U09813 | ATP synthase, H+ transporting mitochondrial F0 complex | 9.8 | 0.18 |
| AF000560 | Homo sapiens TTF-I interacting peptide 20 | 20.2 | 0.19 |
| NM_016094 | HSPC042 protein | 67.2 | 0.19 |
| AF047183 | NADH dehydrogenase | 7.5 | 0.19 |
| D14662 | anti-oxidant protein 2 (non-selenium glutathione peroxidase, acidic calcium-independent phospholipas | 8.1 | 0.19 |
| X16662 | annexin A8 | 8.5 | 0.19 |
| U14588 | paxillin | 11.3 | 0.19 |
| AL117654 | DKFZP586D0624 protein | 12.6 | 0.20 |
| AK001962 | hypothetical protein | 7.7 | 0.20 |
| L41559 | 6-pyruvoyl-tetrahydropterin synthase/dimerization cofactor of hepatocyte nuclear factor 1 alpha | 9.1 | 0.20 |
| NM_016139 | 16.7 Kd protein | 21.0 | 0.21 |
| NM_016080 | CGI-150 protein | 10.7 | 0.21 |
| U86782 | 26S proteasome-associated pad1 homolog | 6.7 | 0.21 |
| AJ400717 | tumor protein, translationally-controlled 1 | 9.8 | 0.21 |
| X07495 | homeo box C4 | 31.0 | 0.21 |
| AL034410 | Unknown | 7.3 | 0.22 |
| X14787 | thrombospondin 1 | 26.2 | 0.22 |
| AF081192 | purine-rich element binding protein B | 6.8 | 0.22 |
| D49489 | protein disulfide isomerase-related protein | 11.0 | 0.22 |
| NM_014051 | PTD011 protein | 9.3 | 0.22 |
| AK001536 | Unknown | 98.0 | 0.22 |
| X62534 | high-mobility group protein 2 | 9.5 | 0.22 |
| AJ005259 | endothelial differentiation-related factor 1 | 6.7 | 0.22 |
| NM_000120 | epoxide hydrolase 1, microsomal | 10.0 | 0.22 |
| M38591 | S100 calcium-binding protein A10 | 23.9 | 0.23 |
| AF071596 | immediate early response 3 | 11.5 | 0.23 |
| X16396 | methylene tetrahydrofolate dehydrogenase | 8.3 | 0.23 |
| AK000934 | ATPase inhibitor precursor | 7.6 | 0.23 |
| AL117612 | Unknown | 10.7 | 0.23 |
| AF119043 | transcriptional intermediary factor 1 gamma | 7.3 | 0.23 |
| AF037066 | solute carrier family 22 member 1-like antisense | 7.6 | 0.23 |

TABLE 30-continued

Polynucleotides down-regulated by Peptide (50 μg/ml), SEQ ID NO: 1, in HBE cells.
The peptide SEQ ID NO: 1 at a concentration of 50 μg/ml was shown to decrease the expression of many polynucleotides. Peptide was incubated with the human A549 epithelial cells for 4 h and the RNA was isolated, converted into labelled cDNA probes and hybridized to Human Operon arrays (PRHU04). The intensity of polynucleotides in unstimulated cells in shown is the third column. The "Ratio Peptide: Control" columns refer to the intensity of polynucleotide expression in peptide-simulated cells divided by the intensity of unstimulated cells.

| Accession Number | Gene | Control: Unstimulated Cells | Ratio of SEQ ID NO: 1- treated: control |
|---|---|---|---|
| AF134406 | cytochrome c oxidase subunit | 13.3 | 0.23 |
| AE000661 | Unknown | 9.2 | 0.24 |
| AL157424 | synaptojanin 2 | 7.2 | 0.24 |
| X56468 | tyrosine 3-monooxygenase/tryptophan 5-monooxygenase activation protein, | 7.2 | 0.24 |
| U39318 | ubiquitin-conjugating enzyme E2D 3 | 10.7 | 0.24 |
| AL034348 | Unknown | 24.4 | 0.24 |
| D26600 | proteasome subunit beta type 4 | 11.4 | 0.24 |
| AB032987 | Unknown | 16.7 | 0.24 |
| J04182 | lysosomal-associated membrane protein 1 | 7.4 | 0.24 |
| X78925 | zinc finger protein 267 | 16.1 | 0.25 |
| NM_000805 | gastrin | 38.1 | 0.25 |
| U29700 | anti-Mullerian hormone receptor, type II | 12.0 | 0.25 |
| Z98200 | Unknown | 13.4 | 0.25 |
| U07857 | signal recognition particle | 10.3 | 0.25 |
| L05096 | *Homo sapiens* ribosomal protein L39 | 25.3 | 0.25 |
| AK001443 | hypothetical protein | 7.5 | 0.25 |
| K03515 | glucose phosphate isomerase | 6.2 | 0.25 |
| X57352 | interferon induced transmembrane protein 3 | 7.5 | 0.26 |
| J02883 | colipase pancreatic | 5.7 | 0.26 |
| M24069 | cold shock domain protein | 6.3 | 0.26 |
| AJ269537 | chondroitin-4-sulfotransferase | 60.5 | 0.26 |
| AL137555 | Unknown | 8.5 | 0.26 |
| U89505 | RNA binding motif protein 4 | 5.5 | 0.26 |
| U82938 | CD27-binding protein | 7.5 | 0.26 |
| X99584 | SMT3 homolog 1 | 12.8 | 0.26 |
| AK000847 | Unknown | 35.8 | 0.27 |
| NM_014463 | Lsm3 protein | 7.8 | 0.27 |
| AL133645 | Unknown | 50.8 | 0.27 |
| X78924 | zinc finger protein 266 | 13.6 | 0.27 |
| NM_004304 | anaplastic lymphoma kinase | 15.0 | 0.27 |
| X57958 | ribosomal protein L7 | 27.9 | 0.27 |
| U63542 | Unknown | 12.3 | 0.27 |
| AK000086 | hypothetical protein | 8.3 | 0.27 |
| X57138 | H2A histone family member N | 32.0 | 0.27 |
| AB023206 | KIAA0989 protein | 6.5 | 0.27 |
| AB021641 | gonadotropin inducible transcriptn repressor-1, | 5.5 | 0.28 |
| AF050639 | NADH dehydrogenase | 5.5 | 0.28 |
| M62505 | complement component 5 receptor 1 | 7.5 | 0.28 |
| X64364 | basigin | 5.8 | 0.28 |
| AJ224082 | Unknown | 22.5 | 0.28 |
| AF042165 | cytochrome c oxidase | 20.4 | 0.28 |
| AK001472 | anillin | 10.9 | 0.28 |
| X86428 | protein phosphatase 2A subunit | 12.7 | 0.28 |
| AF227132 | candidate taste receptor T2R5 | 5.1 | 0.28 |
| Z98751 | Unknown | 5.3 | 0.28 |
| D21260 | clathrin heavy polypeptide | 8.3 | 0.28 |
| AF041474 | actin-like 6 | 15.1 | 0.28 |
| NM_005258 | GTP cyclohydrolase I protein | 7.6 | 0.28 |
| L20859 | solute carrier family 20 | 9.6 | 0.29 |
| Z80783 | H2B histone family member | 9.0 | 0.29 |
| AB011105 | laminin alpha 5 | 7.1 | 0.29 |
| AL008726 | protective protein for beta-galactosidase | 5.2 | 0.29 |
| D29012 | proteasome subunit | 12.6 | 0.29 |
| X63629 | cadherin 3 P-cadherin | 6.8 | 0.29 |
| X02419 | plasminogen activator urokinase | 12.9 | 0.29 |
| X13238 | cytochrome c oxidase | 8.0 | 0.29 |
| X59798 | cyclin D1 | 12.7 | 0.30 |
| D78151 | proteasome 26S subunit | 7.6 | 0.31* |
| AF054185 | proteasome subunit | 18.8 | 0.31 |
| J03890 | surfactant pulmonary-associated protein C | 5.5 | 0.32 |
| M34079 | proteasome 26S subunit, | 5.2 | 0.33 |

TABLE 31

Up-regulation of Polynucleotide expression in A549 cells induced by Formula A Peptides.
The peptides at a concentration of 50 μg/ml were shown to increase the expression of many polynucleotides. Peptide was incubated with the human A549 epithelial cells for 4 h and the RNA was isolated, converted into labeled cDNA probes and hybridized to Human Operon arrays (PRHU04). The intensity of polynucleotides in control, unstimulated cells are shown in the second and third columns for labeling of cDNA with the dyes Cy3 and Cy5 respectively. The "ID#: Control" columns refer to the intensity of polynucleotide expression in peptide-simulated cells divided by the intensity of unstimulated cells.

| Accession Number | Gene | control-Cy3 | control-Cy5 | ID 5: control | ID 6: control | ID 7: control | ID 8: control | ID 9: control | ID 10: control |
|---|---|---|---|---|---|---|---|---|---|
| U12472 | glutathione S-transferase | 0.09 | 0.31 | 13.0 | 3.5 | 4.5 | 7.0 | 4.3 | 16.4 |
| X66403 | cholinergic receptor | 0.17 | 0.19 | 7.8 | 9.9 | 6.0 | 6.4 | 5.0 | 15.7 |
| AK001932 | unknown | 0.11 | 0.25 | 19.4 | 4.6 | 9.9 | 7.6 | 8.1 | 14.5 |
| X58079 | S100 calcium-binding protein | 0.14 | 0.24 | 12.2 | 7.6 | 8.1 | 4.3 | 4.5 | 13.2 |
| U18244 | solute carrier family 1 | 0.19 | 0.20 | 6.1 | 9.7 | 11.9 | 5.0 | 3.7 | 10.6 |
| U20648 | zinc finger protein | 0.16 | 0.13 | 5.3 | 6.2 | 5.6 | 3.1 | 6.8 | 9.5 |
| AB037832 | unknown | 0.10 | 0.29 | 9.0 | 4.2 | 9.4 | 3.1 | 2.6 | 8.7 |
| AC002542 | unknown | 0.15 | 0.07 | 10.5 | 15.7 | 7.8 | 10.1 | 11.7 | 8.2 |
| M89796 | membrane-spanning 4-domains, subfamily A | 0.15 | 0.14 | 2.6 | 6.1 | 7.6 | 3.5 | 13.3 | 8.1 |
| AF042163 | cytochrome c oxidase | 0.09 | 0.19 | 3.9 | 3.2 | 7.6 | 6.3 | 4.9 | 7.9 |
| AL032821 | Vanin 2 | 0.41 | 0.23 | 2.5 | 5.2 | 3.2 | 2.1 | 4.0 | 7.9 |
| U25341 | melatonin receptor 1B | 0.04 | 0.24 | 33.1 | 5.1 | 23.3 | 6.6 | 4.1 | 7.6 |
| U52219 | G protein-coupled receptor | 0.28 | 0.20 | 2.1 | 6.2 | 6.9 | 2.4 | 3.9 | 7.1 |
| X04506 | apolipoprotein B | 0.29 | 0.32 | 7.9 | 3.4 | 3.3 | 4.8 | 2.6 | 7.0 |
| AB011138 | ATPase type IV | 0.12 | 0.07 | 3.5 | 12.9 | 6.6 | 6.4 | 21.3 | 6.9 |
| AF055018 | unknown | 0.28 | 0.22 | 3.8 | 6.9 | 5.0 | 2.3 | 3.1 | 6.8 |
| AK002037 | hypothetical protein | 0.08 | 0.08 | 2.9 | 7.9 | 14.1 | 7.9 | 20.1 | 6.5 |
| AK001024 | guanine nucleotide-binding protein | 0.16 | 0.11 | 7.7 | 11.9 | 5.0 | 10.3 | 6.0 | 6.3 |
| AF240467 | TLR-7 | 0.11 | 0.10 | 20.4 | 9.0 | 3.4 | 9.4 | 12.9 | 6.1 |
| AF105367 | glucagon-like peptide 2 receptor | 0.15 | 0.35 | 23.2 | 2.6 | 3.0 | 10.6 | 2.9 | 5.7 |
| AL009183 | TNFR superfamily, member 9 | 0.46 | 0.19 | 10.6 | 4.7 | 3.7 | 2.8 | 6.5 | 5.7 |
| X54380 | pregnancy-zone protein | 0.23 | 0.08 | 4.7 | 11.9 | 7.2 | 12.7 | 3.8 | 5.5 |
| AL137736 | unknown | 0.22 | 0.15 | 2.1 | 7.2 | 3.3 | 7.1 | 4.6 | 5.5 |
| X05615 | thyroglobulin | 0.28 | 0.42 | 6.3 | 2.7 | 7.7 | 2.4 | 3.1 | 5.4 |
| D28114 | myelin-associated protein | 0.24 | 0.08 | 2.5 | 15.9 | 13.0 | 7.1 | 13.7 | 5.4 |
| AK000358 | microfibrillar-associated protein 3 | 0.28 | 0.28 | 8.7 | 4.2 | 7.2 | 3.2 | 2.4 | 5.3 |
| AK001351 | unknown | 0.12 | 0.22 | 3.9 | 7.6 | 8.7 | 3.9 | 2.3 | 5.2 |
| U79289 | unknown | 0.14 | 0.27 | 2.5 | 2.7 | 2.8 | 2.0 | 4.3 | 5.1 |
| AB014546 | ring finger protein | 0.12 | 0.34 | 6.8 | 2.4 | 4.1 | 2.7 | 2.0 | 5.0 |
| AL117428 | DKFZP434A236 protein | 0.10 | 0.07 | 2.8 | 16.1 | 12.8 | 9.7 | 14.2 | 4.9 |
| AL050378 | unknown | 0.41 | 0.14 | 3.5 | 8.7 | 11.7 | 3.5 | 7.0 | 4.9 |
| AJ250562 | transmembrane 4 superfamily member 2 | 0.13 | 0.10 | 5.2 | 5.7 | 14.2 | 3.8 | 10.3 | 4.8 |
| NM_001756 | corticosteroid binding globulin | 0.28 | 0.13 | 4.0 | 7.9 | 6.5 | 14.9 | 5.6 | 4.8 |
| AL137471 | hypothetical protein | 0.29 | 0.05 | 3.7 | 18.0 | 6.2 | 7.2 | 16.3 | 4.7 |
| M19684 | protease inhibitor 1 | 0.41 | 0.14 | 3.5 | 4.6 | 5.4 | 2.8 | 9.4 | 4.7 |

TABLE 31-continued

Up-regulation of Polynucleotide expression in A549 cells induced by Formula A Peptides.

The peptides at a concentration of 50 μg/ml were shown to increase the expression of many polynucleotides. Peptide was incubated with the human A549 epithelial cells for 4 h and the RNA was isolated, converted into labeled cDNA probes and hybridized to Human Operon arrays (PRHU04). The intensity of polynucleotides in control, unstimulated cells are shown in the second and third columns for labeling of cDNA with the dyes Cy3 and Cy5 respectively. The "ID#: Control" columns refer to the intensity of polynucleotide expression in peptide-simulated cells divided by the intensity of unstimulated cells.

| Accession Number | Gene | control-Cy3 | control-Cy5 | ID 5: control | ID 6: control | ID 7: control | ID 8: control | ID 9: control | ID 10: control |
|---|---|---|---|---|---|---|---|---|---|
| NM_001963 | epidermal growth factor | 0.57 | 0.05 | 3.4 | 6.2 | 1.8 | 32.9 | 14.7 | 4.4 |
| NM_000910 | neuropeptide Y receptor | 0.62 | 0.36 | 3.1 | 2.7 | 2.3 | 2.6 | 3.1 | 4.4 |
| AF022212 | Rho GTPase activating protein 6 | 0.19 | 0.02 | 9.0 | 45.7 | 25.6 | 12.4 | 72.2 | 4.4 |
| AK001674 | cofactor required for Sp1 | 0.11 | 0.13 | 8.4 | 6.5 | 7.9 | 4.5 | 7.4 | 4.3 |
| U51920 | signal recognition particle | 0.23 | 0.27 | 3.4 | 3.8 | 2.1 | 4.1 | 8.8 | 4.2 |
| AK000576 | hypothetical protein | 0.27 | 0.06 | 4.4 | 14.7 | 7.4 | 14.1 | 8.6 | 4.2 |
| AL080073 | unknown | 0.17 | 0.20 | 21.6 | 3.9 | 4.3 | 8.8 | 2.6 | 4.1 |
| U59628 | paired box gene 9 | 0.34 | 0.06 | 3.4 | 14.1 | 5.4 | 7.9 | 4.9 | 4.1 |
| U90548 | butyrophilin, subfamily 3, member A3 | 0.41 | 0.31 | 2.3 | 4.7 | 5.5 | 6.8 | 3.4 | 4.1 |
| M19673 | cystatin SA | 0.43 | 0.26 | 2.3 | 8.5 | 4.5 | 2.5 | 4.1 | 3.8 |
| AL161972 | ICAM 2 | 0.44 | 0.37 | 2.0 | 3.6 | 2.0 | 2.7 | 5.5 | 3.8 |
| X54938 | inositol 1,4,5-trisphosphate 3-kinase A | 0.32 | 0.22 | 3.9 | 3.3 | 6.2 | 3.1 | 4.4 | 3.7 |
| AB014575 | KIAA0675 gene product | 0.04 | 0.13 | 46.2 | 4.5 | 10.2 | 8.0 | 6.2 | 3.4 |
| M83664 | MHC II, DP beta 1 | 0.57 | 0.29 | 2.9 | 2.1 | 2.0 | 3.1 | 6.6 | 3.4 |
| AK000043 | hypothetical protein | 0.34 | 0.14 | 2.7 | 7.1 | 3.7 | 9.4 | 8.8 | 3.3 |
| U60666 | testis specific leucine rich repeat protein | 0.21 | 0.11 | 9.9 | 9.0 | 4.1 | 5.5 | 13.0 | 3.3 |
| AK000337 | hypothetical protein | 0.49 | 0.19 | 4.3 | 5.1 | 4.7 | 10.6 | 7.1 | 3.3 |
| AF050198 | putative mitochondrial space protein | 0.34 | 0.15 | 7.0 | 6.3 | 3.6 | 5.6 | 11.9 | 3.3 |
| AJ251029 | odorant-binding protein 2A | 0.28 | 0.12 | 4.4 | 9.4 | 7.2 | 8.8 | 7.1 | 3.2 |
| X74142 | forkhead box G1B | 0.12 | 0.33 | 19.5 | 4.5 | 8.4 | 6.4 | 4.4 | 3.2 |
| AB029033 | KIAA1110 protein | 0.35 | 0.24 | 3.1 | 2.2 | 5.6 | 5.2 | 3.1 | 3.1 |
| D85606 | cholecystokinin A receptor | 0.51 | 0.14 | 4.3 | 3.9 | 4.6 | 3.5 | 7.2 | 3.1 |
| X84195 | acylphosphatase 2 muscle type | 0.32 | 0.19 | 4.8 | 3.7 | 5.0 | 11.2 | 9.8 | 3.0 |
| U57971 | ATPase Ca++ transporting plasma membrane 3 | 0.29 | 0.13 | 2.2 | 7.9 | 1.8 | 6.3 | 4.8 | 3.0 |
| J02611 | apolipoprotein D | 0.28 | 0.10 | 2.8 | 11.0 | 3.7 | 10.3 | 8.4 | 3.0 |
| AF071510 | lecithin retinol acyltransferase | 0.07 | 0.05 | 7.9 | 3.8 | 11.7 | 46.0 | 16.3 | 3.0 |
| AF131757 | unknown | 0.10 | 0.08 | 4.8 | 9.0 | 44.3 | 9.3 | 10.7 | 3.0 |
| L10717 | IL2-inducible T-cell kinase | 0.45 | 0.21 | 2.5 | 4.9 | 2.8 | 10.9 | 4.5 | 2.9 |
| L32961 | 4-aminobutyrate aminotransferase | 0.64 | 0.32 | 3.6 | 2.9 | 3.2 | 5.3 | 2.3 | 2.9 |
| NM_003631 | poly (ADP-ribose) glycohydrolase | 0.46 | 0.41 | 9.7 | 3.9 | 4.1 | 3.8 | 2.8 | 2.7 |
| AF098484 | pronapsin A | 0.28 | 0.14 | 3.7 | 3.7 | 5.6 | 11.6 | 3.7 | 2.5 |
| NM_009589 | arylsulfatase D | 0.73 | 0.16 | 3.2 | 5.6 | 6.0 | 48.6 | 7.2 | 2.4 |

TABLE 31-continued

Up-regulation of Polynucleotide expression in A549 cells induced by Formula A Peptides.

The peptides at a concentration of 50 μg/ml were shown to increase the expression of many polynucleotides. Peptide was incubated with the human A549 epithelial cells for 4 h and the RNA was isolated, converted into labeled cDNA probes and hybridized to Human Operon arrays (PRHU04). The intensity of polynucleotides in control, unstimulated cells are shown in the second and third columns for labeling of cDNA with the dyes Cy3 and Cy5 respectively. The "ID#: Control" columns refer to the intensity of polynucleotide expression in peptide-simulated cells divided by the intensity of unstimulated cells.

| Accession Number | Gene | control-Cy3 | control-Cy5 | ID 5: control | ID 6: control | ID 7: control | ID 8: control | ID 9: control | ID 10: control |
|---|---|---|---|---|---|---|---|---|---|
| M14764 | TNFR superfamily, member 16 | 0.49 | 0.15 | 2.3 | 3.5 | 10.6 | 13.6 | 6.8 | 2.2 |
| AL035250 | endothelin 3 | 0.52 | 0.14 | 2.1 | 7.3 | 4.8 | 4.5 | 3.7 | 2.2 |
| M97925 | defensin, alpha 5, Paneth cell-specific | 0.33 | 0.07 | 4.0 | 14.7 | 7.8 | 9.4 | 3.5 | 2.1 |
| D43945 | transcription factor EC | 0.46 | 0.19 | 6.6 | 2.9 | 8.2 | 4.0 | 3.5 | 2.1 |
| D16583 | histidine decarboxylase | 0.46 | 0.09 | 3.2 | 13.8 | 4.2 | 8.8 | 13.7 | 2.1 |

TABLE 32

Up-regulation of Polynucleotide expression in A549 cells induced by Formula B Peptides.

The peptides at a concentration of 50 μg/ml were shown to increase the expression of many polynucleotides. Peptide was incubated with the human A549 epithelial cells for 4 h and the RNA was isolated, converted into labeled cDNA probes and hybridized to Human Operon arrays (PRHU04). The intensity of polynucleotides in control, unstimulated cells are shown in the second and third columns for labeling of cDNA with the dyes Cy3 and Cy5 respectively. The "ID#: Control" columns refer to the intensity of polynucleotide expression in peptide-simulated cells divided by the intensity of unstimulated cells.

| Accession Number | Gene | control-Cy3 | control-Cy5 | ID 12: control | ID 13: control | ID 14: control | ID 15: control | ID 16: control | ID 17: control |
|---|---|---|---|---|---|---|---|---|---|
| AL157466 | unknown | 0.05 | 0.06 | 18.0 | 21.4 | 16.7 | 5.2 | 6.8 | 8.6 |
| AB023215 | KIAA0998 protein | 0.19 | 0.07 | 14.8 | 10.6 | 7.9 | 14.4 | 6.6 | 16.1 |
| AL031121 | unknown | 0.24 | 0.09 | 14.1 | 5.7 | 3.8 | 5.5 | 2.8 | 4.6 |
| NM_016331 | zinc finger protein | 0.16 | 0.08 | 12.8 | 7.2 | 11.0 | 5.3 | 11.2 | 9.7 |
| M14565 | cytochrome P450 | 0.16 | 0.12 | 10.6 | 12.5 | 5.0 | 3.6 | 10.1 | 6.3 |
| U22492 | G protein-coupled receptor 8 | 0.28 | 0.07 | 10.4 | 8.9 | 4.8 | 10.8 | 6.6 | 3.6 |
| U76010 | solute carrier family 30 | 0.14 | 0.07 | 9.7 | 18.6 | 3.7 | 4.8 | 5.6 | 8.9 |
| AK000685 | unknown | 0.51 | 0.10 | 9.0 | 3.1 | 2.8 | 3.9 | 15.3 | 3.0 |
| AF013620 | Immunoglobulin heavy variable 4-4 | 0.19 | 0.18 | 8.5 | 2.6 | 6.2 | 5.7 | 8.2 | 3.8 |
| AL049296 | unknown | 0.61 | 0.89 | 8.1 | 3.2 | 2.7 | 3.2 | 2.7 | 2.0 |
| AB006622 | KIAA0284 protein | 0.47 | 0.28 | 7.5 | 5.0 | 2.8 | 11.1 | 5.5 | 4.6 |
| X04391 | CD5 antigen | 0.22 | 0.13 | 7.2 | 16.7 | 2.7 | 7.7 | 6.1 | 5.9 |
| AK000067 | hypothetical protein | 0.80 | 0.35 | 7.1 | 4.6 | 2.1 | 3.2 | 8.5 | 2.2 |
| AF053712 | TNF superfamily_ member 11 | 0.17 | 0.08 | 6.9 | 17.7 | 3.0 | 6.2 | 12.3 | 5.2 |
| X58079 | S100 calcium-binding protein A1 | 0.14 | 0.24 | 6.7 | 6.7 | 5.9 | 6.5 | 5.3 | 2.5 |
| M91036 | hemoglobin_ gamma A | 0.48 | 0.36 | 6.7 | 14.2 | 2.1 | 2.9 | 2.7 | 4.8 |
| AF055018 | unknown | 0.28 | 0.22 | 6.3 | 10.7 | 2.7 | 2.6 | 4.6 | 6.5 |
| L17325 | pre-T/NK cell associated protein | 0.19 | 0.29 | 6.1 | 4.4 | 6.5 | 4.7 | 4.0 | 4.0 |
| D45399 | phosphodiesterase | 0.21 | 0.18 | 6.1 | 4.6 | 5.0 | 2.8 | 10.8 | 4.0 |
| AB023188 | KIAA0971 protein | 0.29 | 0.13 | 5.9 | 10.6 | 3.6 | 3.4 | 10.6 | 7.2 |
| NM_012177 | F-box protein | 0.26 | 0.31 | 5.9 | 5.5 | 3.8 | 2.8 | 3.0 | 6.8 |
| D38550 | E2F TF 3 | 0.43 | 0.39 | 5.8 | 3.4 | 2.1 | 4.5 | 2.5 | 2.4 |
| AL050219 | unknown | 0.26 | 0.04 | 5.7 | 17.0 | 3.1 | 9.2 | 30.3 | 16.1 |
| AL137540 | unknown | 0.67 | 0.79 | 5.5 | 3.2 | 3.9 | 10.9 | 2.9 | 2.3 |
| D50926 | KIAA0136 protein | 0.57 | 0.21 | 5.4 | 5.6 | 2.0 | 3.3 | 4.4 | 3.2 |
| AL137658 | unknown | 0.31 | 0.07 | 5.4 | 12.1 | 2.6 | 10.8 | 3.9 | 8.6 |

TABLE 32-continued

Up-regulation of Polynucleotide expression in A549 cells induced by
Formula B Peptides.
The peptides at a concentration of 50 μg/ml were shown to increase the
expression of many polynucleotides. Peptide was incubated with the human A549
epithelial cells for 4 h and the RNA was isolated, converted into labeled cDNA probes
and hybridized to Human Operon arrays (PRHU04). The intensity of polynucleotides in
control, unstimulated cells are shown in the second and third columns for labeling of
cDNA with the dyes Cy3 and Cy5 respectively. The "ID#: Control" columns refer to the
intensity of polynucleotide expression in peptide-simulated cells divided by the intensity
of unstimulated cells.

| Accession Number | Gene | control-Cy3 | control-Cy5 | ID 12: control | ID 13: control | ID 14: control | ID 15: control | ID 16: control | ID 17: control |
|---|---|---|---|---|---|---|---|---|---|
| U21931 | fructose-bisphosphatase 1 | 0.48 | 0.14 | 5.4 | 4.1 | 2.9 | 3.6 | 6.0 | 3.2 |
| AK001230 | DKFZP586D211 protein | 0.43 | 0.26 | 5.0 | 4.6 | 2.1 | 2.2 | 2.5 | 2.7 |
| AL137728 | unknown | 0.67 | 0.47 | 5.0 | 5.9 | 2.2 | 6.8 | 5.9 | 2.1 |
| AB022847 | unknown | 0.39 | 0.24 | 4.5 | 2.2 | 3.5 | 4.3 | 3.8 | 3.7 |
| X75311 | mevalonate kinase | 0.67 | 0.22 | 4.3 | 4.0 | 2.0 | 8.3 | 4.0 | 5.1 |
| AK000946 | DKFZP566C243 protein | 0.36 | 0.29 | 4.1 | 3.8 | 3.9 | 5.4 | 25.8 | 2.7 |
| AB023197 | KIAA0980 protein | 0.25 | 0.30 | 4.0 | 8.3 | 2.1 | 8.8 | 2.2 | 4.9 |
| AB014615 | fibroblast growth factor 8 | 0.19 | 0.07 | 3.9 | 3.3 | 7.0 | 3.4 | 2.2 | 7.7 |
| X04014 | unknown | 0.29 | 0.16 | 3.8 | 2.5 | 2.2 | 3.0 | 5.5 | 3.1 |
| U76368 | solute carrier family 7 | 0.46 | 0.17 | 3.8 | 3.8 | 2.8 | 3.2 | 4.2 | 3.0 |
| AB032436 | unknown | 0.14 | 0.21 | 3.8 | 2.7 | 6.1 | 3.2 | 4.5 | 2.6 |
| AB020683 | KIAA0876 protein | 0.37 | 0.21 | 3.7 | 4.2 | 2.2 | 5.3 | 2.9 | 9.4 |
| NM_012126 | carbohydrate sulfotransferase 5 | 0.31 | 0.20 | 3.7 | 5.2 | 3.2 | 3.4 | 3.9 | 2.5 |
| AK002037 | hypothetical protein | 0.08 | 0.08 | 3.7 | 17.1 | 4.6 | 12.3 | 11.0 | 8.7 |
| X78712 | glycerol kinase pseudogene 2 | 0.17 | 0.19 | 3.6 | 2.5 | 4.5 | 5.3 | 2.2 | 3.3 |
| NM_014178 | HSPC156 protein | 0.23 | 0.12 | 3.5 | 8.4 | 2.9 | 6.9 | 14.4 | 5.5 |
| AC004079 | homeo box A2 | 0.31 | 0.11 | 3.5 | 7.0 | 2.1 | 2.0 | 7.3 | 9.1 |
| AL080182 | unknown | 0.51 | 0.21 | 3.4 | 3.5 | 2.2 | 2.1 | 2.9 | 2.4 |
| M91036 | hemoglobin gamma G | 0.22 | 0.02 | 3.4 | 26.3 | 5.8 | 6.8 | 30.4 | 21.6 |
| AJ000512 | serum/glucocorticoid regulated kinase | 0.27 | 0.43 | 3.3 | 2.1 | 4.9 | 2.3 | 3.9 | 2.7 |
| AK002140 | hypothetical protein | 0.28 | 0.14 | 3.3 | 9.9 | 2.8 | 2.1 | 16.6 | 7.2 |
| AL137284 | unknown | 0.22 | 0.04 | 3.3 | 7.2 | 4.1 | 6.0 | 12.2 | 3.7 |
| Z11898 | POU domain_class 5 TF 1 | 0.12 | 0.29 | 3.2 | 3.7 | 8.2 | 2.5 | 6.6 | 2.2 |
| AB017016 | brain-specific protein | 0.27 | 0.29 | 3.1 | 2.8 | 2.5 | 2.8 | 3.3 | 5.5 |
| X54673 | Solute-carrier family 6 | 0.34 | 0.08 | 2.9 | 12.0 | 2.2 | 10.4 | 7.4 | 5.9 |
| AL033377 | unknown | 0.40 | 0.22 | 2.6 | 2.6 | 2.6 | 2.3 | 4.5 | 2.2 |
| X85740 | CCR4 | 0.34 | 0.05 | 2.6 | 2.3 | 2.6 | 2.5 | 12.5 | 5.2 |
| AB010419 | core-binding factor | 0.59 | 0.20 | 2.5 | 12.8 | 2.0 | 2.8 | 2.9 | 5.9 |
| AL109726 | uknown | 0.14 | 0.15 | 2.3 | 9.0 | 4.3 | 4.4 | 2.6 | 3.7 |
| NM_012450 | sulfate transporter 1 | 0.15 | 0.10 | 2.2 | 3.1 | 8.2 | 9.9 | 4.7 | 5.9 |
| J04599 | biglycan | 0.39 | 0.30 | 2.1 | 3.3 | 6.6 | 2.2 | 2.7 | 5.4 |
| AK000266 | hypothetical protein | 0.49 | 0.35 | 2.1 | 3.5 | 3.5 | 6.6 | 4.3 | 4.0 |

TABLE 33

Up-regulation of Polynucleotide expression in A549 cells induced by Formula C Peptides.

The peptides at a concentration of 50 µg/ml were shown to increase the expression of many polynucleotides. Peptide was incubated with the human A549 epithelial cells for 4 h and the RNA was isolated, converted into labeled cDNA probes and hybridized to Human Operon arrays (PRHU04). The intensity of polynucleotides in control, unstimulated cells are shown in the second and third columns for labeling of cDNA with the dyes Cy3 and Cy5 respectively. The "ID#: Control" columns refer to the intensity of polynucleotide expression in peptide-simulated cells divided by the intensity of unstimulated cells.

| Accession Number | Gene | control-Cy3 | control-Cy5 | ID 19: control | ID 20: control | ID 21: control | ID 22: control | ID 23: control | ID 24: control |
|---|---|---|---|---|---|---|---|---|---|
| NM_014139 | sodium channel voltage-gated, | 0.04 | 0.05 | 31.6 | 25.2 | 18.0 | 9.7 | 22.2 | 11.2 |
| X84003 | TATA box binding protein | 0.47 | 0.07 | 31.8 | 12.7 | 2.5 | 2.8 | 18.0 | 14.2 |
| AF144412 | lens epithelial cell protein | 0.25 | 0.07 | 23.9 | 8.0 | 6.8 | 3.4 | 16.2 | 3.5 |
| AL080107 | unknown | 0.11 | 0.06 | 17.8 | 34.4 | 12.4 | 6.2 | 5.4 | 7.9 |
| AF052116 | unknown | 0.34 | 0.07 | 15.5 | 3.9 | 9.2 | 3.0 | 6.9 | 2.7 |
| AB033063 | unknown | 0.46 | 0.13 | 15.2 | 10.3 | 4.0 | 2.6 | 7.2 | 11.2 |
| AK000258 | hypothetical protein | 0.27 | 0.07 | 13.9 | 8.0 | 3.5 | 3.4 | 26.5 | 11.5 |
| NM_006963 | zinc finger protein | 0.10 | 0.08 | 12.8 | 6.8 | 6.2 | 5.9 | 17.2 | 1241.2 |
| NM_014099 | PRO1768 protein | 0.30 | 0.06 | 12.3 | 17.4 | 5.4 | 5.4 | 19.5 | 3.4 |
| AK000996 | hypothetical protein | 0.17 | 0.07 | 10.0 | 8.0 | 9.7 | 7.4 | 20.7 | 16.3 |
| M81933 | cell division cycle 25A | 0.13 | 0.21 | 8.8 | 7.8 | 19.6 | 15.6 | 4.8 | 3.8 |
| AF181286 | unknown | 0.05 | 0.22 | 8.8 | 2.7 | 12.0 | 35.6 | 5.9 | 2.3 |
| AJ272208 | IL-1R accessory protein-like 2 | 0.22 | 0.17 | 8.8 | 2.9 | 5.0 | 3.2 | 9.8 | 7.3 |
| AF030555 | fatty-acid-Coenzyme A ligase | 0.10 | 0.39 | 8.7 | 2.2 | 11.3 | 9.9 | 3.0 | 2.1 |
| AL050125 | unknown | 0.23 | 0.07 | 8.6 | 14.3 | 5.2 | 2.8 | 18.7 | 8.3 |
| AB011096 | KIAA0524 protein | 0.21 | 0.08 | 8.5 | 24.4 | 4.7 | 6.8 | 10.4 | 7.5 |
| J03068 | N-acylaminoacyl-peptide hydrolase | 0.54 | 0.21 | 8.3 | 2.4 | 2.2 | 4.1 | 3.0 | 6.0 |
| M33906 | MHC class II, DQ alpha 1 | 0.14 | 0.08 | 7.6 | 4.5 | 15.2 | 6.1 | 7.5 | 7.9 |
| AJ272265 | secreted phosphoprotein | 0.21 | 0.09 | 7.6 | 9.0 | 3.3 | 4.9 | 18.8 | 14.5 |
| J00210 | interferon alpha 13 | 0.41 | 0.07 | 7.2 | 15.0 | 2.8 | 3.1 | 11.0 | 4.3 |
| AK001952 | hypothetical protein | 0.42 | 0.21 | 6.9 | 4.9 | 2.5 | 3.1 | 7.6 | 4.5 |
| X54131 | protein tyrosine phosphatase, receptor type, | 0.09 | 0.20 | 6.4 | 6.5 | 7.7 | 15.0 | 5.6 | 4.1 |
| AF064493 | LIM binding domain 2 | 0.46 | 0.14 | 5.9 | 5.6 | 2.2 | 2.9 | 8.5 | 5.8 |
| AL117567 | DKFZP566O084 protein | 0.44 | 0.22 | 5.8 | 3.3 | 2.9 | 2.3 | 5.7 | 14.9 |
| L40933 | phosphoglucomutase 5 | 0.16 | 0.03 | 5.6 | 11.0 | 4.8 | 3.5 | 8.5 | 76.3 |
| M27190 | regenerating islet-derived 1 alpha | 0.19 | 0.28 | 5.3 | 3.0 | 3.8 | 3.6 | 5.8 | 3.6 |
| AL031121 | unknown | 0.24 | 0.09 | 5.3 | 3.8 | 3.2 | 3.9 | 3.0 | 27.9 |
| U27655 | regulator of G-protein signalling | 0.24 | 0.29 | 5.0 | 9.0 | 4.5 | 8.3 | 4.2 | 4.5 |
| AB037786 | unknown | 0.12 | 0.03 | 4.7 | 54.1 | 2.8 | 2.3 | 2.2 | 11.0 |
|  | myosin-binding protein C | 0.29 | 0.13 | 4.7 | 6.5 | 6.0 | 2.4 | 6.7 | 6.3 |
| AB010962 | matrix metalloproteinase | 0.08 | 0.12 | 4.7 | 6.2 | 2.4 | 4.7 | 10.9 | 4.2 |
| AL096729 | unknown | 0.36 | 0.13 | 4.7 | 7.7 | 3.2 | 2.4 | 6.3 | 6.2 |
| AB018320 | Arg/Ab1-interacting protein | 0.16 | 0.18 | 4.6 | 7.1 | 3.0 | 3.3 | 5.8 | 8.9 |
| AK001024 | guanine nucleotide-binding protein | 0.16 | 0.11 | 4.6 | 2.0 | 9.8 | 2.6 | 7.6 | 14.1 |
| AJ275355 | unknown | 0.15 | 0.08 | 4.6 | 17.3 | 5.4 | 9.2 | 5.1 | 5.5 |
| U21931 | fructose-bisphosphatase 1 | 0.48 | 0.14 | 4.6 | 4.3 | 2.6 | 2.1 | 8.4 | 9.6 |
| X66403 | cholinergic receptor | 0.17 | 0.19 | 4.4 | 9.0 | 10.9 | 9.3 | 5.1 | 6.7 |
| X67734 | contactin2 | 0.25 | 0.09 | 4.3 | 6.8 | 3.1 | 5.8 | 7.9 | 8.4 |
| U92981 | unknown | 0.20 | 0.23 | 4.3 | 3.2 | 4.8 | 5.6 | 5.4 | 6.3 |
| X68879 | empty spiracles | 0.05 | 0.08 | 4.3 | 2.0 | 12.3 | 2.7 | 5.6 | 4.7 |
| AL137362 | unknown | 0.22 | 0.22 | 4.2 | 4.1 | 2.7 | 4.1 | 9.3 | 4.2 |
| NM_001756 | corticosteroid binding globulin | 0.28 | 0.13 | 4.1 | 10.6 | 3.9 | 2.7 | 10.3 | 5.5 |
| U80770 | unknown | 0.31 | 0.14 | 4.1 | 4.1 | 23.3 | 2.7 | 7.0 | 10.1 |
| AL109792 | unknown | 0.16 | 0.19 | 4.0 | 4.5 | 4.3 | 8.8 | 8.7 | 3.9 |
| X65962 | cytochrome P-450 | 0.33 | 0.05 | 3.8 | 25.3 | 5.7 | 5.1 | 19.8 | 12.0 |

TABLE 33-continued

Up-regulation of Polynucleotide expression in A549 cells induced by Formula C Peptides.
The peptides at a concentration of 50 μg/ml were shown to increase the expression of many polynucleotides. Peptide was incubated with the human A549 epithelial cells for 4 h and the RNA was isolated, converted into labeled cDNA probes and hybridized to Human Operon arrays (PRHU04). The intensity of polynucleotides in control, unstimulated cells are shown in the second and third columns for labeling of cDNA with the dyes Cy3 and Cy5 respectively. The "ID#: Control" columns refer to the intensity of polynucleotide expression in peptide-simulated cells divided by the intensity of unstimulated cells.

| Accession Number | Gene | control-Cy3 | control-Cy5 | ID 19: control | ID 20: control | ID 21: control | ID 22: control | ID 23: control | ID 24: control |
|---|---|---|---|---|---|---|---|---|---|
| AK001856 | unknown | 0.40 | 0.21 | 3.8 | 7.0 | 2.6 | 3.1 | 2.9 | 7.8 |
| AL022723 | MHC, class I, F | 0.55 | 0.18 | 3.7 | 5.7 | 4.4 | 2.3 | 3.3 | 5.2 |
| D38449 | putative G protein coupled receptor | 0.18 | 0.09 | 3.5 | 11.1 | 13.3 | 5.8 | 4.8 | 5.2 |
| AL137489 | unknown | 0.74 | 0.26 | 3.3 | 2.9 | 2.6 | 3.3 | 2.5 | 5.4 |
| AB000887 | small inducible cytokine subfamily A | 0.76 | 0.18 | 3.3 | 5.0 | 2.6 | 2.4 | 5.9 | 10.3 |
| NM_012450 | sulfate transporter 1 | 0.15 | 0.10 | 3.3 | 9.0 | 10.0 | 10.9 | 4.6 | 8.7 |
| U86529 | glutathione S-transferase zeta 1 | 0.55 | 0.15 | 3.2 | 6.8 | 4.4 | 2.3 | 9.3 | 5.1 |
| AK001244 | unknown | 0.79 | 0.31 | 3.2 | 5.5 | 2.3 | 2.3 | 3.9 | 2.8 |
| AL133602 | unknown | 0.16 | 0.21 | 3.1 | 7.8 | 8.7 | 2.6 | 4.1 | 5.6 |
| AB033080 | cell cycle progression 8 protein | 0.31 | 0.31 | 3.1 | 4.6 | 3.0 | 3.5 | 2.2 | 4.2 |
| AF023466 | putative glycine-N-acyltransferase | 0.27 | 0.18 | 3.1 | 5.0 | 4.2 | 7.4 | 10.1 | 3.8 |
| AL117457 | cofilin 2 | 0.68 | 0.53 | 3.0 | 4.6 | 3.3 | 2.4 | 7.4 | 3.4 |
| AC007059 | unknown | 0.37 | 0.35 | 3.0 | 5.7 | 3.1 | 2.4 | 2.6 | 2.4 |
| U60179 | growth hormone receptor | 0.34 | 0.21 | 2.9 | 3.5 | 2.3 | 3.1 | 8.0 | 4.7 |
| M37238 | phospholipase C, gamma 2 | 0.60 | 0.36 | 2.9 | 2.0 | 3.2 | 2.1 | 2.9 | 4.6 |
| L22569 | cathepsin B | 0.32 | 0.12 | 2.9 | 2.1 | 6.2 | 3.0 | 13.1 | 16.7 |
| M80359 | MAP/microtubule affinity-regulating kinase 3 | 0.37 | 0.76 | 2.9 | 3.1 | 6.1 | 7.6 | 2.1 | 3.3 |
| S70348 | Integrin beta 3 | 0.58 | 0.31 | 2.6 | 4.8 | 4.1 | 2.6 | 2.6 | 2.6 |
| L13720 | growth arrest-specific 6 | 0.36 | 0.26 | 2.4 | 2.5 | 6.8 | 4.8 | 3.9 | 3.7 |
| AL049423 | unknown | 0.33 | 0.30 | 2.4 | 3.7 | 3.8 | 2.8 | 2.9 | 3.4 |
| AL050201 | unknown | 0.68 | 0.29 | 2.2 | 3.1 | 3.7 | 3.0 | 3.0 | 2.2 |
| AF050078 | growth arrest specific 11 | 0.87 | 0.33 | 2.1 | 8.4 | 2.5 | 2.2 | 2.6 | 4.4 |
| AK001753 | hypothetical protein | 0.53 | 0.28 | 2.1 | 5.0 | 2.2 | 2.8 | 3.6 | 4.6 |
| X05323 | unknown | 0.39 | 0.13 | 2.1 | 7.8 | 2.6 | 2.4 | 21.5 | 3.5 |
| AB014548 | KIAA0648 protein | 0.61 | 0.30 | 2.0 | 2.4 | 4.8 | 3.4 | 4.9 | 3.9 |

TABLE 34

Up-regulation of Polynucleotide expression in A549 cells induced by Formula D Peptides.
The peptides at a concentration of 50 μg/ml were shown to increase the expression of many polynucleotides. Peptide was incubated with the human A549 epithelial cells for 4 h and the RNA was isolated, converted into labeled cDNA probes and hybridized to Human Operon arrays (PRHU04). The intensity of polynucleotides in control, unstimulated cells are shown in the second and third columns for labeling of cDNA with the dyes Cy3 and Cy5 respectively. The "ID#: Control" columns refer to the intensity of polynucleotide expression in peptide-simulated cells divided by the intensity of unstimulated cells.

| Accession Number | Gene | control-Cy3 | control-Cy5 | ID 26: control | ID 27: control | ID 28: control | ID 29: control | ID 30: control | ID 31: control |
|---|---|---|---|---|---|---|---|---|---|
| U68018 | MAD homolog 2 | 0.13 | 0.71 | 11.2 | 2.2 | 8.0 | 2.3 | 6.7 | 25.6 |
| NM_016015 | CGI-68 protein | 0.92 | 1.59 | 2.3 | 2.3 | 3.5 | 3.7 | 3.4 | 22.9 |
| AF071510 | lecithin retinol acyltransferase | 0.07 | 0.05 | 15.4 | 10.3 | 5.3 | 44.1 | 2.1 | 21.2 |
| AC005154 | unkown | 0.17 | 1.13 | 2.7 | 7.2 | 12.6 | 6.4 | 3.3 | 20.6 |
| M81933 | cell division cycle 25 A | 0.13 | 0.21 | 4.3 | 3.1 | 3.2 | 4.3 | 5.6 | 18.2 |

TABLE 34-continued

Up-regulation of Polynucleotide expression in A549 cells induced by Formula D Peptides.
The peptides at a concentration of 50 μg/ml were shown to increase the expression of many polynucleotides. Peptide was incubated with the human A549 epithelial cells for 4 h and the RNA was isolated, converted into labeled cDNA probes and hybridized to Human Operon arrays (PRHU04). The intensity of polynucleotides in control, unstimulated cells are shown in the second and third columns for labeling of cDNA with the dyes Cy3 and Cy5 respectively. The "ID#: Control" columns refer to the intensity of polynucleotide expression in peptide-simulated cells divided by the intensity of unstimulated cells.

| Accession Number | Gene | control-Cy3 | control-Cy5 | ID 26: control | ID 27: control | ID 28: control | ID 29: control | ID 30: control | ID 31: control |
|---|---|---|---|---|---|---|---|---|---|
| AF124735 | LIM HOX gene 2 | 0.17 | 0.21 | 2.1 | 4.4 | 5.9 | 5.2 | 7.6 | 17.0 |
| AL110125 | unknown | 0.30 | 0.08 | 5.0 | 2.7 | 6.8 | 10.2 | 2.8 | 12.0 |
| NM_004732 | potassium voltage-gated channel | 0.15 | 0.16 | 7.6 | 4.0 | 3.4 | 2.2 | 2.9 | 11.4 |
| AF030555 | fatty-acid-Coenzyme A ligase_long-chain 4 | 0.10 | 0.39 | 10.5 | 2.2 | 6.4 | 3.0 | 5.1 | 10.7 |
| AF000237 | 1-acylglycerol-3-phosphate O-acyltransferase 2 | 1.80 | 2.37 | 3.4 | 2.5 | 2.4 | 2.1 | 3.7 | 9.9 |
| AL031588 | hypothetical protein | 0.40 | 0.26 | 5.8 | 20.2 | 2.8 | 4.7 | 5.6 | 9.1 |
| AL080077 | unknown | 0.15 | 0.21 | 2.4 | 2.0 | 11.9 | 3.8 | 2.3 | 8.7 |
| NM_014366 | putative nucleotide binding protein_estradiol-induced | 0.90 | 2.52 | 2.4 | 4.3 | 2.4 | 2.6 | 3.0 | 8.6 |
| AB002359 | phosphoribosylformylglycinamidine synthase | 0.81 | 2.12 | 3.2 | 2.7 | 5.5 | 2.5 | 2.8 | 6.9 |
| U33547 | MHC class II antigen HLA-DRB6 mRNA_ | 0.14 | 0.16 | 2.5 | 5.3 | 4.5 | 5.0 | 3.1 | 6.6 |
| AL133051 | unknown | 0.09 | 0.07 | 7.7 | 6.3 | 5.4 | 23.1 | 5.4 | 6.5 |
| AK000576 | hypothetical protein | 0.27 | 0.06 | 7.1 | 9.3 | 5.0 | 6.9 | 2.9 | 6.2 |
| AF042378 | spindle pole body protein | 0.36 | 0.39 | 3.3 | 3.0 | 9.5 | 4.5 | 3.4 | 6.2 |
| AF093265 | Homer neuronal immediate early gene_3 | 0.67 | 0.53 | 2.7 | 13.3 | 6.5 | 5.0 | 2.9 | 6.2 |
| D80000 | Segregation of mitotic chromosomes 1 | 1.01 | 1.56 | 3.6 | 2.5 | 4.9 | 3.2 | 6.3 | 6.1 |
| AF035309 | proteasome 26S subunit ATPase 5 | 3.61 | 4.71 | 2.7 | 6.6 | 5.2 | 4.9 | 2.7 | 6.0 |
| M34175 | adaptor-related protein complex 2 beta 1 subunit | 4.57 | 5.13 | 3.2 | 3.1 | 4.0 | 4.6 | 2.7 | 6.0 |
| AB020659 | KLAA0852 protein | 0.18 | 0.37 | 4.1 | 7.6 | 5.7 | 4.8 | 2.5 | 5.7 |
| NM_004862 | LPS-induced TNF-alpha factor | 2.61 | 3.36 | 3.8 | 4.8 | 4.1 | 4.9 | 3.2 | 5.6 |
| U00115 | zinc finger protein 51 | 0.51 | 0.07 | 18.9 | 2.2 | 3.5 | 7.2 | 21.2 | 5.6 |
| AF088868 | fibrousheathin II | 0.45 | 0.20 | 4.7 | 10.0 | 3.2 | 6.4 | 6.0 | 5.6 |
| AK001890 | unknown | 0.42 | 0.55 | 2.4 | 3.5 | 3.6 | 2.3 | 2.2 | 5.6 |
| AL137268 | KIAA0759 protein | 0.49 | 0.34 | 3.8 | 2.3 | 5.0 | 3.5 | 3.3 | 5.4 |

TABLE 34-continued

Up-regulation of Polynucleotide expression in A549 cells induced by Formula D Peptides.

The peptides at a concentration of 50 μg/ml were shown to increase the expression of many polynucleotides. Peptide was incubated with the human A549 epithelial cells for 4 h and the RNA was isolated, converted into labeled cDNA probes and hybridized to Human Operon arrays (PRHU04). The intensity of polynucleotides in control, unstimulated cells are shown in the second and third columns for labeling of cDNA with the dyes Cy3 and Cy5 respectively. The "ID#: Control" columns refer to the intensity of polynucleotide expression in peptide-simulated cells divided by the intensity of unstimulated cells.

| Accession Number | Gene | control-Cy3 | control-Cy5 | ID 26: control | ID 27: control | ID 28: control | ID 29: control | ID 30: control | ID 31: control |
|---|---|---|---|---|---|---|---|---|---|
| X63563 | polymerase II polypeptide B | 1.25 | 1.68 | 2.5 | 8.1 | 3.4 | 4.8 | 5.2 | 5.4 |
| D12676 | CD36 antigen | 0.35 | 0.39 | 2.9 | 3.4 | 2.6 | 2.2 | 3.5 | 5.3 |
| AK000161 | hypothetical protein | 1.06 | 0.55 | 3.4 | 8.7 | 2.1 | 6.7 | 2.9 | 5.1 |
| AF052138 | unknown | 0.64 | 0.51 | 2.9 | 2.8 | 2.7 | 5.2 | 3.6 | 5.0 |
| AL096803 | unknown | 0.36 | 0.03 | 20.1 | 18.3 | 3.7 | 19.3 | 16.1 | 4.9 |
| S49953 | DNA-binding transcriptional activator | 0.70 | 0.15 | 3.7 | 4.0 | 2.1 | 6.6 | 4.0 | 4.8 |
| X89399 | RAS p21 protein activator | 0.25 | 0.10 | 8.5 | 14.9 | 4.8 | 18.6 | 4.3 | 4.8 |
| AJ005273 | antigenic determinant of recA protein | 0.70 | 0.10 | 7.6 | 11.1 | 2.8 | 9.9 | 12.0 | 4.6 |
| AK001154 | hypothetical protein | 1.70 | 0.96 | 2.4 | 4.4 | 2.9 | 8.9 | 2.4 | 4.5 |
| AL133605 | unknown | 0.26 | 0.15 | 12.4 | 4.2 | 4.4 | 3.3 | 3.3 | 4.1 |
| U71092 | G protein-coupled receptor 24 | 0.53 | 0.06 | 19.0 | 9.1 | 2.2 | 12.0 | 3.3 | 4.1 |
| AF074723 | RNA polymerase II transcriptional regulation mediator | 0.67 | 0.54 | 4.0 | 3.2 | 3.1 | 3.4 | 6.0 | 4.0 |
| AL137577 | unknown | 0.32 | 0.12 | 31.4 | 6.2 | 5.3 | 10.1 | 25.3 | 3.9 |
| AF151043 | hypothetical protein | 0.48 | 0.35 | 2.6 | 2.2 | 2.0 | 3.3 | 2.2 | 3.8 |
| AF131831 | unknown | 0.67 | 0.81 | 2.1 | 7.0 | 3.5 | 3.2 | 3.9 | 3.7 |
| D50405 | histone deacetylase 1 | 1.52 | 2.62 | 3.1 | 7.2 | 2.9 | 4.1 | 2.8 | 3.7 |
| U78305 | protein phosphatase 1D | 1.21 | 0.20 | 4.7 | 13.0 | 3.5 | 5.9 | 4.2 | 3.7 |
| AL035562 | paired box gene 1 | 0.24 | 0.01 | 30.2 | 81.9 | 5.6 | 82.3 | 6.2 | 3.7 |
| U67156 | mitogen-activated protein kinase kinase kinase 5 | 1.15 | 0.30 | 6.6 | 3.0 | 2.2 | 2.3 | 2.5 | 3.6 |
| AL031121 | unknown | 0.24 | 0.09 | 5.2 | 3.7 | 2.3 | 6.5 | 9.1 | 3.6 |
| U13666 | G protein-coupled receptor 1 | 0.34 | 0.14 | 3.8 | 5.4 | 3.1 | 3.3 | 2.8 | 3.6 |
| AB018285 | KIAA0742 protein | 0.53 | 0.13 | 14.9 | 13.9 | 5.9 | 18.5 | 15.2 | 3.5 |
| D42053 | site-1 protease | 0.63 | 0.40 | 2.6 | 7.1 | 5.6 | 9.2 | 2.6 | 3.5 |
| AK001135 | Sec23-interacting protein p125 | 0.29 | 0.53 | 5.7 | 4.5 | 3.4 | 2.6 | 11.3 | 3.4 |
| AL137461 | unknown | 0.25 | 0.02 | 23.8 | 9.0 | 2.7 | 59.2 | 12.5 | 3.3 |
| NM_006963 | zinc finger protein 22 | 0.10 | 0.08 | 3.2 | 7.6 | 3.7 | 7.9 | 11.2 | 3.2 |
| AL137540 | unknown | 0.67 | 0.79 | 3.9 | 2.6 | 5.6 | 4.2 | 3.5 | 3.1 |
| AL137718 | unknown | 0.95 | 0.18 | 4.7 | 8.0 | 4.0 | 13.3 | 3.0 | 3.1 |
| AF012086 | RAN binding protein 2-like 1 | 1.20 | 0.59 | 4.6 | 4.0 | 2.0 | 4.6 | 3.6 | 3.1 |
| S57296 | HER2/neu receptor | 0.59 | 0.17 | 7.3 | 12.1 | 2.3 | 20.0 | 22.2 | 3.0 |

TABLE 34-continued

Up-regulation of Polynucleotide expression in A549 cells induced by Formula D Peptides.
The peptides at a concentration of 50 μg/ml were shown to increase the expression of many polynucleotides. Peptide was incubated with the human A549 epithelial cells for 4 h and the RNA was isolated, converted into labeled cDNA probes and hybridized to Human Operon arrays (PRHU04). The intensity of polynucleotides in control, unstimulated cells are shown in the second and third columns for labeling of cDNA with the dyes Cy3 and Cy5 respectively. The "ID#: Control" columns refer to the intensity of polynucleotide expression in peptide-simulated cells divided by the intensity of unstimulated cells.

| Accession Number | Gene | control-Cy3 | control-Cy5 | ID 26: control | ID 27: control | ID 28: control | ID 29: control | ID 30: control | ID 31: control |
|---|---|---|---|---|---|---|---|---|---|
| NM_013329 | GC-rich sequence DNA-binding factor candidate | 0.16 | 0.08 | 6.9 | 14.3 | 9.7 | 3.3 | 7.2 | 3.0 |
| AF038664 | UDP-Gal: betaGlcNAc beta 1_4-galactosyltransferase | 0.15 | 0.03 | 13.4 | 22.2 | 5.4 | 15.8 | 17.6 | 3.0 |
| AF080579 | *Homo sapiens* integral membrane protein | 0.34 | 1.03 | 3.3 | 3.0 | 6.7 | 2.1 | 2.9 | 2.9 |
| AK001075 | hypothetical protein | 0.67 | 0.10 | 2.1 | 2.6 | 2.6 | 8.9 | 2.2 | 2.9 |
| AB011124 | KIAA0552 gene product | 0.46 | 0.04 | 9.6 | 72.0 | 6.0 | 33.9 | 13.6 | 2.9 |
| J03068 | N-acylaminoacyl-peptide hydrolase | 0.54 | 0.21 | 2.2 | 5.0 | 2.4 | 5.2 | 3.6 | 2.8 |
| D87120 | osteoblast protein | 0.87 | 0.87 | 2.2 | 2.0 | 4.7 | 2.3 | 2.0 | 2.8 |
| AB006537 | IL-1R accessory protein | 0.17 | 0.07 | 2.9 | 7.0 | 14.5 | 5.3 | 6.6 | 2.8 |
| L34587 | transcription elongation factor B | 2.49 | 1.23 | 2.2 | 16.3 | 5.0 | 15.8 | 5.5 | 2.7 |
| D31891 | SET domain_bifurcated_1 | 1.02 | 0.29 | 3.9 | 6.0 | 4.3 | 4.9 | 6.6 | 2.7 |
| D00760 | proteasome subunit_alpha type_2 | 4.97 | 4.94 | 4.1 | 2.6 | 2.0 | 2.8 | 2.7 | 2.7 |
| AC004774 | distal-less homeo box 5 | 0.25 | 0.12 | 2.3 | 6.3 | 3.8 | 5.2 | 5.2 | 2.6 |
| AL024493 | unknown | 1.46 | 0.54 | 4.8 | 13.5 | 2.1 | 11.6 | 6.8 | 2.6 |
| AB014536 | copine III | 1.80 | 1.29 | 3.2 | 9.5 | 3.8 | 6.8 | 2.6 | 2.6 |
| X59770 | IL-1R type II | 0.59 | 0.16 | 9.6 | 4.7 | 3.9 | 3.2 | 4.9 | 2.5 |
| AF052183 | unknown | 0.65 | 0.76 | 4.0 | 3.7 | 2.3 | 5.0 | 3.0 | 2.5 |
| AK000541 | hypothetical protein | 0.92 | 0.27 | 4.5 | 13.9 | 3.6 | 18.1 | 4.3 | 2.5 |
| U88528 | cAMP responsive element binding protein | 1.37 | 0.86 | 3.1 | 5.4 | 2.1 | 2.8 | 2.1 | 2.4 |
| M97925 | defensin alpha 5_Paneth cell-specific | 0.33 | 0.07 | 4.6 | 35.9 | 2.0 | 7.8 | 6.5 | 2.4 |
| NM_013393 | cell division protein FtsJ | 1.38 | 0.94 | 3.1 | 5.8 | 2.1 | 4.2 | 2.6 | 2.3 |
| X62744 | MHC class II DM alpha | 0.86 | 0.32 | 4.0 | 4.7 | 2.3 | 2.9 | 6.1 | 2.3 |
| AF251040 | putative nuclear protein | 0.64 | 0.30 | 6.7 | 3.4 | 2.9 | 3.9 | 5.7 | 2.2 |
| AK000227 | hypothetical protein | 1.49 | 0.43 | 3.4 | 7.1 | 2.3 | 3.3 | 9.1 | 2.1 |
| U88666 | SFRS protein kinase 2 | 1.78 | 0.37 | 3.4 | 5.9 | 2.6 | 8.4 | 6.1 | 2.0 |

TABLE 35

Up-regulation of Polynucleotide expression in A549 cells induced by Formula E Peptides.

The peptides at a concentration of 50 µg/ml were shown to increase the expression of many polynucleotides. Peptide was incubated with the human A549 epithelial cells for 4 h and the RNA was isolated, converted into labeled cDNA probes and hybridized to Human Operon arrays (PRHU04). The intensity of polynucleotides in control, unstimulated cells are shown in the second and third columns for labeling of cDNA with the dyes Cy3 and Cy5 respectively. The "ID#: Control" columns refer to the intensity of polynucleotide expression in peptide-simulated cells divided by the intensity of unstimulated cells.

| Accession Number | Gene | control-Cy3 | control-Cy5 | ID 33: control | ID 34: control | ID 35: control | ID 36: control | ID 37: control | ID 38: control |
|---|---|---|---|---|---|---|---|---|---|
| AL049689 | Novel human mRNA | 0.25 | 0.05 | 2.7 | 26.5 | 3.3 | 21.7 | 5.4 | 37.9 |
| AK000576 | hypothetical protein | 0.27 | 0.06 | 3.0 | 19.1 | 3.9 | 23.0 | 3.1 | 28.3 |
| X74837 | mannosidase, alpha class 1A member 1 | 0.10 | 0.07 | 5.6 | 10.0 | 10.8 | 12.3 | 12.0 | 19.9 |
| AK000258 | hypothetical protein | 0.27 | 0.07 | 14.0 | 11.1 | 7.9 | 16.1 | 6.2 | 18.9 |
| X89067 | transient receptor | 0.20 | 0.14 | 3.7 | 2.2 | 2.4 | 2.6 | 8.0 | 18.1 |
| AL137619 | unknown | 0.16 | 0.08 | 6.3 | 6.7 | 10.8 | 10.5 | 7.9 | 16.5 |
| NM_003445 | zinc finger protein | 0.17 | 0.07 | 4.0 | 23.6 | 2.9 | 13.6 | 4.3 | 14.4 |
| X03084 | complement component 1 | 0.36 | 0.15 | 2.4 | 3.1 | 2.9 | 7.7 | 3.4 | 13.7 |
| U27330 | fucosyltransferase 5 | 0.39 | 0.08 | 2.4 | 2.5 | 2.6 | 12.1 | 3.5 | 13.0 |
| AF070549 | unknown | 0.16 | 0.09 | 2.7 | 4.7 | 7.9 | 10.3 | 4.2 | 12.6 |
| AB020335 | sel-1-like | 0.19 | 0.24 | 2.9 | 2.6 | 2.0 | 7.3 | 4.7 | 12.4 |
| M26901 | renin | 0.09 | 0.12 | 14.9 | 2.2 | 7.3 | 12.0 | 20.8 | 12.0 |
| Y07828 | ring finger protein | 0.09 | 0.06 | 9.0 | 26.6 | 8.9 | 16.0 | 3.6 | 11.6 |
| AK001848 | hypothetical protein | 0.21 | 0.07 | 6.2 | 8.2 | 2.7 | 5.2 | 5.5 | 10.9 |
| NM_016331 | zinc finger protein | 0.16 | 0.08 | 7.6 | 5.1 | 7.0 | 25.5 | 5.5 | 10.9 |
| U75330 | neural cell adhesion molecule 2 | 0.42 | 0.08 | 2.5 | 3.6 | 2.0 | 5.8 | 6.2 | 9.9 |
| AB037826 | unknown | 0.16 | 0.11 | 3.8 | 6.0 | 3.4 | 13.4 | 6.0 | 9.8 |
| M34041 | adrenergic alpha-2B-receptor | 0.30 | 0.13 | 4.5 | 4.5 | 3.7 | 8.6 | 5.6 | 9.8 |
| D38449 | putative G protein coupled receptor | 0.18 | 0.09 | 2.3 | 25.8 | 11.7 | 2.3 | 3.2 | 9.5 |
| AJ250562 | transmembrane 4 superfamily member 2 | 0.13 | 0.10 | 10.0 | 8.4 | 2.2 | 8.1 | 16.3 | 9.1 |
| AK001807 | hypothetical protein | 0.18 | 0.12 | 4.2 | 5.3 | 4.6 | 3.2 | 4.0 | 8.3 |
| AL133051 | unknown | 0.09 | 0.07 | 5.1 | 13.6 | 6.0 | 9.1 | 2.2 | 8.2 |
| U43843 | Neuro-d4 homolog | 0.61 | 0.10 | 2.0 | 6.4 | 2.3 | 16.6 | 2.2 | 8.1 |
| NM_013227 | aggrecan 1 | 0.28 | 0.15 | 7.5 | 3.1 | 2.5 | 6.9 | 8.5 | 7.8 |
| AF226728 | somatostatin receptor-interacting protein | 0.23 | 0.17 | 7.0 | 3.6 | 3.1 | 5.5 | 3.5 | 7.7 |
| AK001024 | guanine nucleotide-binding protein | 0.16 | 0.11 | 3.9 | 12.3 | 2.7 | 7.4 | 3.3 | 7.0 |
| AC002302 | unknown | 0.13 | 0.14 | 16.1 | 5.8 | 5.8 | 2.6 | 9.6 | 6.2 |
| AB007958 | unknown | 0.17 | 0.27 | 2.0 | 2.3 | 11.3 | 3.3 | 3.0 | 6.1 |
| AF059293 | cytokine receptor-like factor 1 | 0.19 | 0.22 | 3.6 | 2.5 | 10.2 | 3.8 | 2.7 | 5.9 |
| V01512 | v-fos | 0.27 | 0.21 | 6.7 | 3.7 | 13.7 | 9.3 | 3.7 | 5.4 |
| U82762 | sialyltransferase 8 | 0.23 | 0.15 | 3.2 | 6.5 | 2.7 | 9.2 | 5.7 | 5.4 |
| U44059 | thyrotrophic embryonic factor | 0.05 | 0.13 | 22.9 | 7.1 | 12.5 | 7.4 | 9.7 | 5.4 |
| X05323 | antigen identified by monoclonal antibody | 0.39 | 0.13 | 4.3 | 2.5 | 2.2 | 7.4 | 2.8 | 5.1 |

TABLE 35-continued

Up-regulation of Polynucleotide expression in A549 cells induced by Formula E Peptides.
The peptides at a concentration of 50 µg/ml were shown to increase the expression of many polynucleotides. Peptide was incubated with the human A549 epithelial cells for 4 h and the RNA was isolated, converted into labeled cDNA probes and hybridized to Human Operon arrays (PRHU04). The intensity of polynucleotides in control, unstimulated cells are shown in the second and third columns for labeling of cDNA with the dyes Cy3 and Cy5 respectively. The "ID#: Control" columns refer to the intensity of polynucleotide expression in peptide-simulated cells divided by the intensity of unstimulated cells.

| Accession Number | Gene | control-Cy3 | control-Cy5 | ID 33: control | ID 34: control | ID 35: control | ID 36: control | ID 37: control | ID 38: control |
|---|---|---|---|---|---|---|---|---|---|
| U72671 | ICAM 5, | 0.25 | 0.14 | 5.3 | 2.7 | 3.7 | 10.0 | 3.2 | 4.8 |
| AL133626 | hypothetical protein | 0.26 | 0.25 | 2.2 | 4.2 | 2.9 | 3.0 | 2.6 | 4.7 |
| X96401 | MAX binding protein | 0.31 | 0.29 | 6.9 | 2.3 | 4.9 | 3.1 | 2.9 | 4.6 |
| AL117533 | unknown | 0.05 | 0.26 | 8.2 | 2.7 | 11.1 | 2.5 | 11.9 | 4.5 |
| AK001550 | hypothetical protein | 0.10 | 0.30 | 8.0 | 2.0 | 4.9 | 2.1 | 7.8 | 4.5 |
| AB032436 | *Homo sapiens* BNPI mRNA | 0.14 | 0.21 | 5.1 | 2.2 | 9.1 | 4.5 | 6.4 | 4.4 |
| AL035447 | hypothetical protein | 0.28 | 0.23 | 4.3 | 3.7 | 8.7 | 5.2 | 3.7 | 4.2 |
| U09414 | zinc finger protein | 0.28 | 0.25 | 4.0 | 2.2 | 4.7 | 3.3 | 7.2 | 4.2 |
| AK001256 | unknown | 0.09 | 0.08 | 5.3 | 6.5 | 31.1 | 12.7 | 6.4 | 4.1 |
| L14813 | carboxyl ester lipase-like | 0.64 | 0.21 | 2.7 | 6.2 | 3.1 | 2.1 | 3.4 | 3.9 |
| AF038181 | unknowan | 0.06 | 0.18 | 34.1 | 6.4 | 4.5 | 8.7 | 11.3 | 3.9 |
| NM_001486 | glucokinase | 0.21 | 0.08 | 3.0 | 2.2 | 6.5 | 12.4 | 5.7 | 3.9 |
| AB033000 | hypothetical protein | 0.24 | 0.22 | 3.4 | 3.3 | 7.1 | 5.5 | 4.5 | 3.8 |
| AL117567 | DKFZP566O084 protein | 0.44 | 0.22 | 2.2 | 2.7 | 3.9 | 4.0 | 4.5 | 3.7 |
| NM_012126 | carbohydrate sulfotransferase 5 | 0.31 | 0.20 | 5.5 | 5.4 | 3.8 | 5.5 | 2.6 | 3.5 |
| AL031687 | unknown | 0.16 | 0.27 | 5.9 | 2.6 | 3.4 | 2.3 | 4.9 | 3.5 |
| X04506 | apolipoprotein B | 0.29 | 0.32 | 5.4 | 4.4 | 6.9 | 5.5 | 2.1 | 3.5 |
| NM_006641 | CCR 9 | 0.35 | 0.11 | 3.3 | 3.3 | 2.2 | 16.5 | 2.3 | 3.5 |
| Y00970 | acrosin | 0.12 | 0.14 | 8.2 | 8.8 | 3.1 | 6.2 | 17.5 | 3.4 |
| X67098 | rTS beta protein | 0.19 | 0.26 | 2.4 | 3.1 | 7.8 | 3.5 | 4.4 | 3.3 |
| U51990 | pre-mRNA splicing factor | 0.56 | 0.19 | 2.2 | 3.0 | 2.8 | 13.7 | 2.9 | 3.0 |
| AF030555 | fatty-acid-Coenzyme A | 0.10 | 0.39 | 3.5 | 6.9 | 13.3 | 4.4 | 7.5 | 2.9 |
| AL009183 | TNFR superfamily, member 9 | 0.46 | 0.19 | 6.0 | 4.1 | 2.8 | 8.6 | 2.6 | 2.8 |
| AF045941 | sciellin | 0.16 | 0.21 | 11.6 | 2.4 | 2.8 | 2.2 | 4.1 | 2.8 |
| AF072756 | A kinase anchor protein 4 | 0.33 | 0.07 | 2.5 | 5.3 | 3.9 | 32.7 | 2.3 | 2.7 |
| X78678 | ketohexokinase | 0.10 | 0.20 | 18.0 | 3.5 | 4.1 | 2.5 | 14.6 | 2.6 |
| AL031734 | unknown | 0.03 | 0.39 | 43.7 | 2.3 | 41.7 | 4.0 | 10.8 | 2.5 |
| D87717 | KIAA0013 gene product | 0.35 | 0.42 | 4.2 | 2.3 | 3.6 | 2.6 | 2.9 | 2.5 |
| U01824 | solute carrier family 1 | 0.42 | 0.29 | 4.8 | 2.3 | 4.2 | 7.1 | 4.2 | 2.4 |
| AF055899 | solute carrier family 27 | 0.14 | 0.31 | 9.5 | 12.3 | 7.4 | 4.7 | 6.6 | 2.3 |
| U22526 | lanosterol synthase | 0.09 | 0.45 | 4.1 | 3.4 | 10.4 | 2.2 | 17.9 | 2.3 |
| AB032963 | unknown | 0.19 | 0.34 | 6.3 | 6.1 | 2.9 | 2.1 | 5.7 | 2.2 |
| NM_015974 | lambda-crystallin | 0.17 | 0.25 | 11.4 | 2.8 | 5.9 | 2.4 | 5.8 | 2.2 |
| X82200 | stimulated transacting factor | 0.23 | 0.15 | 8.2 | 3.4 | 3.0 | 2.8 | 11.3 | 2.2 |
| AL137522 | unknown | 0.12 | 0.26 | 12.1 | 3.7 | 12.6 | 6.9 | 4.3 | 2.2 |
| Z99916 | crystallin, beta B3 | 0.28 | 0.65 | 2.5 | 2.1 | 3.6 | 2.2 | 2.6 | 2.1 |
| AF233442 | ubiquitin specific protease 21 | 0.41 | 0.31 | 2.6 | 3.6 | 3.6 | 4.5 | 3.4 | 2.1 |
| AK001927 | hypothetical protein | 0.24 | 0.52 | 7.6 | 5.6 | 5.0 | 2.5 | 4.1 | 2.0 |

TABLE 36

Up-regulation of Polynucleotide expression in A549 cells induced by
Formula F Peptides.
The peptides at a concentration of 50 µg/ml were shown to increase the
expression of many polynucleotides. Peptide was incubated with the human A549
epithelial cells for 4 h and the RNA was isolated, converted into labeled cDNA probes
and hybridized to Human Operon arrays (PRHU04). The intensity of polynucleotides in
control, unstimulated cells are shown in the second and third columns for labeling of
cDNA with the dyes Cy3 and Cy5 respectively. The "Ratio ID#: Control" columns refer
to the intensity of polynucleotide expression in peptide-simulated cells divided by the
intensity of unstimulated cells.

| Accession Number | Gene | control-Cy3 | control-Cy5 | Ratio ID 40: control | Ratio ID 42: control | Ratio ID 43: control | Ratio ID 44: control | Ratio ID 45: control |
|---|---|---|---|---|---|---|---|---|
| AF025840 | polymerase epsilon 2 | 0.34 | 0.96 | 3.4 | 2.0 | 2.0 | 2.1 | 4.3 |
| AF132495 | CGI-133 protein | 0.83 | 0.67 | 3.0 | 2.2 | 2.6 | 2.8 | 5.1 |
| AL137682 | hypothetical protein | 0.73 | 0.40 | 2.0 | 5.3 | 4.8 | 2.9 | 8.2 |
| U70426 | regulator of G-protein signalling 16 | 0.23 | 0.25 | 3.1 | 3.0 | 5.3 | 3.1 | 12.2 |
| AK001135 | Sec23-interacting protein p125 | 0.29 | 0.53 | 3.2 | 2.6 | 3.3 | 14.4 | 5.2 |
| AB023155 | KIAA0938 protein | 0.47 | 0.21 | 2.7 | 4.8 | 8.1 | 4.2 | 10.4 |
| AB033080 | cell cycle progression 8 protein | 0.31 | 0.31 | 4.4 | 2.2 | 5.9 | 4.3 | 6.9 |
| AF061836 | Ras association domain family 1 | 0.29 | 0.31 | 3.2 | 2.5 | 11.1 | 18.8 | 6.8 |
| AK000298 | hypothetical protein | 0.48 | 0.27 | 3.3 | 2.2 | 7.1 | 5.6 | 7.7 |
| L75847 | zinc finger protein | 0.35 | 0.52 | 3.2 | 3.0 | 4.0 | 3.0 | 3.9 |
| X97267 | protein tyrosine phosphatase | 0.19 | 0.24 | 4.1 | 9.3 | 2.4 | 4.2 | 8.3 |
| Z11933 | POU domain class 3 TF 2 | 0.09 | 0.23 | 8.7 | 2.5 | 3.6 | 4.3 | 8.2 |
| AB037744 | unknown | 0.37 | 0.57 | 2.6 | 2.9 | 2.7 | 3.0 | 3.1 |
| U90908 | unknown | 0.12 | 0.16 | 11.8 | 7.7 | 3.4 | 7.8 | 11.2 |
| AL050139 | unknown | 0.29 | 0.60 | 5.2 | 2.4 | 3.3 | 3.0 | 2.8 |
| AB014615 | fibroblast growth factor 8 | 0.19 | 0.07 | 5.4 | 3.5 | 8.5 | 3.2 | 22.7 |
| M28825 | CD1A antigen | 0.51 | 0.36 | 4.1 | 2.6 | 2.0 | 4.6 | 4.4 |
| U27330 | fucosyltransferase 5 | 0.39 | 0.08 | 3.3 | 2.1 | 24.5 | 8.2 | 19.3 |
| NM_006963 | zinc finger protein | 0.10 | 0.08 | 10.4 | 12.6 | 12.3 | 29.2 | 20.5 |
| AF093670 | peroxisomal biogenesis factor | 0.44 | 0.53 | 4.0 | 2.6 | 2.6 | 4.3 | 2.9 |
| AK000191 | hypothetical protein | 0.50 | 0.18 | 2.3 | 3.6 | 4.4 | 2.2 | 8.2 |
| AB022847 | unknown | 0.39 | 0.24 | 2.1 | 6.9 | 4.5 | 2.8 | 6.2 |
| AK000358 | microfibrillar-associated protein 3 | 0.28 | 0.28 | 5.7 | 2.0 | 3.5 | 5.2 | 5.2 |
| X74837 | mannosidase_ alpha class 1A | 0.10 | 0.07 | 13.1 | 18.4 | 23.6 | 16.3 | 20.8 |
| AF053712 | TNF superfamily_ member 11 | 0.17 | 0.08 | 11.3 | 9.3 | 13.4 | 10.6 | 16.6 |
| AL133114 | DKFZP586P2421 protein | 0.11 | 0.32 | 8.5 | 3.4 | 4.9 | 5.3 | 4.3 |
| AF049703 | E74-like factor 5 | 0.22 | 0.24 | 5.1 | 6.0 | 3.3 | 2.7 | 5.4 |
| AL137471 | hypothetical protein | 0.29 | 0.05 | 4.0 | 15.0 | 10.1 | 2.7 | 25.3 |
| AL035397 | unknown | 0.33 | 0.14 | 2.3 | 2.8 | 10.6 | 4.6 | 9.3 |
| AL035447 | hypothetical protein | 0.28 | 0.23 | 3.8 | 6.8 | 2.7 | 3.0 | 5.7 |
| X55740 | CD73 | 0.41 | 0.61 | 2.1 | 3.3 | 2.9 | 3.2 | 2.1 |
| NM_004909 | taxol resistance associated gene 3 | 0.20 | 0.22 | 3.9 | 2.9 | 6.5 | 3.2 | 5.6 |
| AF233442 | ubiquitin specific protease | 0.41 | 0.31 | 2.9 | 4.7 | 2.7 | 3.5 | 3.9 |
| U92980 | unknown | 0.83 | 0.38 | 4.2 | 4.1 | 4.8 | 2.3 | 3.1 |
| AF105424 | myosin heavy polypeptide-like | 0.30 | 0.22 | 2.8 | 3.3 | 4.4 | 2.3 | 5.3 |
| M26665 | histatin 3 | 0.29 | 0.26 | 7.9 | 3.5 | 4.6 | 3.5 | 4.5 |
| AF083898 | neuro-oncological ventral antigen 2 | 0.20 | 0.34 | 18.7 | 3.8 | 2.2 | 3.6 | 3.5 |
| AJ009771 | ariadne_ Drosophila_ homolog of | 0.33 | 0.06 | 2.3 | 17.6 | 15.9 | 2.5 | 20.3 |

TABLE 36-continued

Up-regulation of Polynucleotide expression in A549 cells induced by Formula F Peptides.

The peptides at a concentration of 50 µg/ml were shown to increase the expression of many polynucleotides. Peptide was incubated with the human A549 epithelial cells for 4 h and the RNA was isolated, converted into labeled cDNA probes and hybridized to Human Operon arrays (PRHU04). The intensity of polynucleotides in control, unstimulated cells are shown in the second and third columns for labeling of cDNA with the dyes Cy3 and Cy5 respectively. The "Ratio ID#: Control" columns refer to the intensity of polynucleotide expression in peptide-simulated cells divided by the intensity of unstimulated cells.

| Accession Number | Gene | control-Cy3 | control-Cy5 | Ratio ID 40: control | Ratio ID 42: control | Ratio ID 43: control | Ratio ID 44: control | Ratio ID 45: control |
|---|---|---|---|---|---|---|---|---|
| AL022393 | hypothetical protein P1 | 0.05 | 0.33 | 32.9 | 2.4 | 3.0 | 69.4 | 3.4 |
| AF039400 | chloride channel_calcium activated_family member 1 | 0.11 | 0.19 | 8.4 | 2.9 | 5.1 | 18.1 | 5.9 |
| AJ012008 | dimethylarginine dimethylaminohydrolase 2 | 0.42 | 0.43 | 5.1 | 3.3 | 3.2 | 6.2 | 2.6 |
| AK000542 | hypothetical protein | 0.61 | 0.24 | 2.1 | 4.5 | 5.0 | 3.7 | 4.4 |
| AL133654 | unknown | 0.27 | 0.40 | 2.8 | 2.1 | 2.5 | 2.5 | 2.6 |
| AL137513 | unknown | 0.43 | 0.43 | 6.4 | 3.2 | 3.8 | 2.3 | 2.3 |
| U05227 | GTP-binding protein | 0.38 | 0.36 | 5.0 | 3.1 | 3.1 | 2.2 | 2.8 |
| D38449 | putative G protein coupled receptor | 0.18 | 0.09 | 5.8 | 6.7 | 6.7 | 9.1 | 10.4 |
| U80770 | unknown | 0.31 | 0.14 | 3.9 | 3.8 | 6.6 | 3.1 | 6.8 |
| X61177 | IL-5R alpha | 0.40 | 0.27 | 2.6 | 4.4 | 9.8 | 8.1 | 3.6 |
| U35246 | vacuolar protein sorting 45A | 0.15 | 0.42 | 5.8 | 2.8 | 2.6 | 4.5 | 2.2 |
| AB017016 | brain-specific protein p25 alpha | 0.27 | 0.29 | 6.0 | 2.6 | 3.4 | 3.1 | 3.1 |
| X82153 | cathepsin K | 0.45 | 0.20 | 4.2 | 5.2 | 4.8 | 4.4 | 4.6 |
| AC005162 | probable carboxypeptidase precursor | 0.12 | 0.28 | 11.9 | 3.4 | 6.8 | 18.7 | 3.2 |
| AL137502 | unknown | 0.22 | 0.16 | 3.9 | 4.9 | 7.3 | 3.9 | 5.3 |
| U66669 | 3-hydroxyisobutyryl-Coenzyme A hydrolase | 0.30 | 0.40 | 10.3 | 3.5 | 5.2 | 2.3 | 2.1 |
| AK000102 | unknown | 0.39 | 0.30 | 2.8 | 5.3 | 5.2 | 4.1 | 2.8 |
| AF034970 | docking protein 2 | 0.28 | 0.05 | 3.3 | 8.5 | 15.7 | 4.0 | 17.3 |
| AK000534 | hypothetical protein | 0.13 | 0.29 | 6.8 | 2.3 | 4.0 | 20.6 | 2.9 |
| J04599 | biglycan | 0.39 | 0.30 | 4.0 | 3.7 | 4.0 | 4.8 | 2.8 |
| AL133612 | unknown | 0.62 | 0.33 | 2.7 | 3.4 | 5.2 | 3.0 | 2.5 |
| D10495 | protein kinase C delta | 0.18 | 0.10 | 12.0 | 20.7 | 8.7 | 6.8 | 8.1 |
| X58467 | cytochrome P450 | 0.07 | 0.24 | 15.4 | 4.7 | 7.9 | 34.4 | 3.4 |
| AF131806 | unknown | 0.31 | 0.25 | 2.6 | 3.4 | 5.7 | 7.0 | 3.2 |
| AK000351 | hypothetical protein | 0.34 | 0.13 | 4.0 | 6.9 | 5.5 | 2.8 | 6.3 |
| AF075050 | hypothetical protein | 0.55 | 0.09 | 2.7 | 17.8 | 5.1 | 2.2 | 8.3 |
| AK000566 | hypothetical protein unknown | 0.15 | 0.35 | 6.7 | 2.2 | 6.8 | 6.4 | 2.1 |
| U43328 | cartilage linking protein 1 | 0.44 | 0.19 | 2.5 | 6.2 | 6.9 | 7.8 | 3.8 |
| AF045941 | sciellin | 0.16 | 0.21 | 6.8 | 7.5 | 4.8 | 6.9 | 3.4 |
| U27655 | regulator of G-protein signalling 3 | 0.24 | 0.29 | 5.5 | 4.9 | 2.9 | 4.9 | 2.4 |
| AK000058 | hypothetical protein | 0.25 | 0.15 | 5.0 | 9.7 | 16.4 | 2.7 | 4.5 |
| AL035364 | hypothetical protein | 0.32 | 0.26 | 4.4 | 4.2 | 7.3 | 2.8 | 2.6 |
| AK001864 | unknown | 0.40 | 0.25 | 3.7 | 3.7 | 4.6 | 3.2 | 2.6 |
| AB015349 | unknown | 0.14 | 0.24 | 10.5 | 2.8 | 3.7 | 8.0 | 2.7 |
| V00522 | MHC class II DR beta 3 | 0.62 | 0.22 | 4.8 | 3.9 | 4.7 | 2.5 | 3.0 |
| U75330 | neural cell adhesion molecule 2 | 0.42 | 0.08 | 2.1 | 9.6 | 13.2 | 3.3 | 7.8 |
| NM_007199 | IL-1R-associated kinase M | 0.15 | 0.25 | 8.7 | 7.8 | 8.6 | 16.1 | 2.5 |

TABLE 36-continued

Up-regulation of Polynucleotide expression in A549 cells induced by Formula F Peptides.
The peptides at a concentration of 50 μg/ml were shown to increase the expression of many polynucleotides. Peptide was incubated with the human A549 epithelial cells for 4 h and the RNA was isolated, converted into labeled cDNA probes and hybridized to Human Operon arrays (PRHU04). The intensity of polynucleotides in control, unstimulated cells are shown in the second and third columns for labeling of cDNA with the dyes Cy3 and Cy5 respectively. The "Ratio ID#: Control" columns refer to the intensity of polynucleotide expression in peptide-simulated cells divided by the intensity of unstimulated cells.

| Accession Number | Gene | control-Cy3 | control-Cy5 | Ratio ID 40: control | Ratio ID 42: control | Ratio ID 43: control | Ratio ID 44: control | Ratio ID 45: control |
|---|---|---|---|---|---|---|---|---|
| D30742 | calcium/calmodulin-dependent protein kinase IV | 0.28 | 0.09 | 6.2 | 28.7 | 7.4 | 2.4 | 6.8 |
| X05978 | cystatin A | 0.63 | 0.17 | 2.7 | 4.8 | 9.4 | 2.2 | 3.6 |
| AF240467 | TLR-7 | 0.11 | 0.10 | 13.8 | 13.3 | 4.7 | 7.7 | 4.9 |

TABLE 37

Up-regulation of Polynucleotide expression in A549 cells induced by Formula G and additional Peptides.
The peptides at a concentration of 50 μg/ml were shown to increase the expression of many polynucleotides. Peptide was incubated with the human A549 epithelial cells for 4 h and the RNA was isolated, converted into labelled cDNA probes and hybridised to Human Operon arrays (PRHU04). The intensity of polynucleotides in control, unstimulated cells are shown in the second and third columns for labelling of cDNA with the dyes Cy3 and Cy5 respectively. The "Ratio ID#: Control" columns refer to the intensity of polynucleotide expression in peptide-simulated cells divided by the intensity of unstimulated cells. Accession numbers and gene designations are U00115, zinc finger protein; M91036, hemoglobin gamma G; K000070, hypothetical protein; AF055899, solute carrier family 27; AK001490, hypothetical protein; X97674, nuclear receptor coactivator 2; AB022847, unknown; AJ275986, transcription factor; D10495, protein kinase C, delta; L36642, EphA7; M31166, pentaxin-related gene; AF176012, unknown; AF072756, A kinase anchor protein 4; NM_014439, IL-1 Superfamily z; AJ271351, putative transcriptional regulator; AK000576, hypothetical protein; AJ272265, secreted phosphoprotein 2; AL122038, hypothetical protein; AK000307, hypothetical protein; AB029001, KIAA1078 protein; U62437, cholinergic receptor; AF064854, unknown; AL031588, hypothetical protein; X89399, RAS p21 protein activator; D45399, phosphodiesterase; AB037716, hypothetical protein; X79981, cadherin 5; AF034208, RIG-like 7-1; AL133355, chromosome 21 open reading frame 53; NM_016281, STE20-like kinase; AF023614, transmembrane activator and CAML interactor; AF056717, ash2-like; AB029039, KIAA1116 protein; J03634, inhibin, beta A; U80764, unknown; AB032963, unknown; X82835, sodium channel, voltage-gated, type IX

| Accession Number | control-Cy3 | control-Cy5 | ID 53: control | ID 54: control | ID 47: control | ID 48: control | ID 49: control | ID 50: control | ID 51: control | ID 52: control |
|---|---|---|---|---|---|---|---|---|---|---|
| U00115 | 0.51 | 0.07 | 27.4 | 7.3 | 2.4 | 3.1 | 4.8 | 8.3 | 3.5 | 20.0 |
| M91036 | 0.22 | 0.02 | 39.1 | 32.5 | 5.2 | 2.2 | 37.0 | 6.0 | 16.2 | 18.0 |
| AK000070 | 0.36 | 0.18 | 3.8 | 7.6 | 2.6 | 15.1 | 12.2 | 9.9 | 17.2 | 15.3 |
| AF055899 | 0.14 | 0.31 | 6.7 | 3.7 | 9.7 | 10.0 | 2.2 | 16.7 | 5.4 | 14.8 |
| AK001490 | 0.05 | 0.02 | 14.1 | 35.8 | 3.2 | 28.6 | 25.0 | 20.2 | 56.5 | 14.1 |
| X97674 | 0.28 | 0.28 | 3.2 | 3.7 | 4.0 | 10.7 | 3.3 | 3.1 | 4.0 | 13.2 |
| AB022847 | 0.39 | 0.24 | 4.1 | 4.4 | 4.5 | 2.7 | 3.7 | 10.4 | 5.0 | 11.3 |
| AJ275986 | 0.26 | 0.35 | 5.8 | 2.3 | 5.7 | 2.2 | 2.5 | 9.7 | 4.3 | 11.1 |
| D10495 | 0.18 | 0.10 | 8.0 | 3.4 | 4.6 | 2.0 | 6.9 | 2.5 | 12.7 | 10.3 |
| L36642 | 0.26 | 0.06 | 5.8 | 14.2 | 2.6 | 4.1 | 8.9 | 3.4 | 6.5 | 6.6 |
| M31166 | 0.31 | 0.12 | 4.8 | 3.8 | 12.0 | 3.6 | 9.8 | 2.4 | 8.8 | 6.4 |
| AF176012 | 0.45 | 0.26 | 3.1 | 2.9 | 2.8 | 2.6 | 2.3 | 6.9 | 3.0 | 5.8 |
| AF072756 | 0.33 | 0.07 | 9.9 | 9.3 | 4.4 | 4.3 | 3.2 | 4.9 | 11.9 | 5.4 |
| NM_014439 | 0.47 | 0.07 | 12.0 | 7.1 | 3.3 | 3.3 | 4.7 | 5.9 | 5.0 | 5.4 |
| AJ271351 | 0.46 | 0.12 | 3.4 | 3.5 | 2.3 | 4.7 | 2.3 | 2.7 | 6.9 | 5.2 |
| AK000576 | 0.27 | 0.06 | 7.4 | 15.7 | 2.9 | 4.7 | 9.0 | 2.4 | 8.2 | 5.1 |
| AJ272265 | 0.21 | 0.09 | 6.2 | 7.9 | 2.3 | 3.7 | 10.3 | 4.5 | 4.6 | 4.7 |
| AL122038 | 0.46 | 0.06 | 6.7 | 4.5 | 2.6 | 4.3 | 16.4 | 6.5 | 26.6 | 4.6 |
| AK000307 | 0.23 | 0.09 | 3.7 | 4.0 | 4.3 | 3.2 | 5.3 | 2.9 | 13.1 | 4.4 |
| AB029001 | 0.52 | 0.21 | 14.4 | 4.3 | 4.6 | 4.4 | 4.8 | 21.9 | 3.2 | 4.2 |
| U62437 | 0.38 | 0.13 | 12.6 | 6.5 | 4.2 | 6.7 | 2.2 | 3.7 | 4.8 | 3.9 |
| AF064854 | 0.15 | 0.16 | 2.6 | 2.9 | 6.2 | 8.9 | 14.4 | 5.0 | 9.1 | 3.9 |
| AL031588 | 0.40 | 0.26 | 8.3 | 5.2 | 2.8 | 3.3 | 5.3 | 9.0 | 5.6 | 3.4 |
| X89399 | 0.25 | 0.10 | 15.8 | 12.8 | 7.4 | 4.2 | 16.7 | 6.9 | 12.7 | 3.3 |
| D45399 | 0.21 | 0.18 | 3.0 | 4.7 | 3.3 | 4.4 | 8.7 | 5.3 | 5.1 | 3.3 |

TABLE 37-continued

Up-regulation of Polynucleotide expression in A549 cells induced by Formula G and additional Peptides.
The peptides at a concentration of 50 μg/ml were shown to increase the expression of many polynucleotides. Peptide was incubated with the human A549 epithelial cells for 4 h and the RNA was isolated, converted into labelled cDNA probes and hybridised to Human Operon arrays (PRHU04). The intensity of polynucleotides in control, unstimulated cells are shown in the second and third columns for labelling of cDNA with the dyes Cy3 and Cy5 respectively. The "Ratio ID#: Control" columns refer to the intensity of polynucleotide expression in peptide-simulated cells divided by the intensity of unstimulated cells. Accession numbers and gene designations are U00115, zinc finger protein; M91036, hemoglobin gamma G; K000070, hypothetical protein; AF055899, solute carrier family 27; AK001490, hypothetical protein; X97674, nuclear receptor coactivator 2; AB022847, unknown; AJ275986, transcription factor; D10495, protein kinase C, delta; L36642, EphA7; M31166, pentaxin-related gene; AF176012, unknown; AF072756, A kinase anchor protein 4; NM_014439, IL-1 Superfamily z; AJ271351, putative transcriptional regulator; AK000576, hypothetical protein; AJ272265, secreted phosphoprotein 2; AL122038, hypothetical protein; AK000307, hypothetical protein; AB029001, KIAA1078 protein; U62437, cholinergic receptor; AF064854, unknown; AL031588, hypothetical protein; X89399, RAS p21 protein activator; D45399, phosphodiesterase; AB037716, hypothetical protein; X79981, cadherin 5; AF034208, RIG-like 7-1; AL133355, chromosome 21 open reading frame 53; NM_016281, STE20-like kinase; AF023614, transmembrane activator and CAML interactor; AF056717, ash2-like; AB029039, KIAA1116 protein; J03634, inhibin, beta A; U80764, unknown; AB032963, unknown; X82835, sodium channel, voltage-gated, type IX

| Accession Number | control-Cy3 | control-Cy5 | ID 53: control | ID 54: control | ID 47: control | ID 48: control | ID 49: control | ID 50: control | ID 51: control | ID 52: control |
|---|---|---|---|---|---|---|---|---|---|---|
| AB037716 | 0.36 | 0.40 | 5.1 | 7.5 | 2.6 | 2.1 | 3.5 | 3.1 | 2.4 | 2.8 |
| X79981 | 0.34 | 0.10 | 4.7 | 7.2 | 3.2 | 4.6 | 6.5 | 5.1 | 5.8 | 2.7 |
| AF034208 | 0.45 | 0.24 | 2.7 | 10.9 | 2.1 | 3.7 | 2.3 | 5.9 | 2.2 | 2.5 |
| AL133355 | 0.22 | 0.23 | 2.3 | 3.4 | 7.3 | 2.7 | 3.3 | 4.3 | 2.8 | 2.5 |
| NM_016281 | 0.40 | 0.19 | 6.6 | 10.6 | 2.1 | 2.8 | 5.0 | 11.2 | 10.6 | 2.5 |
| AF023614 | 0.11 | 0.42 | 2.2 | 2.2 | 6.0 | 7.5 | 5.0 | 2.7 | 2.0 | 2.4 |
| AF056717 | 0.43 | 0.62 | 4.3 | 3.2 | 5.1 | 4.0 | 4.6 | 9.7 | 3.1 | 2.2 |
| AB029039 | 0.79 | 0.49 | 2.7 | 3.3 | 3.7 | 2.0 | 2.3 | 2.4 | 4.8 | 2.2 |
| J03634 | 0.40 | 0.12 | 3.7 | 2.3 | 2.3 | 4.0 | 10.5 | 4.1 | 9.1 | 2.2 |
| U80764 | 0.31 | 0.18 | 2.3 | 7.4 | 4.2 | 2.3 | 5.1 | 3.3 | 8.8 | 2.1 |
| AB032963 | 0.19 | 0.34 | 4.0 | 7.3 | 5.0 | 3.0 | 2.9 | 6.7 | 3.8 | 2.1 |
| X82835 | 0.25 | 0.38 | 2.0 | 2.7 | 2.9 | 7.7 | 3.3 | 3.1 | 3.5 | 2.0 |

EXAMPLE 5

Induction of Chemokines in Cell Lines, Whole Human Blood, and in Mice By Peptides The murine macrophage cell line RAW 264.7, THP-1 cells (human monocytes), a human epithelial cell line (A549), human bronchial epithelial cells (16HBEo14), and whole human blood were used. HBE cells were grown in MEM with Earle's. THP-1 cells were grown and maintained in RPMI 1640 medium. The RAW and A549 cell lines were maintained in DMEM supplemented with 10% fetal calf serum. The cells were seeded in 24 well plates at a density of $10^6$ cells per well in DMEM (see above) and A549 cells were seeded in 24 well plates at a density of $10^5$ cells per well in DMEM (see above) and both were incubated at 37° C. in 5% $CO_2$ overnight. DMEM was aspirated from cells grown overnight and replaced with fresh medium. After incubation of the cells with peptide, the release of chemokines into the culture supernatant was determined by ELISA (R&D Systems, Minneapolis, Minn.).

Animal studies were approved by the UBC Animal Care Committee (UBC ACC # A01-0008). BALB/c mice were purchased from Charles River Laboratories and housed in standard animal facilities. Age, sex and weight matched adult mice were anaesthetized with an intraperitoneal injection of Avertin (4.4 mM 2-2-2-tribromoethanol, 2.5% 2-methyl-2-butanol, in distilled water), using 200 μl per 10 g body weight. The instillation was performed using a non-surgical, intratracheal instillation method adapted from Ho and Furst 1973. Briefly, the anaesthetized mouse was placed with its upper teeth hooked over a wire at the top of a support frame with its jaw held open and a spring pushing the thorax forward to position the pharynx, larynx and trachea in a vertical straight line. The airway was illuminated externally and an intubation catheter was inserted into the clearly illuminated tracheal lumen. Twenty-μl of peptide suspension or sterile water was placed in a well at the proximal end of the catheter and gently instilled into the trachea with 200 μl of air. The animals were maintained in an upright position for 2 minutes after instillation to allow the fluid to drain into the respiratory tree. After 4 hours the mice were euthanaised by intraperitoneal injection of 300 mg/kg of pentobarbital. The trachea was exposed; an intravenous catheter was passed into the proximal trachea and tied in place with suture thread. Lavage was performed by introducing 0.75 ml sterile PBS into the lungs via the tracheal cannula and then after a few seconds, withdrawing the fluid. This was repeated 3 times with the same sample of PBS. The lavage fluid was placed in a tube on ice and the total recovery volume per mouse was approximately 0.5 ml. The bronchoalveolar lavage (BAL) fluid was centrifuged at 1200 rpm for 10 min, the clear supernatant removed and tested for TNF-α and MCP-1 by ELISA.

The up-regulation of chemokines by cationic peptides was confirmed in several different systems. The murine MCP-1, a homologue of the human MCP-1, is a member of the β(C-C) chemokine family. MCP-1 has been demonstrated to recruit monocytes, NK cells and some T lymphocytes. When RAW 264.7 macrophage cells and whole human blood from 3 donors were stimulated with increasing concentrations of peptide, SEQ ID NO: 1, they produced significant levels of MCP-1 in their supernatant, as judged by ELISA (Table 36). RAW 264.7 cells stimulated with peptide concentrations ranging from 20-50 µg/ml for 24 hr produced significant levels of MCP-1 (200-400 pg/ml above background). When the cells (24h) and whole blood (4h) were stimulated with 100 µg/ml of LL-37, high levels of MCP-1 were produced.

The effect of cationic peptides on chemokine induction was also examined in a completely different cell system, A549 human epithelial cells. Interestingly, although these cells produce MCP-1 in response to LPS, and this response could be antagonized by peptide; there was no production of MCP-1 by A549 cells in direct response to peptide, SEQ ID NO: 1. Peptide SEQ ID NO: 1 at high concentrations, did however induce production of IL-8, a neutrophil specific chemokine (Table 37). Thus, SEQ ID NO: 1 can induce a different spectrum of responses from different cell types and at different concentrations. A number of peptides from each of the formula groups were tested for their ability to induce IL-8 in A549 cells (Table 38). Many of these peptides at a low concentration, 10 µg/ml induced IL-8 above background levels. At high concentrations (100 µg/ml) SEQ ID NO: 13 was also found to induce IL-8 in whole human blood (Table 39). Peptide SEQ ID NO: 2 also significantly induced IL-8 in HBE cells (Table 40) and undifferentiated THP-1 cells (Table 41).

BALB/c mice were given SEQ ID NO: 1 or endotoxin-free water by intratracheal instillation and the levels of MCP-1 and TNF-α examined in the bronchioalveolar lavage fluid after 3-4 hr. It was found that the mice treated with 50 µg/ml peptide, SEQ ID NO: 1 produced significantly increased levels of MCP-1 over mice given water or anesthetic alone (Table 42). This was not a pro-inflammatory response to peptide, SEQ ID NO: 1 since peptide did not significantly induce more TNF-α a than mice given water or anesthetic alone. peptide, SEQ ID NO: 1 was also found not to significantly induce TNF-α production by RAW 264.7 cells and bone marrow-derived macrophages treated with peptide, SEQ ID NO: 1 (up to 100 µg/ml) (Table 43). Thus, peptide, SEQ ID NO: 1 selectively induces the production of chemokines without inducing the production of inflammatory mediators such as TNF-α. This illustrates the dual role of peptide, SEQ ID NO: 1 as a factor that can block bacterial product-induced inflammation while helping to recruit phagocytes that can clear infections.

TABLE 38

Induction of MCP-1 in RAW 264.7 cells and whole human blood. RAW 264.7 mouse macrophage cells or whole human blood were stimulated with increasing concentrations of LL-37 for 4 hr. The human blood samples were centrifuged and the serum was removed and tested for MCP-1 by ELISA along with the supernatants from the RAW 264.7 cells. The RAW cell data presented in the mean of three or more experiments ± standard error and the human blood data represents the mean ± standard error from three separate donors.

| Peptide, SEQ ID NO: 1 | Monocyte chemoattractant protein (MCP)-1 (pg/ml)* | |
| --- | --- | --- |
| (µg/ml) | RAW cells | Whole blood |
| 0 | 135.3 ± 16.3 | 112.7 ± 43.3 |
| 10 | 165.7 ± 18.2 | 239.3 ± 113.3 |
| 50 | 367 ± 11.5 | 371 ± 105 |
| 100 | 571 ± 17.4 | 596 ± 248.1 |

TABLE 39

Induction of IL-8 in A549 cells and whole human blood. A549 cells or whole human blood were stimulated with increasing concentrations of peptide for 24 and 4 hr respectively. The human blood samples were centrifuged and the serum was removed and tested for IL-8 by ELISA along with the supernatants from the A549 cells. The A549 cell data presented is the mean of three or more experiments ± standard error and the human blood data represents the mean ± standard error from three separate donors.

| Peptide, SEQ ID NO: 1 | IL-8 (pg/ml) | |
| --- | --- | --- |
| (µg/ml) | A549 cells | Whole blood |
| 0 | 172 ± 29.1 | 660.7 ± 126.6 |
| 1 | 206.7 ± 46.1 | |
| 10 | 283.3 ± 28.4 | 945.3 ± 279.9 |
| 20 | 392 ± 31.7 | |
| 50 | 542.3 ± 66.2 | 1160.3 ± 192.4 |
| 100 | 1175.3 ± 188.3 | |

TABLE 40

Induction of IL-8 in A549 cells by Cationic peptides. A549 human epithelial cells were stimulated with 10 µg of peptide for 24 hr. The supernatant was removed and tested for IL-8 by ELISA.

| Peptide (10 ug/ml) | IL-8 (ng/ml) |
| --- | --- |
| No peptide | 0.164 |
| LPS, no peptide | 0.26 |
| SEQ ID NO: 1 | 0.278 |
| SEQ ID NO: 6 | 0.181 |
| SEQ ID NO: 7 | 0.161 |
| SEQ ID NO: 9 | 0.21 |
| SEQ ID NO: 10 | 0.297 |
| SEQ ID NO: 13 | 0.293 |
| SEQ ID NO: 14 | 0.148 |
| SEQ ID NO: 16 | 0.236 |
| SEQ ID NO: 17 | 0.15 |
| SEQ ID NO: 19 | 0.161 |
| SEQ ID NO: 20 | 0.151 |
| SEQ ID NO: 21 | 0.275 |
| SEQ ID NO: 22 | 0.314 |
| SEQ ID NO: 23 | 0.284 |
| SEQ ID NO: 24 | 0.139 |
| SEQ ID NO: 26 | 0.201 |
| SEQ ID NO: 27 | 0.346 |
| SEQ ID NO: 28 | 0.192 |
| SEQ ID NO: 29 | 0.188 |
| SEQ ID NO: 30 | 0.284 |
| SEQ ID NO: 31 | 0.168 |
| SEQ ID NO: 33 | 0.328 |
| SEQ ID NO: 34 | 0.315 |
| SEQ ID NO: 35 | 0.301 |
| SEQ ID NO: 36 | 0.166 |
| SEQ ID NO: 37 | 0.269 |
| SEQ ID NO: 38 | 0.171 |
| SEQ ID NO: 40 | 0.478 |
| SEQ ID NO: 41 | 0.371 |
| SEQ ID NO: 42 | 0.422 |
| SEQ ID NO: 43 | 0.552 |
| SEQ ID NO: 44 | 0.265 |
| SEQ ID NO: 45 | 0.266 |
| SEQ ID NO: 47 | 0.383 |
| SEQ ID NO: 48 | 0.262 |
| SEQ ID NO: 49 | 0.301 |
| SEQ ID NO: 50 | 0.141 |
| SEQ ID NO: 51 | 0.255 |
| SEQ ID NO: 52 | 0.207 |
| SEQ ID NO: 53 | 0.377 |
| SEQ ID NO: 54 | 0.133 |

TABLE 41

Induction by Peptide of IL-8 in human blood.
Whole human blood was stimulated with increasing
concentrations of peptide for 4 hr. The human blood samples
were centrifuged and the serum was removed and tested
for IL-8 by ELISA. The data shown is the average 2 donors.

| SEQ ID NO: 3 (µg/ml) | IL-8 (pg/ml) |
|---|---|
| 0 | 85 |
| 10 | 70 |
| 100 | 323 |

TABLE 42

Induction of IL-8 in HBE cells.
Increasing concentrations of the peptide were
incubated with HBE cells for 8 h, the supernantant
removed and tested for IL-8. The data is presented as
the mean of three or more experiments ± standard error.

| SEQ ID NO: 2 (µg/ml) | IL-8 (pg/ml) |
|---|---|
| 0 | 552 ± 90 |
| 0.1 | 670 ± 155 |
| 1 | 712 ± 205 |
| 10 | 941 ± 15 |
| 50 | 1490 ± 715 |

TABLE 43

Induction of IL-8 in undifferentiated THP-1 cells.
The human monocyte THP-1 cells were incubated
with indicated concentrations of peptide for 8 hr.
The supernatant was removed and tested for IL-8 by ELISA.

| SEQ ID NO: 3 (µg/ml) | IL-8 (pg/ml) |
|---|---|
| 0 | 10.6 |
| 10 | 17.2 |
| 50 | 123.7 |

TABLE 44

Induction of MCP-1 by Peptide, SEQ ID NO: 1 in mouse airway.
BALB/c mice were anaesthetised with avertin and
given intratracheal installation of peptide or water or
no installation (no treatment). The mice were monitored
for 4 hours, anaesthetised and the BAL fluid was
isolated and analyzed for MCP-1 and TNF-α
concentrations by ELISA. The data shown is the mean
of 4 or 5 mice for each condition ± standard error.

| Condition | MCP-1 (pg/ml) | TNF-α (pg/ml) |
|---|---|---|
| Water | 16.5 ± 5 | 664 ± 107 |
| peptide | 111 ± 30 | 734 ± 210 |
| Avertin | 6.5 ± 0.5 | 393 ± 129 |

TABLE 45

Lack of Significant TNF-α induction by the Cationic
Peptides. RAW 264.7 macrophage cells were
incubated with indicated peptides (40 µg/ml)
for 6 hours. The supernatant was collected
and tested for levels of TNF-α by ELISA.
The data is presented as the mean of three or
more experiments ± standard error.

| Peptide Treatment | TNF-α (pg/ml) |
|---|---|
| Media background | 56 ± 8 |
| LPS treatment, No peptide | 15207 ± 186 |
| SEQ ID NO: 1 | 274 ± 15 |
| SEQ ID NO: 5 | 223 ± 45 |
| SEQ ID NO: 6 | 297 ± 32 |
| SEQ ID NO: 7 | 270 ± 42 |
| SEQ ID NO: 8 | 166 ± 23 |
| SEQ ID NO: 9 | 171 ± 33 |
| SEQ ID NO: 10 | 288 ± 30 |
| SEQ ID NO: 12 | 299 ± 65 |
| SEQ ID NO: 13 | 216 ± 42 |
| SEQ ID NO: 14 | 226 ± 41 |
| SEQ ID NO: 15 | 346 ± 41 |
| SEQ ID NO: 16 | 341 ± 68 |
| SEQ ID NO: 17 | 249 ± 49 |
| SEQ ID NO: 19 | 397 ± 86 |
| SEQ ID NO: 20 | 285 ± 56 |
| SEQ ID NO: 21 | 263 ± 8 |
| SEQ ID NO: 22 | 195 ± 42 |
| SEQ ID NO: 23 | 254 ± 58 |
| SEQ ID NO: 24 | 231 ± 32 |
| SEQ ID NO: 26 | 281 ± 34 |
| SEQ ID NO: 27 | 203 ± 42 |
| SEQ ID NO: 28 | 192 ± 26 |
| SEQ ID NO: 29 | 242 ± 40 |
| SEQ ID NO: 31 | 307 ± 71 |
| SEQ ID NO: 33 | 196 ± 42 |
| SEQ ID NO: 34 | 204 ± 51 |
| SEQ ID NO: 35 | 274 ± 76 |
| SEQ ID NO: 37 | 323 ± 41 |
| SEQ ID NO: 38 | 199 ± 38 |
| SEQ ID NO: 43 | 947 ± 197 |
| SEQ ID NO: 44 | 441 ± 145 |
| SEQ ID NO: 45 | 398 ± 90 |
| SEQ ID NO: 48 | 253 ± 33 |
| SEQ ID NO: 49 | 324 ± 38 |
| SEQ ID NO: 50 | 311 ± 144 |
| SEQ ID NO: 53 | 263 ± 40 |
| SEQ ID NO: 54 | 346 ± 86 |

EXAMPLE 6

Cationic Peptides Increase Surface Expression of Chemokine Receptors

To analyze cell surface expression of IL-8RB, CXCR-4, CCR2, and LFA-1, RAW macrophage cells were stained with 10 µg/ml of the appropriate primary antibody (Santa Cruz Biotechnology) followed by FITC-conjugated goat anti-rabbit IgG [IL-8RB and CXCR-4 (Jackson ImmunoResearch Laboratories, West Grove, Pa.)] or FITC-conjugated donkey anti-goat IgG (Santa Cruz). The cells were analyzed using a FACscan, counting 10,000 events and gating on forward and side scatter to exclude cell debris.

The polynucleotide array data suggested that some peptides up-regulate the expression of the chemokine receptors IL-8RB, CXCR-4 and CCR2 by 10, 4 and 1.4 fold above unstimulated cells respectively. To confirm the polynucleotide array data, the surface expression was examined by flow cytometry of these receptors on RAW cells stimulated with peptide for 4 hr. When 50 µg/ml of peptide was incubated with RAW cells for 4 hr, IL-8RB was upregulated an average of 2.4-fold above unstimulated cells, CXCR-4 was up-regulated an average of 1.6-fold above unstimulated cells and CCR2 was up-regulated 1.8-fold above unstimulated cells (Table 46). As a control CEMA was demonstrated to cause similar up-regulation. Bac2A was the only peptide to show significant up-regulation of LFA-1 (3.8 fold higher than control cells).

TABLE 46

Increased surface expression of CXCR-4, IL-8RB and CCR2 in response to peptides. RAW macrophage cells were stimulated with peptide for 4 hr. The cells were washed and stained with the appropriate primary and FITC-labeled secondary antibodies. The data shown represents the average (fold change of RAW cells stimulated with peptide from media) ± standard error.

| Peptide | Concentration (µg/ml) | Fold Increase in Protein Expression | | |
|---|---|---|---|---|
| | | IL-8RB | CXCR-4 | CCR2 |
| SEQ ID NO: 1 | 10 | 1.0 | 1.0 | 1.0 |
| SEQ ID NO: 1 | 50 | 1.3 ± 0.05 | 1.3 ± 0.03 | 1.3 ± 0.03 |
| SEQ ID NO: 1 | 100 | 2.4 ± 0.6 | 1.6 ± 0.23 | 1.8 ± 0.15 |
| SEQ ID NO: 3 | 100 | 2.0 ± 0.6 | Not Done | 4.5 |
| CEMA | 50 | 1.6 ± 0.1 | 1.5 ± 0.2 | 1.5 ± 0.15 |
| | 100 | 3.6 ± 0.8 | Not Done | 4.7 ± 1.1 |

EXAMPLE 7

Phosphorylation of Map Kinases by Cationic Peptides

The cells were seeded at $2.5 \times 10^5$-$5 \times 10^5$ cells/ml and left overnight. They were washed once in media, serum starved in the morning (serum free media–4 hrs). The media was removed and replaced with PBS, then sat at 37° C. for 15 minutes and then brought to room temp for 15 minutes. Peptide was added (concentrations 0.1 µg/ml-50 µg/ml) or $H_2O$ and incubated 10 min. The PBS was very quickly removed and replaced with ice-cold radioimmunoprecipitation (RIPA) buffer with inhibitors (NaF, B-glycerophosphate, MOL, Vanadate, PMSF, Leupeptin Aprotinin). The plates were shaken on ice for 10-15 min or until the cells were lysed and the lysates collected. The procedure for THP-1 cells was slightly different; more cells ($2 \times 10^6$) were used. They were serum starved overnight, and to stop the reaction 1 ml of ice-cold PBS was added then they sat on ice 5-10 min, were spun down then resuspended in RIPA. Protein concentrations were determined using a protein assay (Pierce, Rockford, Ill.). Cell lysates (20 µg of protein) were separated by SDS-PAGE and transferred to nitrocellulose filters. The filters were blocked for 1 h with 10 mM Tris-HCl, pH 7.5, 150 mM NaCl (TBS)/5% skim milk powder and then incubated overnight in the cold with primary antibody in TBS/0.05% Tween 20. After washing for 30 min with TBS/0.05% Tween 20, the filters were incubated for 1 h at room temperature with 1 µg/ml secondary antibody in TBS. The filters were washed for 30 min with TBS/0.05% Tween 20 and then incubated 1 h at room temperature with horseradish peroxidase-conjugated sheep anti-mouse IgG (1:10,000 in TBS/0.05% Tween 20). After washing the filters for 30 min with TBS/0.1% Tween 20, immunoreactive bands were visualized by enhanced chemiluminescence (ECL) detection. For experiments with peripheral blood mononuclear cells: The peripheral blood (50-100 ml) was collected from all subjects. Mononuclear cells were isolated from the peripheral blood by density gradient centrifugation on Ficoll-Hypaque. Interphase cells (mononuclear cells) were recovered, washed and then resuspended in recommended primary medium for cell culture (RPMI-1640) with 10% fetal calf serum (FCS) and 1% L-glutamine. Cells were added to 6 well culture plates at $4 \times 10^6$ cells/well and were allowed to adhere at 37° C. in 5% $CO_2$ atmosphere for 1 hour. The supenatant medium and non-adherent cells were washed off and the appropriate media with peptide was added. The freshly harvested cells were consistently >99% viable as assessed by their ability to exclude trypan blue. After stimulation with peptide, lysates were collected by lysing the cells in RIPA buffer in the presence of various phosphatase- and kinase-inhibitors. Protein content was analyzed and approximately 30 µg of each sample was loaded in a 12% SDS-PAGE gel. The gels were blotted onto nitrocellulose, blocked for 1 hour with 5% skim milk powder in Tris buffered saline (TBS) with 1% Triton X 100. Phosphorylation was detected with phosphorylation-specific antibodies.

The results of peptide-induced phosphorylation are summarized in Table 46. SEQ ID NO: 2 was found to cause dose dependent phosphorylation of p38 and ERK1/2 in the mouse macrophage RAW cell line and the HBE cells. SEQ ID NO: 3 caused phosphorylation of MAP kinases in THP-1 human monocyte cell line and phosphorylation of ERK1/2 in the mouse RAW cell line.

TABLE 47

Phosphorylation of MAP kinases in response to peptides.

| Cell Line | Peptide | MAP kinase phosphorylated | |
|---|---|---|---|
| | | p38 | ERK1/2 |
| RAW 264.7 | SEQ ID NO: 3 | – | + |
| | SEQ ID NO: 2 | + | + |
| HBE | SEQ ID NO: 3 | | + |
| | SEQ ID NO: 2 | + | + |
| THP-1 | SEQ ID NO: 3 | + | + |
| | SEQ ID NO: 2 | | |

TABLE 48

Peptide Phosphorylation of MAP kinases in human blood monocytes. SEQ ID NO: 1 at 50 µg/ml) was used to promote phosphorylation.

| p38 phosphorylation | | ERK1/2 phosphorylation | |
|---|---|---|---|
| 15 minutes | 60 minutes | 15 minutes | 60 minutes |
| + | – | + | + |

EXAMPLE 8

Cationic Peptides Protect Against Bacterial Infection by Enhancing the Immune Response BALB/c mice were given $1 \times 10^5$ Salmonella and cationic peptide (200 µg) by intraperitoneal injection. The mice were monitored for 24 hours at which point they were euthanized, the spleen removed, homogenized and resuspended in PBS and plated on Luria Broth agar plates with Kanamycin (50 µg/ml). The plates were incubated overnight at 37° C. and counted for viable bacteria (Table 49 and 50). CD-1 mice were given $1 \times 10^8$ *S. aureus* in 5% porcine mucin and cationic peptide (200 µg) by intraperitoneal injection (Table 51). The mice were monitored for 3 days at which point they were euthanized, blood removed and plated for viable counts. CD-1 male mice were given $5.8 \times 10^6$ CFU EHEC bacteria and cationic peptide (200 µg) by intraperitoneal (IP) injection and monitored for 3 days (Table 52). In each of these animal models a subset of the peptides demonstrated protection against infections. The most protective peptides in the Salmonella model demonstrated an ability to induce a common subset of genes in epithelial cells (Table 53) when comparing the protection assay results in Tables 50 and 51 to the gene expression results in Tables 31-37. This clearly indicates that there is a pattern of gene expression that is consistent with the ability of a peptide to demonstrate protection. Many of the cationic peptides were shown not to be directly antimicrobial as tested by the Minimum Inhibitory Concentration (MIC) assay (Table 54). This demonstrates that the ability of peptides to protect against infection relies on the ability of the peptide to stimulate host innate immunity rather than on direct antimicrobial activity.

TABLE 49

Effect of Cationic Peptides on Salmonella Infection in BALB/c mice. The BALB/c mice were injected IP with Salmonella and Peptide, and 24 h later the animals were euthanized, the spleen removed, homogenized, diluted in PBS and plate counts were done to determine bacteria viability

| Peptide Treatment | Viable Bacteria in the Spleen (CFU/ml) | Statistical Significance (p value) |
|---|---|---|
| Control | $2.70 \pm 0.84 \times 10^5$ | |
| SEQ ID NO: 1 | $1.50 \pm 0.26 \times 10^5$ | 0.12 |
| SEQ ID NO: 6 | $2.57 \pm 0.72 \times 10^4$ | 0.03 |
| SEQ ID NO: 13 | $3.80 \pm 0.97 \times 10^4$ | 0.04 |
| SEQ ID NO: 17 | $4.79 \pm 1.27 \times 10^4$ | 0.04 |
| SEQ ID NO: 27 | $1.01 \pm 0.26 \times 10^5$ | 0.06 |

TABLE 50

Effect of Cationic Peptides on Salmonella Infection in BALB/c mice. The BALB/c mice were injected intraperitoneally with Salmonella and Peptide, and 24 h later the animals were euthanized, the spleen removed, homogenized, diluted in PBS and plate counts were done to determine bacteria viability.

| Peptide Treatment | Viable Bacteria in the Spleen (CFU/ml) |
|---|---|
| Control | $1.88 \pm 0.16 \times 10^4$ |
| SEQ ID NO: 48 | $1.98 \pm 0.18 \times 10^4$ |

TABLE 50-continued

Effect of Cationic Peptides on Salmonella Infection in BALB/c mice. The BALB/c mice were injected intraperitoneally with Salmonella and Peptide, and 24 h later the animals were euthanized, the spleen removed, homogenized, diluted in PBS and plate counts were done to determine bacteria viability.

| Peptide Treatment | Viable Bacteria in the Spleen (CFU/ml) |
|---|---|
| SEQ ID NO: 26 | $7.1 \pm 1.37 \times 10^4$ |
| SEQ ID NO: 30 | $5.79 \pm 0.43 \times 10^3$ |
| SEQ ID NO: 37 | $1.57 \pm 0.44 \times 10^4$ |
| SEQ ID NO: 5 | $2.75 \pm 0.59 \times 10^4$ |
| SEQ ID NO: 7 | $5.4 \pm 0.28 \times 10^3$ |
| SEQ ID NO: 9 | $1.23 \pm 0.87 \times 10^4$ |
| SEQ ID NO: 14 | $2.11 \pm 0.23 \times 10^3$ |
| SEQ ID NO: 20 | $2.78 \pm 0.22 \times 10^4$ |
| SEQ ID NO: 23 | $6.16 \pm 0.32 \times 10^4$ |

TABLE 51

Effect of Cationic Peptides in a Murine *S. aureus* infection model. CD-1 mice were given $1 \times 10^8$ bacteria in 5% porcine mucin via intraperitoneal (IP) injection. Cationic peptide (200 µg) was given via a separate IP injection. The mice were monitored for 3 days at which point they were euthanized, blood removed and plated for viable counts. The following peptides were not effective in controlling *S. aureus* infection: SEQ ID NO: 48, SEQ ID NO: 26

| Treatment | CFU/ml (blood) | # Mice Survived (3 days)/ Total mice in group |
|---|---|---|
| No Peptide | $7.61 \pm 1.7 \times 10^3$ | 6/8 |
| SEQ ID NO: 1 | 0 | 4/4 |
| SEQ ID NO: 27 | $2.25 \pm 0.1 \times 10^2$ | 3/4 |
| SEQ ID NO: 30 | $1.29 \pm 0.04 \times 10^2$ | 4/4 |
| SEQ ID NO: 37 | $9.65 \pm 0.41 \times 10^2$ | 4/4 |
| SEQ ID NO: 5 | $3.28 \pm 1.7 \times 10^3$ | 4/4 |
| SEQ ID NO: 6 | $1.98 \pm 0.05 \times 10^2$ | 3/4 |
| SEQ ID NO: 7 | $3.8 \pm 0.24 \times 10^3$ | 4/4 |
| SEQ ID NO: 9 | $2.97 \pm 0.25 \times 10^2$ | 4/4 |
| SEQ ID NO: 13 | $4.83 \pm 0.92 \times 10^3$ | 3/4 |
| SEQ ID NO: 17 | $9.6 \pm 0.41 \times 10^2$ | 4/4 |
| SEQ ID NO: 20 | $3.41 \pm 1.6 \times 10^3$ | 4/4 |
| SEQ ID NO: 23 | $4.39 \pm 2.0 \times 10^3$ | 4/4 |

TABLE 52

Effect of Peptide in a Murine EHEC infection model. CD-1 male mice (5 weeks old) were given $5.8 \times 10^6$ CFU EHEC bacteria via intraperitoneal (IP) injection. Cationic peptide (200 µg) was given via a separate IP injection. The mice were monitored for 3 days.

| Treatment | Peptide | Survival (%) |
|---|---|---|
| control | none | 25 |
| SEQ ID NO: 23 | 200 µg | 100 |

TABLE 53

Up-regulation of patterns of gene expression in A549 epithelial cells induced by peptides that are active in vivo.

The peptides SEQ ID NO: 30, SEQ ID NO: 7 and SEQ ID NO: 13 at concentrations of 50 μg/ml were each shown to increase the expression of a pattern of genes after 4 h treatment. Peptide was incubated with the human A549 epithelial cells for 4 h and the RNA was isolated, converted into labelled cDNA probes and hybridised to Human Operon arrays (PRHU04). The intensity of polynucleotides in control, unstimulated cells are shown in the second columns for labelling of cDNA (average of Cy3 and Cy5). The Fold Up regulation column refers to the intensity of polynucleotide expression in peptide-simulated cells divided by the intensity of unstimulated cells. The SEQ ID NO: 37 peptide was included as a negative control that was not active in the murine infection models.

| Target (Accession number) | Unstimulated Cell Intensity | Fold Up regulation of Gene Expression relative to Untreated Cells ||||
|---|---|---|---|---|---|
| | | SEQ ID NO: 30 | SEQ ID NO: 7 | SEQ ID NO: 13 | SEQ ID NO: 37 |
| Zinc finger protein (AF061261) | 13 | 2.6 | 9.4 | 9.4 | 1.0 |
| Cell cycle gene (S70622) | 1.62 | 8.5 | 3.2 | 3.2 | 0.7 |
| IL-10 Receptor (U00672) | 0.2 | 2.6 | 9 | 4.3 | 0.5 |
| Transferase (AF038664) | 0.09 | 12.3 | 9.7 | 9.7 | 0.1 |
| Homeobox protein (AC004774) | 0.38 | 3.2 | 2.5 | 2.5 | 1.7 |
| Forkhead protein (AF042832) | 0.17 | 14.1 | 3.5 | 3.5 | 0.9 |
| Unknown (AL096803) | 0.12 | 4.8 | 4.3 | 4.3 | 0.6 |
| KIAA0284 Protein (AB006622) | 0.47 | 3.4 | 2.1 | 2.1 | 1.3 |
| Hypothetical Protein (AL022393) | 0.12 | 4.4 | 4.0 | 4.0 | 0.4 |
| Receptor (AF112461) | 0.16 | 2.4 | 10.0 | 10.0 | 1.9 |
| Hypothetical Protein (AK002104) | 0.51 | 4.7 | 2.6 | 2.6 | 1.0 |
| Protein (AL050261) | 0.26 | 3.3 | 2.8 | 2.8 | 1.0 |
| Polypeptide (AF105424) | 0.26 | 2.5 | 5.3 | 5.3 | 1.0 |
| SPR1 protein (AB031480) | 0.73 | 3.0 | 2.7 | 2.7 | 1.3 |
| Dehydrogenase (D17793) | 4.38 | 2.3 | 2.2 | 2.2 | 0.9 |
| Transferase (M63509) | 0.55 | 2.7 | 2.1 | 2.1 | 1.0 |
| Peroxisome factor (AB013818) | 0.37 | 3.4 | 2.9 | 2.9 | 1.4 |

TABLE 54

Most cationic peptides studied here and especially the cationic peptides effective in infection models are not significantly antimicrobial. A dilution series of peptide was incubated with the indicated bacteria overnight in a 96-well plate. The lowest concentration of peptide that killed the bacteria was used as the MIC. The symbol > indicates the MIC is too large to measure. An MIC of 8 μg/ml or less was considered clinically meaningful activity. Abbreviations: E. coli, Escherichia coli; S. aureus, Staphylococcus aureus; P. aerug, Pseudomonas aeruginosa; S. Typhim, Salmonella enteritidis ssp. typhimurium; C. rhod, Citobacter rhodensis; EHEC, Enterohaemorrhagic E. coli.

| Peptide | MIC (μg/ml) |||||| 
|---|---|---|---|---|---|---|
| | E. coli | S. aureus | P. aerug. | S. typhim. | C. rhod. | EHEC |
| Polymyxin | 0.25 | 16 | 0.25 | 0.5 | 0.25 | 0.5 |
| Gentamicin | 0.25 | 0.25 | 0.25 | 0.25 | 0.25 | 0.5 |
| SEQ ID NO: 1 | 32 | > | 96 | 64 | 8 | 4 |
| SEQ ID NO: 5 | 128 | > | > | > | 64 | 64 |
| SEQ ID NO: 6 | 128 | > | > | 128 | 64 | 64 |
| SEQ ID NO: 7 | > | > | > | > | > | > |
| SEQ ID NO: 8 | > | > | > | > | > | > |
| SEQ ID NO: 9 | > | > | > | > | > | > |
| SEQ ID NO: 10 | > | > | > | > | > | 64 |
| SEQ ID NO: 12 | > | > | > | > | > | > |
| SEQ ID NO: 13 | > | > | > | > | > | > |
| SEQ ID NO: 14 | > | > | > | > | > | > |
| SEQ ID NO: 15 | 128 | > | > | > | 128 | 64 |
| SEQ ID NO: 16 | > | > | > | > | > | > |
| SEQ ID NO: 17 | > | > | > | > | > | > |
| SEQ ID NO: 19 | 8 | 16 | 16 | 64 | 4 | 4 |
| SEQ ID NO: 2 | 4 | 16 | 32 | 16 | 64 | |
| SEQ ID NO: 20 | 8 | 8 | 8 | 8 | 16 | 8 |
| SEQ ID NO: 21 | 64 | 64 | 96 | 64 | 32 | 32 |
| SEQ ID NO: 22 | 8 | 12 | 24 | 8 | 4 | 4 |
| SEQ ID NO: 23 | 4 | 8 | 8 | 16 | 4 | 4 |
| SEQ ID NO: 24 | 16 | 16 | 4 | 16 | 16 | 4 |
| SEQ ID NO: 26 | 0.5 | 32 | 64 | 2 | 2 | 0.5 |
| SEQ ID NO: 27 | 8 | 64 | 64 | 16 | 2 | 4 |
| SEQ ID NO: 28 | > | > | > | 64 | 64 | 128 |
| SEQ ID NO: 29 | 2 | > | > | 16 | 32 | 4 |
| SEQ ID NO: 30 | 16 | > | 128 | 16 | 16 | 4 |
| SEQ ID NO: 31 | > | > | 128 | > | > | 64 |
| SEQ ID NO: 33 | 16 | 32 | > | 16 | 64 | 8 |
| SEQ ID NO: 34 | 8 | > | > | 32 | 64 | 8 |
| SEQ ID NO: 35 | 4 | 128 | 64 | 8 | 8 | 4 |
| SEQ ID NO: 36 | 32 | > | > | 32 | 32 | 16 |
| SEQ ID NO: 37 | > | > | > | > | > | > |
| SEQ ID NO: 38 | 0.5 | 32 | 64 | 4 | 8 | 4 |
| SEQ ID NO: 40 | 4 | 32 | 8 | 4 | 4 | 2 |
| SEQ ID NO: 41 | 4 | 64 | 8 | 8 | 2 | 2 |
| SEQ ID NO: 42 | 1.5 | 64 | 4 | 2 | 2 | 1 |
| SEQ ID NO: 43 | 8 | 128 | 16 | 16 | 8 | 4 |

TABLE 54-continued

Most cationic peptides studied here and especially the cationic peptides effective in infection models are not significantly antimicrobial. A dilution series of peptide was incubated with the indicated bacteria overnight in a 96-well plate. The lowest concentration of peptide that killed the bacteria was used as the MIC. The symbol > indicates the MIC is too large to measure. An MIC of 8 μg/ml or less was considered clinically meaningful activity. Abbreviations: *E. coli, Escherichia coli*; *S. aureus, Staphylococcus aureus*; *P. aerug, Pseudomonas aeruginosa*; *S. Typhim, Salmonella enteritidis* ssp. typhimurium; *C. rhod, Citobacter rhodensis*; EHEC, Enterohaemorrhagic *E. coli*.

| Peptide | MIC (μg/ml) | | | | | |
|---|---|---|---|---|---|---|
| | E. coli | S. aureus | P. aerug. | S. typhim. | C. rhod. | EHEC |
| SEQ ID NO: 44 | 8 | > | 128 | 128 | 64 | 64 |
| SEQ ID NO: 45 | 8 | > | 128 | 128 | 16 | 16 |
| SEQ ID NO: 47 | 4 | > | 16 | 16 | 4 | 4 |
| SEQ ID NO: 48 | 16 | > | 128 | 16 | 1 | 2 |
| SEQ ID NO: 49 | 4 | > | 16 | 8 | 4 | 4 |
| SEQ ID NO: 50 | 8 | > | 16 | 16 | 16 | 8 |
| SEQ ID NO: 51 | 4 | > | 8 | 32 | 4 | 8 |
| SEQ ID NO: 52 | 8 | > | 32 | 8 | 2 | 2 |
| SEQ ID NO: 53 | 4 | > | 8 | 8 | 16 | 8 |
| SEQ ID NO: 54 | 64 | > | 16 | 64 | 16 | 32 |

EXAMPLE 9

Use of Polynucleotides Induced by Bacterial Signalling Molecules in Diagnostic/Screening

*S. typhimurium* LPS and *E. coli* O111:B4 LPS were purchased from Sigma Chemical Co. (St. Louis, Mo.). LTA (Sigma) from *S. aureus*, was resuspended in endotoxin free water (Sigma). The Limulus amoebocyte lysate assay (Sigma) was performed on LTA preparations to confirm that lots were not significantly contaminated by endotoxin (i.e. <1 ng/ml, a concentration that did not cause significant cytokine production in the RAW cell assay). The CpG oligodeoxynucleotides were synthesized with an Applied Biosystems Inc., Model 392 DNA/RNA Synthesizer, Mississauga, ON., then purified and resuspended in endotoxin-free water (Sigma). The following sequences were used CpG: 5'-TCAT-GACGTTCCTGACGTT-3' (SEQ ID NO: 57) and nonCpG: 5'-TTCAGGACTTTCCTCAGGTT-3' (SEQ ID NO: 58). The nonCpG oligo was tested for its ability to stimulate production of cytokines and was found to cause no significant production of TNF-α or IL-6 and therefore was considered as a negative control. RNA was isolated from RAW 264.7 cells that had been incubated for 4h with medium alone, 100 ng/ml *S. typhimurium* LPS, 1 μg/ml *S. aureus* LTA, or 1 μM CpG (concentrations that led to optimal induction of tumor necrosis factor (TNF-α) in RAW cells). The RNA was used to polynucleotiderate cDNA probes that were hybridized to Clontech Atlas polynucleotide array filters, as described above. The hybridization of the cDNA probes to each immobilized DNA was visualized by autoradiography and quantified using a phosphorimager. Results from at least 2 to 3 independent experiments are summarized in Tables 55-59. It was found that LPS treatment of RAW 264.7 cells resulted in increased expression of more than 60 polynucleotides including polynucleotides encoding inflammatory proteins such as IL-1 β, inducible nitric oxide synthase (iNOS), MIP-1α, MIP-1β, MIP-2α, CD40, and a variety of transcription factors. When the changes in polynucleotide expression induced by LPS, LTA, and CpG DNA were compared, it was found that all three of these bacterial products increased the expression of pro-inflammatory polynucleotides such as iNOS, MIP-1α, MIP-2α, IL-1β, IL-15, TNFR1 and NF-κB to a similar extent (Table 57). Table 57 describes 19 polynucleotides that were up-regulated by the bacterial products to similar extents in that their stimulation ratios differed by less than 1.5 fold between the three bacterial products. There were also several polynucleotides that were down-regulated by LPS, LTA and CpG to a similar extent. It was also found that there were a number of polynucleotides that were differentially regulated in response to the three bacterial products (Table 58), which includes many of these polynucleotides that differed in expression levels by more than 1.5 fold between one or more bacterial products). LTA treatment differentially influenced expression of the largest subset of polynucleotides compared to LPS or CpG, including hyperstimulation of expression of Jun-D, Jun-B, Elk-1 and cyclins G2 and A1. There were only a few polynucleotides whose expression was altered more by LPS or CpG treatment. Polynucleotides that had preferentially increased expression due to LPS treatment compared to LTA or CpG treatment included the cAMP response element DNA-binding protein 1 (CRE-BPl), interferon inducible protein 1 and CACCC Box-binding protein BKLF. Polynucleotides that had preferentially increased expression after CpG treatment compared to LPS or LTA treatment included leukemia inhibitory factor (LIF) and protease nexin 1 (PN-1). These results indicate that although LPS, LTA, and CpG DNA stimulate largely overlapping polynucleotide expression responses, they also exhibit differential abilities to regulate certain subsets of polynucleotides.

The other polynucleotide arrays used are the Human Operon arrays (identification number for the genome is PRHU04-S1), which consist of about 14,000 human oligos spotted in duplicate. Probes were prepared from 5 μg of total RNA and labeled with Cy3 or Cy5 labeled dUTP. In these experiments, A549 epithelial cells were plated in 100 mm tissue culture dishes at $2.5 \times 10^6$ cells/dish, incubated overnight and then stimulated with 100 ng/ml *E. coli* O111:B4 LPS for 4 h. Total RNA was isolated using RNAqueous (Ambion). DNA contamination was removed with DNA-free kit (Ambion). The probes prepared from total RNA were purified and hybridized to printed glass slides overnight at 42° C. and washed. After washing, the image was captured using a Perkin Elmer array scanner. The image processing software (Imapolynucleotide 5.0, Marina Del Rey, Calif.) determines the spot mean intensity, median intensities, and background intensities. An "in house" program was used to remove background. The program calculates the bottom 10% intensity for each subgrid and subtracts this for each grid. Analysis was performed with Polynucleotidespring software (Redwood City, Calif.). The intensities for each spot were normalized by taking the median spot intensity value from the population of spot values within a slide and comparing this value to the values of all slides in the experiment. The relative changes seen with cells treated with LPS compared to control cells can be found in the Tables below. A number of previously unreported changes that would be useful in diagnosing infection are described in Table 60.

To confirm and assess the functional significance of these changes, the levels of selected mRNAs and proteins were assessed and quantified by densitometry. Northern blots using a CD 14, vimentin, and tristetraprolin-specific probe confirmed similar expression after stimulation with all 3 bacterial products (Table 60). Similarly measurement of the enzymatic activity of nitric oxide synthetase, iNOS, using Griess reagent to assess levels of the inflammatory mediator NO, demonstrated comparable levels of NO produced after 24 h, consistent with the similar up-regulation of iNOS expression (Table 59). Western blot analysis confirmed the preferential stimulation of leukaemia inhibitory factor (LIF, a member of the IL-6 family of cytokines) by CpG (Table 59). Other confirmatory experiments demonstrated that LPS up-regulated the expression of TNF-α and IL-6 as assessed by ELISA, and the up-regulated expression of MEP-2α, and IL-1β mRNA and down-regulation of DP-1 and cyclin D MRNA as assessed by Northern blot analysis. The analysis was expanded to a more clinically relevant ex vivo system, by examining the ability of the bacterial elements to stimulate pro-inflammatory cytokine production in whole human blood. It was found that E. coli LPS, S. typhimurium LPS, and S. aureus LTA all stimulated similar amounts of serum TNF-α, and IL-1β. CpG also stimulated production of these cytokines, albeit to much lower levels, confirming in part the cell line data.

TABLE 55

Polynucleotides Up-regulated by E. coli O111: B4 LPS in A549 Epithelial Cells.
E. coli O111: B4 LPS (100 ng/ml) increased the expression of many polynucleotides in A549 cells as studied by polynucleotide microarrays. LPS was incubated with the A549 cells for 4 h and the RNA was isolated. 5 μg total RNA was used to make Cy3/Cy5 labelled cDNA probes and hybridised onto Human Operon arrays (PRHU04). The intensity of unstimulated cells is shown in the second column of Table 55. The "Ratio: LPS/control" column refers to the intensity of polynucleotide expression in LPS simulated cells divided by in the intensity of unstimulated cells.

| Acession Number | Gene | Control: Media only Intensity | Ratio: LPS/control |
|---|---|---|---|
| D87451 | ring finger protein 10 | 715.8 | 183.7 |
| AF061261 | C3H-type zinc finger protein | 565.9 | 36.7 |
| D17793 | aldo-keto reductase family 1, member C3 | 220.1 | 35.9 |
| M14630 | prothymosin, alpha | 168.2 | 31.3 |
| AL049975 | Unknown | 145.6 | 62.3 |
| L04510 | ADP-ribosylation factor domain protein 1, 64 kD | 139.9 | 213.6 |
| U10991 | G2 protein | 101.7 | 170.3 |
| U39067 | eukaryotic translation initiation factor 3, subunit 2 | 61.0 | 15.9 |
| X03342 | ribosomal protein L32 | 52.6 | 10.5 |
| NM_004850 | Rho-associated, coiled-coil containing protein kinase 2 | 48.1 | 11.8 |
| AK000942 | Unknown | 46.9 | 8.4 |
| AB040057 | serine/threonine protein kinase MASK | 42.1 | 44.3 |
| AB020719 | KIAA0912 protein | 41.8 | 9.4 |
| AB007856 | FEM-1-like death receptor binding protein | 41.2 | 15.7 |
| J02783 | procollagen-proline, 2-oxoglutarate 4-dioxygenase | 36.1 | 14.1 |
| AL137376 | Unknown | 32.5 | 17.3 |
| AL137730 | Unknown | 29.4 | 11.9 |
| D25328 | phosphofructokinase, platelet | 27.3 | 8.5 |
| AF047470 | malate dehydrogenase 2, NAD | 25.2 | 8.2 |
| M86752 | stress-induced-phosphoprotein 1 | 22.9 | 5.9 |
| M90696 | cathepsin S | 19.6 | 6.8 |
| AK001143 | Unknown | 19.1 | 6.4 |
| AF038406 | NADH dehydrogenase | 17.7 | 71.5 |
| AK000315 | hypothetical protein FLJ20308 | 17.3 | 17.4 |
| M54915 | pim-1 oncogene | 16.0 | 11.4 |
| D29011 | proteasome subunit, beta type, 5 | 15.3 | 41.1 |
| AK000237 | membrane protein of cholinergic synaptic vesicles | 15.1 | 9.4 |
| AL034348 | Unknown | 15.1 | 15.8 |
| AL161991 | Unknown | 14.2 | 8.1 |
| AL049250 | Unknown | 12.7 | 5.6 |

TABLE 55-continued

Polynucleotides Up-regulated by E. coli O111: B4 LPS in A549 Epithelial Cells.
E. coli O111: B4 LPS (100 ng/ml) increased the expression of many polynucleotides in A549 cells as studied by polynucleotide microarrays. LPS was incubated with the A549 cells for 4 h and the RNA was isolated. 5 μg total RNA was used to make Cy3/Cy5 labelled cDNA probes and hybridised onto Human Operon arrays (PRHU04). The intensity of unstimulated cells is shown in the second column of Table 55. The "Ratio: LPS/control" column refers to the intensity of polynucleotide expression in LPS simulated cells divided by in the intensity of unstimulated cells.

| Acession Number | Gene | Control: Media only Intensity | Ratio: LPS/control |
|---|---|---|---|
| AL050361 | PTD017 protein | 12.6 | 13.0 |
| U74324 | RAB interacting factor | 12.3 | 5.2 |
| M22538 | NADH dehydrogenase | 12.3 | 7.6 |
| D87076 | KIAA0239 protein | 11.6 | 6.5 |
| NM_006327 | translocase of inner mitochondrial membrane 23 (yeast) homolog | 11.5 | 10.0 |
| AK001083 | Unknown | 11.1 | 8.6 |
| AJ001403 | mucin 5, subtype B, tracheobronchial | 10.8 | 53.4 |
| M64788 | RAP1, GTPase activating protein 1 | 10.7 | 7.6 |
| X06614 | retinoic acid receptor, alpha | 10.7 | 5.5 |
| U85611 | calcium and integrin binding protein | 10.3 | 8.1 |
| U23942 | cytochrome P450, 51 | 10.1 | 10.2 |
| AL031983 | Unknown | 9.7 | 302.8 |
| NM_007171 | protein-O-mannosyltransferase 1 | 9.5 | 6.5 |
| AK000403 | hypothetical protein FLJ20396 | 9.5 | 66.6 |
| NM_002950 | ribophorin I | 9.3 | 35.7 |
| L05515 | cAMP response element-binding protein CRE-BPa | 8.9 | 6.2 |
| X83368 | phosphoinositide-3-kinase, catalytic, gamma polypeptide | 8.7 | 27.1 |
| M30269 | nidogen (enactin) | 8.7 | 5.5 |
| M91083 | chromosome 11 open reading frame 13 | 8.2 | 6.6 |
| D29833 | salivary proline-rich protein | 7.7 | 5.8 |
| AB024536 | immunoglobulin superfamily containing leucine-rich repeat | 7.6 | 8.0 |
| U39400 | chromosome 11 open reading frame 4 | 7.4 | 7.3 |
| AF028789 | unc119 (C.elegans) homolog | 7.4 | 27.0 |
| NM_003144 | signal sequence receptor, alpha (translocon-associated protein alpha) | 7.3 | 5.9 |
| X52195 | arachidonate 5-lipoxygenase-activating protein | 7.3 | 13.1 |
| U43895 | human growth factor-regulated tyrosine kinase substrate | 6.9 | 6.9 |
| L25876 | cyclin-dependent kinase inhibitor 3 | 6.7 | 10.3 |
| L04490 | NADH dehydrogenase | 6.6 | 11.1 |
| Z18948 | S100 calcium-binding protein | 6.3 | 11.0 |
| D10522 | myristoylated alanine-rich protein kinase C substrate | 6.1 | 5.8 |
| NM_014442 | sialic acid binding Ig-like lectin 8 | 6.1 | 7.6 |
| U81375 | solute carrier family 29 | 6.0 | 6.4 |
| AF041410 | malignancy-associated protein | 5.9 | 5.3 |
| U24077 | killer cell immunoglobulin-like receptor | 5.8 | 14.4 |
| AL137614 | hypothetical protein | 4.8 | 6.8 |
| NM_002406 | mannosyl (alpha-1,3-)-glycoprotein beta-1,2-N-acetylglucosaminyltransferase | 4.7 | 5.3 |
| AB002348 | KIAA0350 protein | 4.7 | 7.6 |

TABLE 55-continued

Polynucleotides Up-regulated by *E. coli* O111: B4 LPS in A549 Epithelial Cells.

*E. coli* O111: B4 LPS (100 ng/ml) increased the expression of many polynucleotides in A549 cells as studied by polynucleotide microarrays. LPS was incubated with the A549 cells for 4 h and the RNA was isolated. 5 μg total RNA was used to make Cy3/Cy5 labelled cDNA probes and hybridised onto Human Operon arrays (PRHU04). The intensity of unstimulated cells is shown in the second column of Table 55. The "Ratio: LPS/control" column refers to the intensity of polynucleotide expression in LPS simulated cells divided by in the intensity of unstimulated cells.

| Acession Number | Gene | Control: Media only Intensity | Ratio: LPS/control |
|---|---|---|---|
| AF165217 | tropomodulin 4 (muscle) | 4.6 | 12.3 |
| Z14093 | branched chain keto acid dehydrogenase E1, alpha polypeptide | 4.6 | 5.4 |
| U82671 | caltractin | 3.8 | 44.5 |
| AL050136 | Unknown | 3.6 | 5.0 |
| NM_005135 | solute carrier family 12 | 3.6 | 5.0 |
| AK001961 | hypothetical protein FLJ11099 | 3.6 | 5.9 |
| AL034410 | Unknown | 3.2 | 21.3 |
| S74728 | antiquitin 1 | 3.1 | 9.2 |
| AL049714 | ribosomal protein L34 pseudogene 2 | 3.0 | 19.5 |
| NM_014075 | PRO0593 protein | 2.9 | 11.5 |
| AF189279 | phospholipase A2, group IIE | 2.8 | 37.8 |
| J03925 | integrin, alpha M | 2.7 | 9.9 |
| NM_012177 | F-box protein Fbx5 | 2.6 | 26.2 |
| NM_004519 | potassium voltage-gated channel, KQT-like subfamily, member 3 | 2.6 | 21.1 |
| M28825 | CD1A antigen, a polypeptide | 2.6 | 16.8 |
| X16940 | actin, gamma 2, smooth muscle, enteric | 2.4 | 11.8 |
| X03066 | major histocompatibility complex, class II, DO beta | 2.2 | 36.5 |
| AK001237 | hypothetical protein FLJ10375 | 2.1 | 18.4 |
| AB028971 | KIAA1048 protein | 2.0 | 9.4 |
| AL137665 | Unknown | 2.0 | 7.3 |

TABLE 56

Polynucleotides Down-regulated by *E. coli* O111: B4 LPS in A549 Epithelial Cells.

*E. coli* O111: B4 LPS (100 ng/ml) decreased the expression of many polynucleotides in A549 cells as studied by polynucleotide microarrays. LPS was incubated with the A549 cells for 4 h and the RNA was isolated. 5 μg total RNA was used to make Cy3/Cy5 labeled cDNA probes and hybridized onto Human Operon arrays (PRHU04). The intensity of unstimulated cells is shown in the second column of the Table. The "Ratio: LPS/control" column refers to the intensity of polynucleotide expression in LPS simulated cells divided by in the intensity of unstimulated cells.

| Accession Number | Gene | Control: Media only Intensity | Ratio: LPS/control |
|---|---|---|---|
| NM_017433 | myosin IIIA | 167.8 | 0.03 |
| X60484 | H4 histone family member E | 36.2 | 0.04 |
| X60483 | H4 histone family member D | 36.9 | 0.05 |
| AF151079 | hypothetical protein | 602.8 | 0.05 |
| M96843 | inhibitor of DNA binding 2, dominant negative helix-loop-helix protein | 30.7 | 0.05 |
| S79854 | deiodinase, iodothyronine, type III | 39.4 | 0.06 |
| AB018266 | matrin 3 | 15.7 | 0.08 |
| M33374 | NADH dehydrogenase | 107.8 | 0.09 |
| AF005220 | *Homo sapiens* mRNA for NUP98-HOXD13 fusion protein, partial cds | 105.2 | 0.09 |
| Z80783 | H2B histone family, member L | 20.5 | 0.10 |
| Z46261 | H3 histone family, member A | 9.7 | 0.12 |
| Z80780 | H2B histone family, member H | 35.3 | 0.12 |
| U33931 | erythrocyte membrane protein band 7.2 (stomatin) | 18.9 | 0.13 |
| M60750 | H2B histone family, member A | 35.8 | 0.14 |
| Z83738 | H2B histone family, member E | 19.3 | 0.15 |
| Y14690 | collagen, type V, alpha 2 | 7.5 | 0.15 |
| M30938 | X-ray repair complementing defective repair in Chinese hamster cells 5 | 11.3 | 0.16 |
| L36055 | eukaryotic translation initiation factor 4E binding protein 1 | 182.5 | 0.16 |
| Z80779 | H2B histone family, member G | 54.3 | 0.16 |
| AF226869 | 5(3)-deoxyribonucleotidase; RB-associated KRAB repressor | 7.1 | 0.18 |
| D50924 | KIAA0134 gene product | 91.0 | 0.18 |
| AL133415 | vimentin | 78.1 | 0.19 |
| AL050179 | tropomyosin 1 (alpha) | 41.6 | 0.19 |
| AJ005579 | RD element | 5.4 | 0.19 |
| M80899 | AHNAK nucleoprotein | 11.6 | 0.19 |
| NM_004873 | BCL2-associated athanogene 5 | 6.2 | 0.19 |
| X57138 | H2A histone family, member N | 58.3 | 0.20 |
| AF081281 | lysophospholipase I | 7.2 | 0.22 |
| U96759 | von Hippel-Lindau binding protein 1 | 6.6 | 0.22 |
| U85977 | Human ribosomal protein L12 pseudogene, partial cds | 342.6 | 0.22 |
| D13315 | glyoxalase I | 7.5 | 0.22 |
| AC003007 | Unknown | 218.2 | 0.22 |
| AB032980 | RU2S | 246.6 | 0.22 |
| U40282 | integrin-linked kinase | 10.1 | 0.22 |
| U81984 | endothelial PAS domain protein 1 | 4.7 | 0.23 |
| X91788 | chloride channel, nucleotide-sensitive, 1A | 9.6 | 0.23 |
| AF018081 | collagen, type XVIII, alpha 1 | 6.9 | 0.24 |
| L31881 | nuclear factor I/X (CCAAT-binding transcription factor) | 13.6 | 0.24 |
| X61123 | B-cell translocation gene 1, anti-proliferative | 5.3 | 0.24 |
| L32976 | mitogen-activated protein kinase kinase kinase 11 | 6.3 | 0.24 |
| M27749 | immunoglobulin lambda-like polypeptide 3 | 5.5 | 0.24 |
| X57128 | H3 histone family, member C | 9.0 | 0.25 |
| X80907 | phosphoinositide-3-kinase, regulatory subunit, polypeptide 2 | 5.8 | 0.25 |
| Z34282 | *H. sapiens* (MAR11) MUC5AC mRNA for mucin (partial) | 100.6 | 0.26 |
| X00089 | H2A histone family, member M | 4.7 | 0.26 |
| AL035252 | CD39-like 2 | 4.6 | 0.26 |
| X95289 | PERB11 family member in MHC class I region | 27.5 | 0.26 |

TABLE 56-continued

Polynucleotides Down-regulated by *E. coli* O111: B4 LPS in A549 Epithelial Cells.
*E. coli* O111: B4 LPS (100 ng/ml) decreased the expression of many polynucleotides in A549 cells as studied by polynucleotide microarrays. LPS was incubated with the A549 cells for 4 h and the RNA was isolated. 5 µg total RNA was used to make Cy3/Cy5 labeled cDNA probes and hybridized onto Human Operon arrays (PRHU04). The intensity of unstimulated cells is shown in the second column of the Table. The "Ratio: LPS/control" column refers to the intensity of polynucleotide expression in LPS simulated cells divided by in the intensity of unstimulated cells.

| Accession Number | Gene | Control: Media only Intensity | Ratio: LPS/control |
|---|---|---|---|
| AJ001340 | U3 snoRNP-associated 55-kDa protein | 4.0 | 0.26 |
| NM_014161 | HSPC071 protein | 10.6 | 0.27 |
| U60873 | Unknown | 6.4 | 0.27 |
| X91247 | thioredoxin reductase 1 | 84.4 | 0.27 |
| AK001284 | hypothetical protein FLJ10422 | 4.2 | 0.27 |
| U90840 | synovial sarcoma, X breakpoint 3 | 6.6 | 0.27 |
| X53777 | ribosomal protein L17 | 39.9 | 0.27 |
| AL035067 | Unknown | 10.0 | 0.28 |
| AL117665 | DKFZP586M1824 protein | 3.9 | 0.28 |
| L14561 | ATPase, Ca++ transporting, plasma membrane 1 | 5.3 | 0.28 |
| L19779 | H2A histone family, member O | 30.6 | 0.28 |
| AL049782 | Unknown | 285.3 | 0.28 |
| X00734 | tubulin, beta, 5 | 39.7 | 0.29 |
| AK001761 | retinoic acid induced 3 | 23.7 | 0.29 |
| U72661 | ninjurin 1 | 4.4 | 0.29 |
| S48220 | deiodinase, iodothyronine, type I | 1,296.1 | 0.29 |
| AF025304 | EphB2 | 4.5 | 0.30 |
| S82198 | chymotrypsin C | 4.1 | 0.30 |
| Z80782 | H2B histone family, member K | 31.9 | 0.30 |
| X68194 | synaptophysin-like protein | 7.9 | 0.30 |
| AB028869 | Unknown | 4.2 | 0.30 |
| AK000761 | Unknown | 4.3 | 0.30 |

TABLE 57

Polynucleotides expressed to similar extents after stimulation by the bacterial products LPS, LTA, and CpG DNA.
Bacterial products (100 ng/ml *S. typhimurium* LPS, 1 µg/ml *S. aureus* LTA or 1 µM CpG) were shown to potently induce the expression of several polynucleotides. Peptide was incubated with the RAW cells for 4 h and the RNA was isolated, converted into labeled cDNA probes and hybridized to Atlas arrays. The intensity of control, unstimulated cells is shown in the second column. The "Ratio LPS/LTA/CpG: Control" column refers to the intensity of polynucleotide expression in bacterial product-simulated cells divided by the intensity of unstimulated cells.

| Accession number | Control Unstim. Intensity | Ratio LPS: Control | Ratio LTA: Control | Ratio CpG: Control | Protein/polynucleotide |
|---|---|---|---|---|---|
| M15131 | 20 | 82 | 80 | 55 | IL-1β |
| M57422 | 20 | 77 | 64 | 90 | tristetraprolin |
| X53798 | 20 | 73 | 77 | 78 | MIP-2α |
| M35590 | 188 | 50 | 48 | 58 | MIP-1β |
| L28095 | 20 | 49 | 57 | 50 | ICE |
| M87039 | 20 | 37 | 38 | 45 | iNOS |
| X57413 | 20 | 34 | 40 | 28 | TGFβ |
| X15842 | 20 | 20 | 21 | 15 | c-rel proto-oncopolynucleotide |
| X12531 | 489 | 19 | 20 | 26 | MIP-1α |
| U14332 | 20 | 14 | 15 | 12 | IL-15 |
| M59378 | 580 | 10 | 13 | 11 | TNFR1 |
| U37522 | 151 | 6 | 6 | 6 | TRAIL |
| M57999 | 172 | 3.8 | 3.5 | 3.4 | NF-κB |
| U36277 | 402 | 3.2 | 3.5 | 2.7 | I-κB (alpha subunit) |
| X76850 | 194 | 3 | 3.8 | 2.5 | MAPKAP-2 |
| U06924 | 858 | 2.4 | 3 | 3.2 | Stat 1 |
| X14951 | 592 | 2 | 2 | 2 | CD18 |
| X60671 | 543 | 1.9 | 2.4 | 2.8 | NF-2 |
| M34510 | 5970 | 1.6 | 2 | 1.4 | CD14 |
| X51438 | 2702 | 1.3 | 2.2 | 2.0 | vimentin |
| X68932 | 4455 | 0.5 | 0.7 | 0.5 | c-Fms |
| Z21848 | 352 | 0.5 | 0.6 | 0.6 | DNA polymerase |
| X70472 | 614 | 0.4 | 0.6 | 0.5 | B-myb |

TABLE 58

Polynucleotides that were differentially regulated by the bacterial
products LPS, LTA, and CpG DNA.
Bacterial products (100 ng/ml S. typhimurium LPS, 1 μg/ml S. aureus LTA or 1 μM
CpG) were shown to potently induce the expression of several polynucleotides.
Peptide was incubated with the RAW cells for 4 h and the RNA was isolated, converted
into labeled cDNA probes and hybridized to Atlas arrays. The intensity of control,
unstimulated cells is shown in the second column. The "Ratio LPS/LTA/CpG: Control"
column refers to the intensity of polynucleotide expression in bacterial product-simulated
cells divided by the intensity of unstimulated cells.

| Accession number | Unstim. Control Intensity | Ratio LPS: Control | Ratio LTA: Control | Ratio CpG: Control | Protein/polynucleotide |
|---|---|---|---|---|---|
| X72307 | 20 | 1.0 | 23 | 1.0 | hepatocyte growth factor |
| L38847 | 20 | 1.0 | 21 | 1.0 | hepatoma transmembrane kinase ligand |
| L34169 | 393 | 0.3 | 3 | 0.5 | thrombopoietin |
| J04113 | 289 | 1 | 4 | 3 | Nur77 |
| Z50013 | 20 | 7 | 21 | 5 | H-ras proto-oncopolynucleotide |
| X84311 | 20 | 4 | 12 | 2 | Cyclin A1 |
| U95826 | 20 | 5 | 14 | 2 | Cyclin G2 |
| X87257 | 123 | 2 | 4 | 1 | Elk-1 |
| J05205 | 20 | 18 | 39 | 20 | Jun-D |
| J03236 | 20 | 11 | 19 | 14 | Jun-B |
| M83649 | 20 | 71 | 80 | 42 | Fas 1 receptor |
| M83312 | 20 | 69 | 91 | 57 | CD40L receptor |
| X52264 | 20 | 17 | 23 | 9 | ICAM-1 |
| M13945 | 573 | 2 | 3 | 2 | Pim-1 |
| U60530 | 193 | 2 | 3 | 3 | Mad related protein |
| D10329 | 570 | 2 | 3 | 2 | CD7 |
| X06381 | 20 | 55 | 59 | 102 | Leukemia inhibitory factor (LIF) |
| X70296 | 20 | 6.9 | 13 | 22 | Protease nexin 1 (PN-1) |
| U36340 | 20 | 38 | 7 | 7 | CACCC Box-binding protein BKLF |
| S76657 | 20 | 11 | 6 | 7 | CRE-BPI |
| U19119 | 272 | 10 | 4 | 4 | interferon inducible protein 1 |

TABLE 59

Confirmation of Table 57 and 58 Array Data.

| | Relative levels | | | |
|---|---|---|---|---|
| Product | Untreated | LPS | LTA | CpG |
| CD14[a] | 1.0 | 2.2 ± 0.4 | 1.8 ± 0.2 | 1.5 ± 0.3 |
| Vimentin[a] | 1.0 | 1.2 ± 0.07 | 1.5 ± 0.05 | 1.3 ± 0.07 |
| Tristetraprolin[a] | 1.0 | 5.5 ± 0.5 | 5.5 ± 1.5 | 9.5 ± 1.5 |
| LIF[b] | 1.0 | 2.8 ± 1.2 | 2.7 ± 0.6 | 5.1 ± 1.6 |
| NO[c] | 8 ± 1.5 | 47 ± 2.5 | 20 ± 3 | 21 ± 1.5 |

[a]Total RNA was isolated from unstimulated RAW macrophage cells and cells treated for 4 hr with 100 ng/ml S. typhimurium LPS, 1 μg/ml S. aureus LTA, 1 μM CpG DNA or media alone and Northern blots were performed the membrane was probed for GAPDH, CD14, vimentin, and tristetraprolin as described previously [Scott et al]. The hybridization intensities of the Northern blots were compared to GAPDH to look forinconsistencies in loading. These experiments were repeated at least three times and the data shown is the average relative levels of each condition compared to media (as measured by densitometry) ± standard error.
[b]RAW 264.7 cells were stimulated with 100 ng/ml S. typhimurium LPS, 1 μg/ml S. aureus LTA, 1 μM CpG DNA or media alone for 24 hours. Protein lysates were prepared, run on SDS PAGE gels and western blots were performed to detect LIF (R&D Systems). These experiments were repeated at least three times and the data shown is the relative levels of LIF compared to media (as measured by densitometry) ± standard error.
[c]Supernatant was collected from RAW macrophage cells treated with 100 ng/ml S. typhimurium LPS, 1 μg/ml S. aureus LTA, 1 μM CpG DNA, or media alone for 24 hours and tested for the amount of NO formed in the supernatant as estimated from the accumulation of the stable NO metabolite nitrite with the Griess reagent as described previously [Scott, et al]. The data shown is the average of three experiments ± standard error.

TABLE 60

Pattern of Gene expression in A549 Human Epithelial cells
up-regulated by bacterial signalling molecules (LPS).
E. coli O111: B4 LPS (100 ng/ml) increased the expression of many
polynucleotides in A549 cells as studied by polynucleotide
microarrays. LPS was incubated with the A549 cells for 4 h
and the RNA was isolated. 5 μg total RNA was used to
make Cy3/Cy5 labelled cDNA probes and hybridised onto
Human Operon arrays (PRHU04). The examples of
polynucleotide expression changes in LPS simulated cells
represent a greater than 2-fold intensity level change of
LPS treated cells from untreated cells.

| Accession Number | Gene |
|---|---|
| AL050337 | interferon gamma receptor 1 |
| U05875 | interferon gamma receptor 2 |
| NM_002310 | leukemia inhibitory factor receptor |
| U92971 | coagulation factor II (thrombin) receptor-like 2 |
| Z29575 | tumor necrosis factor receptor superfamily member 17 |
| L31584 | Chemokine receptor 7 |
| J03925 | cAMP response element-binding protein |
| M64788 | RAP1, GTPase activating protein |
| NM_004850 | Rho-associated kinase 2 |
| D87451 | ring finger protein 10 |
| AL049975 | Unknown |
| U39067 | eukaryotic translation initiation factor 3, subunit 2 |
| AK000942 | Unknown |
| AB040057 | serine/threonine protein kinase MASK |
| AB020719 | KIAA0912 protein |
| AB007856 | FEM-1-like death receptor binding protein |
| AL137376 | Unknown |
| AL137730 | Unknown |
| M90696 | cathepsin S |
| AK001143 | Unknown |

TABLE 60-continued

Pattern of Gene expression in A549 Human Epithelial cells up-regulated by bacterial signalling molecules (LPS).
E. coli O111:B4 LPS (100 ng/ml) increased the expression of many polynucleotides in A549 cells as studied by polynucleotide microarrays. LPS was incubated with the A549 cells for 4 h and the RNA was isolated. 5 µg total RNA was used to make Cy3/Cy5 labelled cDNA probes and hybridised onto Human Operon arrays (PRHU04). The examples of polynucleotide expression changes in LPS simulated cells represent a greater than 2-fold intensity level change of LPS treated cells from untreated cells.

| Accession Number | Gene |
| --- | --- |
| AF038406 | NADH dehydrogenase |
| AK000315 | hypothetical protein FLJ20308 |
| M54915 | pim-1 oncogene |
| D29011 | proteasome subunit, beta type, 5 |
| AL034348 | Unknown |
| D87076 | KIAA0239 protein |
| AJ001403 | mucin 5, subtype B, tracheobronchial |
| J03925 | integrin, alpha M |

EXAMPLE 10

Altering Signaling to Protect Against Bacterial Infections

The Salmonella Typhimurium strain SL1344 was obtained from the American Type Culture Collection (ATCC; Manassas, Va.) and grown in Luria-Bertani (LB) broth. For macrophage infections, 10 ml LB in a 125 mL flask was inoculated from a frozen glycerol stock and cultured overnight with shaking at 37° C. to stationary phase. RAW 264.7 cells ($1 \times 10^5$ cells/well) were seeded in 24 well plates. Bacteria were diluted in culture medium to give a nominal multiplicity of infection (MOI) of approximately 100, bacteria were centrifuged onto the monolayer at 1000 rpm for 10 minutes to synchronize infection, and the infection was allowed to proceed for 20 min in a 37° C., 5% $CO_2$ incubator. Cells were washed 3 times with PBS to remove extracellular bacteria and then incubated in DMEM+10% FBS containing 100 µg/mnl gentarnicin (Sigma, St. Louis, Mo.) to kill any remaining extracellular bacteria and prevent re-infection. After 2 h, the gentamicin concentration was lowered to 10 µg/ml and maintained throughout the assay. Cells were pretreated with inhibitors for 30 min prior to infection at the following concentrations: 50 µM PD 98059 (Calbiochem), 50 µM U 0126 (Promega), 2 mM diphenyliodonium (DPI), 250 µM acetovanillone (apocynin, Aldrich), 1 mM ascorbic acid (Sigma), 30 mM N-acetyl cysteine (Sigma), and 2 mM $N^G$-L-monomethyl arginine (L-NMMA, Molecular Probes) or 2 mM $N^G$-D-monomethyl arginine (D-NMMA, Molecular Probes). Fresh inhibitors were added immediately after infection, at 2 h, and 6-8 h post-infection to ensure potency. Control cells were treated with equivalent volumes of dimethylsulfoxide (DMSO) per mL of media. Intracellular survival/replication of S. Typhimurium SL1344 was determined using the gentamicin-resistance assay, as previously described. Briefly, cells were washed twice with PBS to remove gentamicin, lysed with 1% Triton X-100/0.1% SDS in PBS at 2 h and 24 h post-infection, and numbers of intracellular bacteria calculated from colony counts on LB agar plates. Under these infection conditions, macrophages contained an average of 1 bacterium per cell as assessed by standard plate counts, which permitted analysis of macrophages at 24 h post-infection. Bacterial filiamentation is related to bacterial stress. NADPH oxidase and iNOS can be activated by MEK/ERK signaling. The results (Table 61) clearly demonstrate that the alteration of cell signaling is a method whereby intracellular Salmonella infections can be resolved. Thus since bacteria to up-regulate multiple genes in human cells, this strategy of blocking signaling represents a general method of therapy against infection.

TABLE 61

Effect of the Signaling Molecule MEK on Intracellular Bacteria in IFN-γ-primed RAW cells.

| Treatment[a] | Effect[b] |
| --- | --- |
| 0 | None |
| MEK inhibitor U 0126 | Decrease bacterial filamentation (bacterial stress)[c] |
| | Increase in the number of intracellular S. Typhimurium |
| MEK inhibitor PD 98059 | Decrease bacterial filamentation (bacterial stress)[c] |
| | Increase in the number of intracellular S. Typhimurium |
| NADPH oxidase inhibitor[d] | Decrease bacterial filamentation (bacterial stress)[c] |
| | Increase in the number of intracellular S. Typhimurium |

EXAMPLE 11

Anti-Viral Activity

SDF-1, a C-X-C chemokine is a natural ligand for HIV-1 coreceptor-CXCR4. The chemokine receptors CXCR4 and CCR5 are considered to be potential targets for the inhibition of HIV-1 replication. The crystal structure of SDF-1 exhibits antiparallel β-sheets and a positively charged surface, features that are critical in binding to the negatively charged extracellular loops of CXCR4. These findings suggest that chemokine derivatives, small-size CXCR4 antagonists, or agonists mimicking the structure or ionic property of chemokines may be useful agents for the treatment of X4 HIV-1 infection. It was found that the cationic peptides inhibited SDF-1 induced T-cell migration suggesting that the peptides may act as CXCR4 antagonists. The migration assays were performed as follows. Human Jurkat T cells were resuspended to $5 \times 10^6$/ml in chemotaxis medium (RPMI 1640/10 mM Hepes/0.5% BSA). Migration assays were performed in 24 well plates using 5 µm polycarbonate Transwell inserts (Costar). Briefly, peptide or controls were diluted in chemotaxis medium and placed in the lower chamber while 0.1 ml cells ($5 \times 10^6$/ml) was added to the upper chamber. After 3 hr at 37° C., the number of cells that had migrated into the lower chamber was determined using flow cytometry. The medium from the lower chamber was passed through a FACscan for 30 seconds, gating on forward and side scatter to exclude cell debris. The number of live cells was compared to a "100% migration control" in which $5 \times 10^5$/ml cells had been pipetted directly into the lower chamber and then counted on the FACscan for 30 seconds. The results demonstrate that the addition of peptide results in an inhibition of the migration of Human Jurkat T-cells (Table 62) probably by influencing CXCR4 expression (Tables 63 and 64).

TABLE 62

Peptide inhibits the migration of human Jurkat-T cells:

| | Migration (%) | | | |
|---|---|---|---|---|
| Experiment | Positive control | SDF-1 (100 ng/ml) | SDF-1 + SEQ ID 1 (50 µg/ml) | Negative control |
| 1 | 100% | 32% | 0% | <0.01% |
| 2 | 100% | 40% | 0% | 0% |

TABLE 63

Corresponding polynucleotide array data to Table 56:

| Polynucleotide / Protein | Polynucleotide Function | Unstimulated Intensity | Ratio peptide: Unstimulated | Accession Number |
|---|---|---|---|---|
| CXCR-4 | Chemokine receptor | 36 | 4 | D87747 |

TABLE 64

Corresponding FACs data to Tables 62 and 63:

| Peptide | Concentration (µg/ml) | Fold Increase in Protein Expression CXCR-4 |
|---|---|---|
| SEQ ID NO: 1 | 10 | No change |
| SEQ ID NO: 1 | 50 | 1.3 ± 0.03 |
| SEQ ID NO: 1 | 100 | 1.6 ± 0.23 |
| SEQ ID NO: 3 | 100 | 1.5 ± 0.2 |

Although the invention has been described with reference to the presently preferred embodiment, it should be understood that various modifications can be made without departing from the spirit of the invention. Accordingly, the invention is limited only by the following claims.

---

What is claimed is:

1. An isolated peptide comprising a general formula $X_1X_2X_3IX_4PX_4IPX_5X_2X_1$ (SEQ ID NO: 4), wherein $X_1$ is one or two of R, L or K, $X_2$ is one of C, S or A, $X_3$ is one of R or P, $X_4$ is one of A or V and $X_5$ is one of V or W, and wherein the peptide is LLCRIVPVIPWCK (SEQ ID NO: 5), LRCPIAPVIPVCKK (SEQ ID NO: 6), KSRIVPAIPVSLL (SEQ ID NO: 7), KKSPIAPAIPWSR (SEQ ID NO: 8), RRARIVPAIPVARR (SEQ ID NO: 9) or LSRIAPAIPWAKL (SEQ ID NO: 10).

* * * * *